US009815847B2

(12) United States Patent
Reddy et al.

(10) Patent No.: US 9,815,847 B2
(45) Date of Patent: Nov. 14, 2017

(54) PYRIMIDINE COMPOUNDS AS KINASE INHIBITORS

(71) Applicant: Icahn School of Medicine at Mount Sinai, New York, NY (US)

(72) Inventors: M. V. Ramana Reddy, Blue Bell, PA (US); E. Premkumar Reddy, Villanova, PA (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 21 days.

(21) Appl. No.: 14/775,917

(22) PCT Filed: Mar. 13, 2014

(86) PCT No.: PCT/US2014/026236
§ 371 (c)(1),
(2) Date: Sep. 14, 2015

(87) PCT Pub. No.: WO2014/151682
PCT Pub. Date: Sep. 25, 2014

(65) Prior Publication Data
US 2016/0122361 A1    May 5, 2016

Related U.S. Application Data

(60) Provisional application No. 61/785,754, filed on Mar. 14, 2013.

(51) Int. Cl.
| | | |
|---|---|---|
| *C07D 495/04* | (2006.01) | |
| *C07D 403/12* | (2006.01) | |
| *C07D 401/12* | (2006.01) | |
| *C07D 239/38* | (2006.01) | |
| *C07D 239/47* | (2006.01) | |
| *C07D 239/48* | (2006.01) | |
| *C07D 401/14* | (2006.01) | |
| *C07D 403/14* | (2006.01) | |

(52) U.S. Cl.
CPC ......... *C07D 495/04* (2013.01); *C07D 239/38* (2013.01); *C07D 239/47* (2013.01); *C07D 239/48* (2013.01); *C07D 401/12* (2013.01); *C07D 401/14* (2013.01); *C07D 403/12* (2013.01); *C07D 403/14* (2013.01)

(58) Field of Classification Search
CPC .. C07D 239/38; C07D 239/47; C07D 495/04; C07D 401/12; C07D 401/14; C07D 403/12; C07D 403/14; C07D 239/48
See application file for complete search history.

(56) References Cited

U.S. PATENT DOCUMENTS

| | | |
|---|---|---|
| 2004/0180914 A1 | 9/2004 | Batchelor |
| 2010/0099691 A1 | 4/2010 | Boice |
| 2013/0158057 A1 | 6/2013 | Baker-Glenn |
| 2014/0045840 A1 | 2/2014 | Zhang |

FOREIGN PATENT DOCUMENTS

| | | | |
|---|---|---|---|
| EP | 1364950 A1 | | 11/2003 |
| JP | 2009149618 A | | 7/2009 |
| WO | 98/33798 A1 | | 8/1998 |
| WO | 01/55148 A1 | | 8/2001 |
| WO | 0155147 A1 | | 8/2001 |
| WO | WO 2007/138974 | * | 12/2007 |
| WO | 2011/075616 A1 | | 6/2011 |
| WO | 2011090666 A2 | | 7/2011 |
| WO | 2012/018540 A1 | | 2/2012 |
| WO | 2012/149567 A1 | | 11/2012 |

OTHER PUBLICATIONS

International Search Report for PCT/US14/26236 dated Jun. 20, 2014. 3 pages.
Pubchem SureCN4933440, CID 10080432, pp. 1-5, Create Date: Oct. 25, 2006; p. 1; [retrieved on May 27, 2014]. Retrieved from the Internet: , 25/22-24, 27-29, 90-92 <URL: http://pubchem.ncbi.nlm.nih.gov/summary/summary.cgi?cid=10080432&loc=ec_rcs>.
Pubchem SureCN7898116, CID 70223084, pp. 1-3, Create Date: Dec. 1, 2012; p. 1; [retrieved on May 27, 2014]. Retrieved from the Internet: 25/22-24, 27-29, 90-92 <URL: http://pubchem.ncbi.nlm.nih.gov/summary/summary.cgi?cid=70223084&loc=ec_rcs>.
Pubchem SureCN1093071, CID 53395796, pp. 1-3, Create Date: Oct. 30, 2011; p. 1; [retrieved on May 27, 2014]. Retrieved from the Internet: 25/22-24, 27-29, 90-92 <URL: http://pubchem.ncbi.nlm.nih.gov/summary/summary.cgi?cid=53395796&loc=ec_rcs>.
Pubchem SureCN3629522, CID 59434107, pp. 1-6, Create Date: Aug. 20, 2012; p. 1; [retrieved on May 27, 2014]. Retrieved from the Internet: 25/22-24, 27-29, 90-92 <URL: http://pubchem.ncbi.nlm.nih.gov/summary/summary.cgi?cid=59434107&loc=ec_rcs>.
SCIFINDER® Database Search Results Dated Dec. 19, 2012; 883 pages.
SCIFINDER® Database Search Results (Structures) Dated 2012; 27 pages.
SCIFINDER® Database Search Results (References) Dated 2012; 89 pages.
Extended European Search Report dated Jul. 22, 2016 for EP14770699.8, 8 pages.

* cited by examiner

*Primary Examiner* — Barbara P Badio
*Assistant Examiner* — Sara E Townsley
(74) *Attorney, Agent, or Firm* — Fish & Richardson P.C.

(57) ABSTRACT

This disclosure relates to compounds, methods for their preparation, pharmaceutical compositions including these compounds and methods for the treatment of cellular proliferative disorders, including, but not limited to, cancer.

23 Claims, No Drawings

PYRIMIDINE COMPOUNDS AS KINASE INHIBITORS

CROSS-REFERENCE TO RELATED APPLICATIONS

This application is the national phase under 35 U.S.C. §371 of PCT Application No. PCT/US2014/026236, filed Mar. 13, 2014, which claims the benefit of U.S. Provisional Application No. 61/785,754, filed on Mar. 14, 2013, which is incorporated herein by reference in its entirety.

TECHNICAL FIELD

This disclosure relates to compounds, methods for their preparation, pharmaceutical compositions including these compounds and methods for the treatment of cellular proliferative disorders, including, but not limited to, cancer.

BACKGROUND

Cellular proliferative disorders are among the most common causes of death in developed countries. For diseases for which treatments exist, such as cancer, the existing treatments have undesirable side effects and limited efficacy. Identifying new effective drugs for cellular proliferative disorders, including cancer, is a continuing focus of medical research.

SUMMARY

It has been found that certain compounds and compositions are kinase inhibitors and are useful for the treatment of cellular proliferative disorders including, but not limited to cancer. The compounds are useful, e.g., as pharmaceuticals.

The disclosure describes compounds of formula (I):

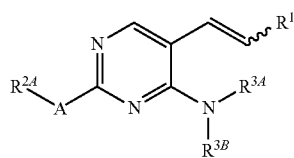

or a pharmaceutically acceptable salt thereof; wherein the variables are as defined below.

A method for treating a cellular proliferative disorder in a patient is provided. The method includes administering to the patient a therapeutically effective amount of a compound of formula (I), or a pharmaceutically acceptable salt thereof.

A method of treating a neurological disorder in a patient is provided. The method includes administering to the patient a therapeutically effective amount of a compound of formula (I), or a pharmaceutically acceptable salt thereof.

A method of inhibiting one or more kinases in a patient is provided. The method includes administering to the patient a therapeutically effective amount of a compound of formula (I) or a pharmaceutically acceptable salt thereof.

A method of inhibiting one or more kinases in a cell is provided. The method includes contacting the cell with an effective amount of a compound of formula (I) or a pharmaceutically acceptable salt thereof.

A method of inhibiting cellular proliferation of cancer cells in a patient is provided. The method includes administering to the patient a therapeutically effective amount of a compound of formula (I) or a pharmaceutically acceptable salt thereof.

A method of inducing cell death of cancer cells in a patient is provided. The method includes administering to the patient a therapeutically effective amount of a compound of formula (I) or a pharmaceutically acceptable salt thereof.

A method of inducing apoptosis of cancer cells in a patient is provided. The method includes administering to the patient a therapeutically effective amount of a compound of formula (I) or a pharmaceutically acceptable salt thereof.

A method of inducing apoptosis in a cell is provided. The method includes contacting the cell with an effective amount of a compound of formula (I) or a pharmaceutically acceptable salt thereof.

DETAILED DESCRIPTION

It is appreciated that certain features described herein, which are, for clarity, described in the context of separate embodiments, can also be provided in combination in a single embodiment. Conversely, various features described herein which are, for brevity, described in the context of a single embodiment, can also be provided separately or in any suitable subcombination.

I. Definitions

Unless defined otherwise, all technical and scientific terms used herein have the same meaning as is commonly understood by one of ordinary skill in the art to which this disclosure belongs. In the event that there is a plurality of definitions for terms cited herein, those in this section prevail unless otherwise stated.

The terms "e.g.," and "such as," and grammatical equivalents thereof, the phrase "and without limitation" is understood to follow unless explicitly stated otherwise.

The singular forms "a," "an," and "the" include plural referents unless the context clearly dictates otherwise.

The term "about" means "approximately" (e.g., plus or minus approximately 10% of the indicated value).

The term "salt" includes any ionic form of a compound and one or more counter-ionic species (cations and/or anions). The term includes derivatives of the disclosed compounds wherein the parent compound is modified by converting an existing acid or base moiety to its salt form. Salts also include zwitterionic compounds (i.e., a molecule containing one more cationic and anionic species, e.g., zwitterionic amino acids). Examples of salts include, but are not limited to, mineral or organic acid salts of basic residues such as amines; alkali or organic salts of acidic residues such as carboxylic acids; and the like. Counter ions present in a salt can include any cationic, anionic, or zwitterionic species. Exemplary anions include, but are not limited to, chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluormethansulfonate, ethanesulfonate, benzenesulfonate, p-toluenesulfonate, p-trifluoromethylbenzenesulfonate, hydroxide, aluminates and borates. Exemplary cations include, but are not limited, to monovalent alkali metal cations, such as lithium, sodium, potassium and cesium, and divalent alkaline earth metals, such as beryllium, magnesium, calcium, strontium and barium. Also included are transition metal cations, such as gold, silver, copper and zinc, as well as non-metal cations, such as ammonium salts. The term "pharmaceutically-acceptable salt" refers to salts which possess toxicity profiles within a range that affords utility in pharmaceutical applications. The pharmaceutically acceptable salts of the present invention include the non-toxic salts of the parent compound formed, e.g., from non-toxic inorganic or organic acids. Pharmaceutically unacceptable salts may nonetheless possess properties such as high crystallinity, which may render them useful, e.g., in processes of synthesis, purification or formulation of compounds described herein. Unless clearly indicated otherwise (such as specifying that the compound should be in "free base" or "free acid" form), reference in the specification to a compound should be understood as including salt forms of the compound, whether or not this is explicitly stated. The salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Preparation and selection of suitable salt forms is described in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

The term "compound" includes all stereoisomers, geometric isomers, tautomers and isotopes of the structures depicted. Compounds herein identified by name or structure as one particular tautomeric form are intended to include other tautomeric forms unless otherwise specified. Compounds provided herein can also include all isotopes of atoms occurring in the intermediates or final compounds. Isotopes include those atoms having the same atomic number but different mass numbers. For example, isotopes of hydrogen include tritium and deuterium.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" it is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The phrase "optionally substituted" means unsubstituted or substituted. The term "substituted" means that a hydrogen atom is removed and replaced by a substituent. A single divalent substituent, e.g., oxo, can replace two hydrogen atoms.

The term "C$_{n-m}$" indicates a range which includes the endpoints, wherein n and m are integers and indicate the number of carbons. Examples include C$_{1-4}$, C$_{1-6}$ and the like.

The term "alkyl" employed alone or in combination with other terms, refers to a saturated hydrocarbon group that may be straight-chain or branched. The term "C$_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like. Alkyl groups can be straight-chained, e.g., methyl, ethyl, n-propyl and n-butyl, or branched, e.g., i-propyl, t-butyl and 2,2-dimethylethyl. C$_{x-y}$ alkyl groups include C$_{1-6}$ alkyl and C$_{1-3}$, e.g., methyl and ethyl.

The term "alkenyl" refers to straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "C$_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" refers to straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. An alkenyl group can be straight-chained or branched. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" refers to an alkyl group in which one or more of the hydrogen atoms has been replaced by a halogen atom. The term "$C_{n-m}$ haloalkyl" refers to a $C_{n-m}$ alkyl group having n to m carbon atoms, and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl.

The term "heteroaryl" or "heteroaromatic," employed alone or in combination with other terms, refers to a monocyclic or polycyclic aromatic heterocycle having at least one heteroatom ring member selected from sulfur, oxygen, and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl group having five ring atoms wherein one or more (e.g., 1, 2 or 3) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O, and S. Exemplary six-membered ring heteroaryls are pyridyl, pyrazinyl, pyrimidinyl, triazinyl and pyridazinyl.

The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2, or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., $C(O)$, $S(O)$, $C(S)$, or $S(O)_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring.

The term "carbocycle" refers to an aryl group or a cycloalkyl group.

The term "heterocycle" refers to a heteroaryl group or a heterocycloalkyl group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral center, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" are understood in the art, and refer generally to a temperature, e.g., a reaction temperature, that is about the temperature of the room in which the reaction is carried out, e.g., a temperature from about 20° C. to about 30° C.

The following abbreviations may be used herein: AcOH (acetic acid); $Ac_2O$ (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DCM (dichloromethane); DIAD (N,N'-diisopropyl azidodicarboxylate); DIC (N,N'-diisopropylcarbodiimide); DIPEA (N,N-diisopropylethylamine); DMAP (4-dimethylaminopyridine); DMF (N,N-dimethylformamide); equiv. (equivalent(s)); Et (ethyl); EtOAc (ethyl acetate); Fmoc (9-fluorenylmethylmethoxycarbonyl); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); $K_3PO_4$ (potassium phosphate); LCMS (liquid chromatography-mass spectrometry); m (multiplet); m.p. (melting point); M (molar); mCPBA (3-chloroperoxybenzoic acid); $MgSO_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4Cl$ (ammonium chloride); $NH_4OH$ (ammonium hydroxide); nM (nanomolar); NMR (nuclear magnetic resonance spectroscopy); OTf (trifluoromethanesulfonate); Pd (palladium); pM (picomolar); POCl$_3$ (phosphoryl chloride); RP-HPLC (reverse phase high performance liquid chromatography); rt (room temperature); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

The term "contacting" means bringing at least two moieties together, whether in an in vitro system or an in vivo system.

As used herein, the terms "individual" or "patient," used interchangeably, refer to (e.g., as a subject of the treatment) any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

II. Novel Compounds

This disclosure provides compounds of formula (I):

or a salt thereof, wherein:

$R^1$ is CN, $S(O)_j Ar^1$, $S(O)_k(C_{1-6}$ alkylene)$Ar^1$; —NO$_2$, —C(O)$R^{1A}$; —C(O)O$R^{1B}$ or —C(O)N$R^{1C}R^{1D}$;

j is 0, 1 or 2;

k is 0, 1 or 2;

each $Ar^1$ is independently $C_{6-10}$ aryl or 5-10 membered heteroaryl, each of which is unsubstituted or substituted by 1, 2, 3, 4 or 5 substituents independently selected from $Cy^1$, $C_{1-6}$ alkyl, $C_{2-6}$ alkenyl, $C_{2-6}$ alkynyl, halo, $C_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O) OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$ and S(O)$_2$NR$^{c1}$R$^{d1}$;

each $Cy^1$ is independently $C_{6-10}$ aryl, $C_{3-10}$ cycloalkyl, 5-10 membered heteroaryl or 4-10 membered heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$) NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C (O)NR$^{c1}$R$^{d1}$, NR$^{c1}$S(O)R$^{b1}$, NR$^{c1}$S(O)$_2$R$^{b1}$, NR$^{c1}$S(O)$_2$ NR$^{c1}$R$^{d1}$, S(O)R$^{b1}$, S(O)NR$^{c1}$R$^{d1}$, S(O)$_2$R$^{b1}$, S(O)$_2$ NR$^{c1}$R$^{d1}$ and oxo;

$R^{1A}$ is H, $R^{1E}$, $C_{2-6}$ alkenyl, $C_{2-6}$ alkynyl, $Ar^1$ or $(C_{1-6}$ alkylene)$Ar^1$;

$R^{1B}$ is H, $R^{1E}$, $C_{2-6}$ alkenyl, $C_{2-6}$ alkynyl, $Ar^1$, $(C_{1-6}$ alkylene)$Ar^1$, —N($C_{1-6}$ alkyl)$_2$, —CH($R^{1F}$)—CH$_2$—S(O)$_m$ ($C_{1-6}$ alkyl); —CH($R^{1F}$)—CH$_2$—N($R^{1F}$)C(O)O($C_{1-6}$ alkyl) or —CH($R^{1F}$)—CH$_2$—OC(O)CH($R^{1G}$)NH$_2$;

$R^{1C}$ is H, $R^{1E}$, $C_{2-6}$ alkenyl, $C_{2-6}$ alkynyl, $Ar^1$ or $(C_{1-6}$ alkylene)$Ar^1$;

$R^{1D}$ is H, $C_{1-6}$ alkyl, $C_{2-6}$ alkenyl, $C_{2-6}$ alkynyl, $Ar^1$ or $(C_{1-6}$ alkylene)$Ar^1$;

or $R^{1C}$ and $R^{1D}$, together with the N atom to which they are attached, form a 5-, 6-, or 7-membered heterocycloalkyl group, which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S (O)R$^{b1}$, NR$^{c1}$S(O)$_2$R$^{b1}$, NR$^{c1}$S(O)$_2$NR$^{c1}$R$^{d1}$, S(O)R$^{b1}$, S(O) NR$^{c1}$R$^{d1}$, S(O)$_2$R$^{b1}$, S(O)$_2$NR$^{c1}$R$^{d1}$, oxo, $Ar^1$, $(C_{1-6}$ alkylene)$Ar^1$ or C(O)$Ar^1$;

each $R^{1E}$ is independently unsubstituted $C_{1-6}$ alkyl or $C_{1-6}$ alkyl substituted by 1, 2 or 3 substituents independently selected from $C_{1-6}$ alkyl, $C_{2-6}$ alkenyl, $C_{2-6}$ alkynyl, halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C (=NR$^{e1}$)NR$^{c1}$R$^{d1}$, NR$^{c1}$R$^{d1}$, NR$^{c1}$C(O)R$^{b1}$, NR$^{c1}$C(O) OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$ and oxo;

each $R^{1F}$ is independently H or $C_{1-6}$ alkyl;

$R^{1G}$ is H, $C_{1-6}$ alkyl; —(($C_1$-$C_6$)alkylene)-OR$^{1H}$, —(($C_1$-$C_6$)alkylene)-NR$^{1H}_2$, —(($C_1$-$C_6$)alkylene)-SR$^{1H}$, —(($C_1$-$C_6$)alkylene)-C(=O)OR$^{1H}_2$, ((C$_1$-C$_6$)alkylene)-C(=O) NR$^{1H}_2$, —((C$_1$-C$_6$)alkylene)-C(=NR$^{1H}$)NR$^{1H}_2$, —((C$_1$-C$_6$) alkylene)-OC(=O)R$^{1H}$, —((C$_1$-C$_6$)alkylene)-NR$^{1H}$C(=O) R$^{1H}$, —((C$_1$-C$_6$)alkylene)-NR$^H$C(=NR$^H$)NR$^{4a}_2$, $Ar^{1G}$ and —((C$_1$-C$_6$)alkylene)$Ar^{1G}$;

each $Ar^{1G}$ is independently unsubstituted phenyl or phenyl which is substituted by 1, 2, 3, 4 or 5 substituents independently selected from $C_{1-6}$ alkyl, $C_{2-6}$ alkenyl, $C_{2-6}$ alkynyl, halo, $C_{1-6}$ haloalkyl, CN, NO$_2$, OR$^{a1}$, SR$^{a1}$, C(O) R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S (O)R$^{b1}$, NR$^{c1}$S(O)$_2$R$^{b1}$, NR$^{c1}$S(O)$_2$NR$^{c1}$R$^{d1}$, S(O)R$^{b1}$, S(O) NR$^{c1}$R$^{d1}$, S(O)$_2$R$^{b1}$ and S(O)$_2$NR$^{c1}$R$^{d1}$;

each $R^{1H}$ is independently H or $C_{1-6}$ alkyl;

m is 0, 1 or 2;

A is NR$^{2B}$, O or S(O)$_n$;

n is 0, 1 or 2;

$R^{2A}$ is $C_{1-6}$ alkyl, $C_{2-6}$ alkenyl, $C_{2-6}$ alkynyl, $Ar^2$ or $(C_{1-6}$ alkylene)$Ar^2$;

$R^{2B}$ is H, $C_{1-6}$ alkyl, $C(O)C_{1-6}$ alkyl, $Cy^{2A}$, $C(O)Cy^{2A}$, $(C_{1-6}$ alkylene$)Cy^{2A}$ and $C(O)(C_{1-6}$ alkylene$)Cy^{2A}$;

or $R^{2A}$ and $R^{2B}$, together with the N atom to which they are attached, form a 5-, 6-, or 7-membered heterocycloalkyl group, which is unsubstituted or substituted by 1, 2, 3, 4 or 5 substituents independently selected from $R^{Cy2}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo;

$Ar^2$ is $C_{6-10}$ aryl or 5-10 membered heteroaryl, each of which is unsubstituted or substituted by 1, 2, 3, 4 or 5 substituents independently selected from $Cy^{2B}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$;

$Cy^{2A}$ is $C_{6-10}$ aryl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $Cy^{2B}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo;

each $Cy^{2B}$ is independently $C_{6-10}$ aryl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo;

$R^{3A}$ is H, $Cy^{3A1}$ or $C_{1-6}$ alkyl, $C_{2-6}$ alkenyl, $C_{1-6}$ alkynyl, wherein said $C_{1-6}$ alkyl forming $R^{3A}$ is optionally substituted with 1, 2, or 3 substituents independently selected from $Cy^{3A2}$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{d3})NR^{c3}R^{d3}$, $NR^{a3}C(=NR^{d3})NR^{c3}R^{d3}$, $NR^{c3}R^{d3}$, $NR^{c3}C(O)R^{b3}$, $NR^3C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

$R^{3B}$ is H, $Cy^{3B1}$ or $C_{1-6}$ alkyl, $C_{2-6}$ alkenyl, $C_{1-6}$ alkynyl, wherein said $C_{1-6}$ alkyl forming $R^{3B}$ is optionally substituted with 1, 2, or 3 substituents independently selected from $Cy^{3B2}$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{d3})NR^{c3}R^{d3}$, $NR^{a3}C(=NR^{d3})NR^{c3}R^{d3}$, $NR^{a3}R^{d3}$, $NR^{c3}C(O)R^{b3}$, $NR^3C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

each $Cy^{3A1}$, $Cy^{3A2}$, $Cy^{3B1}$ and $Cy^{3B2}$ is, independently, $C_{6-10}$ aryl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)$ $OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{e3}S(O)_2R^{b3}$, $NR^{c3}S(O)_2NR^{c3}R^{d3}$, $S(O)R^{b3}$ $S(O)NR^{c3}R^{d3}$, $S(O)_2R^{b3}$, $S(O)_2NR^{c3}R^{d3}$ and oxo;

or $R^{3A}$ and $R^{3B}$, together with the N atom to which they are attached, form a 5-, 6-, or 7-membered heterocycloalkyl group, which is unsubstituted or substituted by 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

each $R^{Cy3}$ is independently selected from $C_{6-10}$ aryl, $C_{3-7}$ cycloalkyl, 5-10 membered heteroaryl, 5-10 heterocycloalkyl, $C_{1-6}$ alkyl, $C_{2-6}$ alkenyl, $C_{2-6}$ alkynyl, halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}S(O)R^{b3}$, $R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)$ $NR^{c3}R^{d3}$, $S(O)_2R^{b3}$, $S(O)_2NR^{c3}R^{d3}$ and oxo; wherein each of said $C_{6-10}$ aryl, $C_{3-7}$ cycloalkyl, 5-10 membered heteroaryl and 5-10 heterocycloalkyl forming $R^{Cy3}$ is independently unsubstituted or substituted by 1, 2, or 3 substituents independently selected from $C_{1-6}$ alkyl, $C_{2-6}$ alkenyl, $C_{2-6}$ alkynyl, halo, $C_{1-6}$ haloalkyl, CN, $NO_2$, $OR^{a3}$, $SR^{a3}$, $C(O)$ $R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$ and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$alkyl, $C_{3-10}$ cycloalkyl-$C_{1-4}$ alkyl, (5-10 membered heteroaryl)-$C_{1-4}$ alkyl or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

or any $R^{c1}$ and $R^{d1}$ attached to the same N atom, any $R^{c2}$ and $R^{d2}$ attached to the same N atom, any $R^{c3}$ and $R^{d3}$ attached to the same N atom, or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)$ $OR^{a4}$, $C(=NR^{e4})NR^{c4}R^{d4}$, $NR^{c4}C(=NR^{e4})NR^{c4}R^{d4}$, $S(O)$ R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$ and S(O)$_2$NR$^{c4}$R$^{d4}$;

each R$^{a4}$, R$^{b4}$, R$^{c4}$ and R$^{d4}$ is independently selected from H, C$_{1-4}$ alkyl, C$_{1-4}$ haloalkyl, C$_{2-4}$ alkenyl and C$_{2-4}$ alkynyl, wherein said C$_{1-4}$ alkyl, C$_{2-4}$ alkenyl, and C$_{2-4}$ alkynyl, is optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

or any R$^{c4}$ and R$^{d4}$ attached to the same N atom, together with the N atom to which they are attached, form a 3-, 4-, 5-, 6-, or 7-membered heterocycloalkyl group optionally substituted with 1, 2, or 3 substituents independently selected from OH, CN, amino, halo, C$_{1-6}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl and C$_{1-4}$ haloalkoxy; and each R$^{e1}$, R$^{e2}$, R$^{e3}$ and R$^{e4}$ is independently selected from H, C$_{1-4}$ alkyl and CN.

In some embodiments, the compound can be other than any one or more of the following compounds, and salts thereof:

3-(4-methylamino-2-methanesulfanyl-pyrimidin-5-yl)-acrylonitrile;
3-(4-ethylamino-2-phenylamino-pyrimidin-5-yl)acrylonitrile;
3-(4-amino-2-methanesulfanyl-pyrimidin-5-yl)-acrylic acid;
3-(4-amino-2-methanesulfanyl-pyrimidin-5-yl)-acrylic acid ethyl ester;
esters of 3-(4-amino-2-methanesulfanyl-pyrimidin-5-yl)-acrylic acid;
3-(4-methylamino-2-methanesulfanyl-pyrimidin-5-yl)-acrylic acid;
3-(4-methylamino-2-methanesulfanyl-pyrimidin-5-yl)-acrylic acid ethyl ester;
esters of 3-(4-methylamino-2-methanesulfanyl-pyrimidin-5-yl)-acrylic acid;
3-(4-ethylamino-2-methanesulfanyl-pyrimidin-5-yl)-acrylic acid;
3-(4-ethylamino-2-methanesulfanyl-pyrimidin-5-yl)-acrylic acid;
esters of 3-(4-ethylamino-2-methanesulfanyl-pyrimidin-5-yl)-acrylic acid ethyl ester;
3-(4-cyclopropylamino-2-methanesulfanyl-pyrimidin-5-yl)acrylic acid;
3-(4-cyclopropylamino-2-methanesulfanyl-pyrimidin-5-yl)acrylic acid ethyl ester;
esters of 3-(4-cyclopropylamino-2-methanesulfanyl-pyrimidin-5-yl)acrylic acid;
3-(4-cyclopentylamino-2-methanesulfanyl-pyrimidin-5-yl)acrylic acid;
3-(4-cyclopentylamino-2-methanesulfanyl-pyrimidin-5-yl)acrylic acid ethyl ester;
esters of 3-(4-cyclopentylamino-2-methanesulfanyl-pyrimidin-5-yl)acrylic acid;
3-(4-cyclohexylamino-2-methanesulfanyl-pyrimidin-5-yl)acrylic acid;
3-(4-cyclohexylamino-2-methanesulfanyl-pyrimidin-5-yl)acrylic acid ethyl ester;
esters of 3-(4-cyclohexylamino-2-methanesulfanyl-pyrimidin-5-yl)acrylic acid;
3-(4-methoxybenzylamino-2-methanesulfanyl-pyrimidin-5-yl)acrylic acid;
3-(4-methoxybenzylamino-2-methanesulfanyl-pyrimidin-5-yl)acrylic acid ethyl ester;
esters of 3-(4-methoxybenzylamino-2-methanesulfanyl-pyrimidin-5-yl)acrylic acid;
3-2-methanesulfanyl-4-phenylamino-pyrimidin-5-yl)acrylic acid;
3-2-methanesulfanyl-4-phenylamino-pyrimidin-5-yl)acrylic acid ethyl ester;
esters of 3-2-methanesulfanyl-4-phenylamino-pyrimidin-5-yl)acrylic acid;
3-(4-amino-2-phenylamino-pyrimidin-5-yl)acrylic acid;
3-(4-amino-2-phenylamino-pyrimidin-5-yl)acrylic acid ethyl ester;
esters of 3-(4-amino-2-phenylamino-pyrimidin-5-yl)acrylic acid;
3-(4-ethylamino-2-phenylamino-pyrimidin-5-yl)acrylic acid;
3-(4-ethylamino-2-phenylamino-pyrimidin-5-yl)acrylic acid ethyl ester; and
esters of 3-(4-ethylamino-2-phenylamino-pyrimidin-5-yl) acrylic acid.

In some embodiments, the compound can be other than any one or more of the following compounds, and salts thereof:

3-(4-alkylamino-2-alkanesulfanyl-pyrimidin-5-yl)-acrylonitriles;
3-(4-alkylamino-2-phenylamino-pyrimidin-5-yl)acrylonitriles;
3-(4-amino-2-alkanesulfanyl-pyrimidin-5-yl)-acrylic acids and esters thereof;
3-(4-alkylamino-2-alkanesulfanyl-pyrimidin-5-yl)-acrylic acids and esters thereof;
3-(4-cycloalkylamino-2-alkanesulfanyl-pyrimidin-5-yl) acrylic acids and esters thereof;
3-(4-methoxybenzylamino-2-alkanesulfanyl-pyrimidin-5-yl)acrylic acids and esters thereof;
3-2-alkanesulfanyl-4-phenylamino-pyrimidin-5-yl)acrylic acids and esters thereof;
3-(4-amino-2-phenylamino-pyrimidin-5-yl)acrylic acid and esters thereof; and
3-(4-alkylamino-2-phenylamino-pyrimidin-5-yl)acrylic acids and esters thereof.

In some embodiments, when R$^1$ is CN, R$^{2A}$ A is other than a C$_{1-6}$ alkanesulfanyl group.

In some embodiments, when R$^1$ is —C(O)OR$^{1A}$, R$^{2A}$ A is other than a C$_{1-6}$ alkanesulfanyl group.

In some embodiments, when R$^1$ is CN, R$^{2A}$ A is other than phenylamino group.

In some embodiments, when R$^1$ is —C(O)OR$^{1A}$, R$^{2A}$ A is other than a phenylamino group.

In some embodiments, when R$^1$ is CN, NR$^{3A}$R$^{3B}$ is other than an NH$_2$ group.

In some embodiments, when R$^1$ is —C(O)OR$^A$, NR$^{3A}$R$^{3B}$ is other than an NH$_2$ group.

In some embodiments, when R$^1$ is CN, NR$^{3A}$R$^{3B}$ is other than an —NH—C$_{1-6}$ alkyl group.

In some embodiments, when R$^1$ is —C(O)OR$^{1A}$, NR$^{3A}$R$^{3B}$ is other than an —NH—C$_{1-6}$ alkyl group.

In some embodiments, when R$^1$ is CN, NR$^{3A}$R$^{3B}$ is other than an —NH-cycloalkyl group.

In some embodiments, when R$^1$ is —C(O)OR$^{1A}$, NR$^{3A}$R$^{3B}$ is other than an —NH-cycloalkyl group.

In some embodiments, when R$^1$ is CN, both R$^{3A}$ and R$^{3B}$ are other than H.

In some embodiments, when R$^1$ is —C(O)OR$^{1A}$, both R$^{3A}$ and R$^{3B}$ are other than H.

In some embodiments, R$^1$ is CN.
In some embodiments, R$^1$ is S(O)$_j$Ar$^1$.
In some embodiments, j is 0.
In some embodiments, j is 1.
In some embodiments, j is 2.

In some embodiments, $R^1$ is $S(O)_k(C_{1-6}$ alkylene)$Ar^1$.
In some embodiments, k is 0.
In some embodiments, k is 1.
In some embodiments, k is 2.
In some embodiments, $R^1$ is —$NO_2$.
In some embodiments, $R^1$ is —$C(O)R^{1A}$.
In some embodiments, $R^{1A}$ is H.
In some embodiments, $R^{1A}$ is $C_{1-6}$ alkyl.
In some embodiments $R^{1A}$ is methyl. In some embodiments $R^{1A}$ is ethyl.
In some embodiments, $R^1$ is —$C(O)OR^B$.
In some embodiments, $R^{1B}$ is H. In some embodiments $R^{1B}$ is methyl. In some embodiments $R^{1B}$ is ethyl.
In some embodiments, $R^{1B}$ is $R^{1E}$.
In some embodiments, $R^{1B}$ is $C_{1-6}$ alkyl.
In some embodiments, $R^B$ is —$N(C_{1-6}$ alkyl$)_2$.
In some embodiments, $R^{1B}$ is —$CH(R^{1F})$—$CH_2$—$S(O)_m$ $(C_{1-6}$ alkyl).
In some such embodiments, $R^{1F}$ is H.
In some such embodiments, $R^{1F}$ is $C_{1-6}$ alkyl.
In some such embodiments, m is 0.
In some such embodiments, m is 1.
In some such embodiments, m is 2.
In some embodiments, $R^{1B}$ is —$CH(R^{1F})$—$CH_2$—N$(R^{1F})C(O)O(C_{1-6}$ alkyl).
In some such embodiments, $R^{1F}$ is H.
In some such embodiments, $R^{1F}$ is $C_{1-6}$ alkyl.
In some such embodiments, $R^{1B}$ is —$CH(R^F)$—$CH_2$—$OC(O)CH(R^{1G})NH_2$.
In some such embodiments, $R^{1F}$ is H.
In some such embodiments, $R^{1F}$ is $C_{1-6}$ alkyl.
In some such embodiments, $R^{1G}$ is H, methyl, s-butyl, isobutyl, isopropyl, —$CH_2OH$, —$CH(Me)CH_2OH$, —$CH_2SH$, —$CH_2CH_2SMe$, —$CH_2phenyl$, —$CH_2(4$-hydroxyphenyl), —$CH_2$-(1H-indol-3-yl), —$CH_2$-(1H-imidazol-4-yl), —$CH_2C(O)OH$, —$CH_2CH_2C(O)OH$, —$CH_2$—C$(O)NH_2$, —$CH_2CH_2C(O)NH_2$, —$CH_2CH_2CH_2CH_2NH_2$ or —$CH_2CH_2CH_2NH(C$=$NH)NH_2$.
In some embodiments, $Ar^{1G}$ is unsubstituted phenyl.
In some embodiments, $Ar^{1G}$ is substituted phenyl. The phenyl can be substituted with 1, 2, 3, 4 or 5 substituents, e.g., 1, 2 or 3 substituents, e.g., 1 or 2 substituents, e.g. 1 substituent. The substituted phenyl can be a 4-hydroxyphenyl.
In some embodiments, $R^{1H}$ is H.
In some embodiments, $R^{1H}$ is $C_{1-6}$ alkyl.
In some embodiments $R^1$ is —$C(O)NR^{1C}R^{1D}$.
In some embodiments, $R^{1C}$ is H, $R^{1E}$, $C_{2-6}$ alkenyl, $C_{2-6}$ alkynyl, $Ar^1$ or $(C_{1-6}$ alkylene)$Ar^1$.
In some embodiments, $R^{1C}$ is H, $C_{1-6}$ alkyl, $(C_{1-6}$ alkylene)OH, $(C_{1-6}$ alkylene)O$(C_{1-6}$ alkyl), or $(C_{1-6}$ alkylene)$Ar^1$.
In some embodiments, $R^{1D}$ is H, $R^{1E}$, $C_{2-6}$ alkenyl, $C_{2-6}$ alkynyl, $Ar^1$ or $(C_{1-6}$ alkylene)$Ar^1$.
In some embodiments, $R^{1D}$ is H, $C_{1-6}$ alkyl, $(C_{1-6}$ alkylene)OH, $(C_{1-6}$ alkylene)O$(C_{1-6}$ alkyl), or $(C_{1-6}$ alkylene)$Ar^1$.
In some embodiments, $R^{1C}$ and $R^{1D}$, together with the N atom to which they are attached, form a 5-, 6-, or 7-membered heterocycloalkyl group, which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C$(=$NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{e1}S(O)R^{b1}$, $NR^{c1}S(O)_2R^{b1}$, $NR^{c1}S(O)_2NR^{c1}R^{d1}$, $S(O)R^{b1}$, $S(O)NR^{a1}R^{d1}$, $S(O)_2R^{b1}$, $S(O)_2NR^{c1}R^{d1}$, oxo, $Ar^1$, $(C_{1-6}$ alkylene)$Ar^1$ or $C(O)Ar^1$.

In some embodiment, $R^{1C}$ and $R^{1D}$, together form a group according to the formula —$(C_{2-3})$alkylene-Q-$(C_{1-3}$ alkylene)-, provided that $R^{1C}$ and $R^{1D}$, together with the N atom to which they are attached, form a 5-, 6-, or 7-membered ring; wherein Q is selected from a bond, —$CH_2$—, —CH$((C_1-C_6)$alkyl)-, —C$((C_1-C_6)$alkyl$)_2$-, —CHAr$^1$—, —C$((C_1-C_6)$alkyl)Ar$^1$—, —O—, —S—, —S(O)—, —S(O)$_2$—, —NH—, —N$((C_1-C_6)$alkyl)-, —NC(=O)$(C_1$-$C_6)$alkyl)-, —NAr$^1$—, —N$((C_{1-6}$ alkylene)Ar$^1)$— and —NC(=O)Ar$^1$.
In some such embodiments, Q can be selected from a bond, —$CH_2$—, —CH$((C_1-C_6)$alkyl)-, —C$((C_1-C_6)$alkyl$)_2$-, —O—, —S—, —S(O)—, —S(O)$_2$—, —NH—, —N$((C_1-C_6)$alkyl)- and —N$((C_{1-6}$ alkylene)Ar$^1)$—.
In some embodiment, $R^E$ is $C_{1-6}$ alkyl.
In some embodiments, $Ar^1$ is unsubstituted or substituted $C_{6-10}$ aryl.
In some embodiments, $Ar^1$ is 2,4-dihalo substituted phenyl. In some embodiments, $Ar^1$ is 2,4-difluorophenyl. In some embodiments, $Ar^1$ is 4-methoxyphenyl. In some embodiments, $Ar^1$ is 4-fluoro-2-(morpholin-4-yl)phenyl.
In some embodiments, $Ar^1$ is unsubstituted or substituted $C_{6-10}$ heteroaryl.
In some embodiments, $Ar^1$, when substituted, is substituted by 1, 2, 3, 4 or 5 substituents independently selected from $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C$(=$NR^{e1})$$NR^{c1}R^{d1}$, $NR^{c1}C$(=$NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$.
In some embodiments, $Ar^1$, when substituted, is substituted by 1, 2 or 3 substituents independently selected from $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C$(=$NR^{e1})$$NR^{c1}R^{d1}$, $NR^{c1}C$(=$NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $N^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$.
In some embodiments, $Ar^1$, when substituted, is substituted by 0 or 1 substituents selected from $Cy^1$.
In some embodiments, $R^1$ is 2,4-difluorophenylsulfonyl.
In some embodiments, $R^1$ is (4-methoxyphenyl)sulfonyl. In some embodiments, $R^1$ is 4-fluoro-2-(morpholin-4-yl)phenylsulfonyl.
In some embodiments, A is O.
In some embodiments, A is $S(O)_n$.
In some embodiments, n is 0.
In some embodiments, n is 1.
In some embodiments, n is 2.
In some embodiments, A is $NR^{2B}$.
In some embodiments, $R^{2A}$ is $C_{1-6}$ alkyl, $C_{2-6}$ alkenyl or $C_{2-6}$ alkynyl.
In some embodiments, $R^{2A}$ is $C_{1-6}$ alkyl, $C_{2-6}$ alkenyl or $C_{2-6}$ alkynyl.
In some embodiments, $R^{2A}$ is $Ar^2$.
In some embodiments, $R^{2A}$ is $(C_{1-6}$ alkylene)$Ar^2$.
In some embodiments, $R^{2A}$ is $CH_2Ar^2$.
In some embodiments, $R^{2A}$ A is other than a $C_{1-6}$ alkanesulfanyl group.
In some embodiments, $Ar^2$ is unsubstituted aryl.
In some embodiments, $Ar^2$ is unsubstituted phenyl.
In some embodiments, $Ar^2$ is substituted aryl.
In some embodiments, $Ar^2$ is phenyl substituted at least at the 4-position.

In some embodiments, $Ar^2$ is phenyl substituted at only the 4-position.

In some embodiments, $Ar^2$ is phenyl substituted at the 4-position by substituted or unsubstituted 5-10 membered heterocycloalkyl.

In some embodiments, $Ar^2$ is phenyl substituted at the 4-position by substituted or unsubstituted 5-10 membered heterocycloalkyl wherein the heterocycloalkyl is selected from piperazinyl, piperidinyl. In other embodiments, the heterocycloalkyl is morpholinyl.

In some embodiments, $Ar^2$ is phenyl substituted at the 4-position by substituted or unsubstituted 5-10 membered heterocycloalkyl wherein the heterocycloalkyl is selected from piperazin-1-yl, piperidin-4-yl. In other embodiments, the heterocycloalkyl is morpholin-4-yl.

In some embodiments, $Ar^2$ is phenyl substituted at the 4-position by 4-methylpiperazin-1-yl, 1-ethylpiperidin-4-yl and 1-methylpiperidin-4-yl. In other embodiments, $Ar^2$ is phenyl substituted at the 4-position by morpholine-4-yl.

In some embodiments, $Ar^2$ is unsubstituted heteroaryl.

In some embodiments, $Ar^2$ is substituted heteroaryl.

In some embodiments, $Ar^2$ indolyl or pyridyl.

In some embodiments, $Ar^2$ is indol-5-yl, indol-6-yl or 2-pyridyl. In some embodiments, $Ar^2$ is 1H-benzo[d]imidazol-2-yl. In some embodiments, $Ar^2$ is 1H-indazol-5-yl. In some embodiments, $Ar^2$ is 1H-benzo[d]imidazol-5-yl. In some embodiments, $Ar^2$ is quinolin-6-yl.

In some embodiments, $R^2$-A- is [4-(4-methylpiperazin-1-yl)phenyl]amino. $R^2$-A- is [4-(4-ethylpiperazin-1-yl)phenyl]amino. In some embodiments, $R^2$-A- is [2-methoxy-4-(4-methylpiperazin-1-yl)phenyl]amino. In some embodiments, $R^2$-A- is [4-(morpholin-4-yl)phenyl]amino. In some embodiments, $R^2$-A- is 4-methoxyphenylamino. In some embodiments, $R^2$-A- is benzylamino. In some embodiments, $R^2$-A- is (1H-indol-5-yl)amino. In some embodiments, $R^2$-A- is (1H-indol-6-yl)amino. In some embodiments, $R^2$-A- is [5-(4-methylpiperazin-1-yl)pyridin-2-yl]amino. In some embodiments, $R^2$-A- is -(1H-benzo[d]imidazol-2-yl)amino. In some embodiments, $R^2$-A- is (1H-indazol-5-yl)amino. In some embodiments, $R^2$-A- is (1H-benzo[d]imidazol-5-yl)amino. In some embodiments, $R^2$-A- is (quinolin-6-yl)amino.

In some embodiments, $R^{2B}$ is hydrogen.

In some embodiments, $R^{2B}$ is $C_{1-6}$ alkyl or $C(O)C_{1-6}$ alkyl.

In some embodiments, $R^{2B}$ is $Cy^{2A}$, $C(O)Cy^{2A}$, $(C_{1-6}$ alkylene$)Cy^{2A}$ or $C(O)(C_{1-6}$ alkylene$)Cy^{2A}$.

In some embodiments, $Cy^{2A}$ is unsubstituted or substituted aryl or unsubstituted or substituted heteroaryl.

In some embodiments, $Cy^{2A}$ is unsubstituted or substituted cycloalkyl or unsubstituted or substituted heterocycloalkyl.

In some embodiments, $R^{2A}$ and $R^{2B}$, together with the N atom to which they are attached, form a 5-, 6-, or 7-membered heterocycloalkyl group, which is unsubstituted or substituted by 1, 2, 3, 4 or 5 substituents independently selected from $R^{Cy2}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo.

In some embodiments, $R^{2A}$ and $R^{2B}$, together with the N atom to which they are attached, form a 5-membered ring, e.g., an unsubstituted or substituted pyrrolidine ring, e.g., pyrrolidine-1-yl.

In some embodiments, $R^{2A}$ and $R^{2B}$, together with the N atom to which they are attached, form a 6-membered ring, e.g., an unsubstituted or substituted piperidine, morpholine or piperazine ring, e.g., piperidin-1-yl, morpholine-4-yl, piperazine-1-yl, or 4-methylpiperazine-1-yl.

In some embodiments, $R^{2A}$ and $R^{2B}$, together with the N atom to which they are attached, form a 6-membered ring, e.g., an unsubstituted or substituted azepane ring, e.g., azepan-1-yl.

In some embodiments, $R^{3A}$ is H.

In some embodiments, $R^{3A}$ is $C_{1-6}$ alkyl, $C_{2-6}$ alkenyl, $C_{1-6}$ alkynyl.

In some embodiments, $R^{3A}$ is $C_{1-6}$ alkyl.

In some embodiments, $R^{3A}$ is methyl, ethyl, propyl, or isopropyl.

In some embodiments, $R^{3A}$ is methyl.

In some embodiments, $R^{3A}$ is $Cy^{3A1}$.

In some embodiments, $R^{3A}$ is $Cy^{3A1}$ wherein $Cy^{3A1}$ is $C_{3-7}$ cycloalkyl, which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$ $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$ $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$ $S(O)NR^{c3}R^{d3}$, $S(O)_2R^{b3}$, $S(O)_2 NR^{c3}R^{d3}$ and oxo.

In some embodiments, $R^{3A}$ is cyclopropyl, cyclobutyl, cyclopentyl, cyclohexyl or cycloheptyl.

In some embodiments, $R^{3A}$ is cyclopentyl.

In some embodiments, $R^{3A}$ is $Cy^{3A1}$ wherein $Cy^{3A1}$ is 5-10 membered heteroaryl, each of which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo.

In some embodiments, $R^{3A}$ is 1H-pyrazol-3-yl or 1-methyl-1H-pyrazol-3-yl. In some embodiments, $R^{3A}$ is 1-methyl-1H-pyrazol-3-yl.

In some embodiments, $R^{3A}$ is $(C_{1-6}$ alkylene$)Cy^{3A2}$.

In some embodiments, $R^{3A}$ is $(CH_2)_{1-6}Cy^{3A2}$.

In some embodiments, $R^{3A}$ is $(CH_2)Cy^{3A2}$.

In some embodiments, $Cy^{3A2}$ is $C_{3-7}$ cycloalkyl, which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo.

In some embodiments, $R^{3A}$ is $C_{3-7}$ cycloalkyl.

In some embodiments, $R^{3A}$ is $(C_{1-6}$ alkylene$)C_{3-7}$ cycloalkyl.

In some embodiments, $R^{3A}$ is $(CH_2)_{1-6}C_{3-7}$ cycloalkyl.

In some embodiments, $R^{3A}$ is $(CH_2)C_{3-7}$ cycloalkyl.

In some embodiments, $R^{3A}$ is cyclopropyl, cyclobutyl, cyclopentyl, cyclohexyl, cycloheptyl, cyclopropylmethyl, cyclobutylmethyl, cyclopentylmethyl, cyclohexylmethyl or cycloheptylmethyl.

In some embodiments, $R^{3B}$ is H.

In some embodiments, $R^{3B}$ is $C_{1-6}$ alkyl, $C_{2-6}$ alkenyl or $C_{1-6}$ alkynyl.

In some embodiments, $R^{3B}$ is $C_{1-6}$ alkyl.

In some embodiments, $R^{3B}$ is methyl or ethyl.

In some embodiments, $R^{3A}$ and $R^{3B}$, together with the N atom to which they are attached, form a 5-, 6-, or 7-membered heterocycloalkyl group, which is unsubstituted or substituted by 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^3C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo.

In some embodiments, $R^{3A}$ and $R^{3B}$, together with the N atom to which they are attached, form a 5-, 6-, or 7-membered heterocycloalkyl group, which is unsubstituted.

In some embodiments, $R^{3A}$ and $R^{3B}$, together with the N atom to which they are attached, form a pyrrolidinyl, piperidinyl, azepanyl or morpholinyl group.

In some embodiments, any one or more of $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$ and $R^{d4}$ can be independently selected from H and $C_{1-6}$ alkyl.

In some embodiments, each of $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$ and $R^{d4}$ can be independently selected from H and $C_{1-6}$ alkyl.

In some embodiments, any one or more of $R^{e1}$, $R^{e2}$, $R^{e3}$ and $R^{e4}$ is H.

In some embodiments, each of $R^{e1}$, $R^{e2}$, $R^{e3}$ and $R^{e4}$ is H.

In some embodiments, the compound of formula (I) is selected from the following compounds, and salts thereof:

3-[4-Amino-2-(methylsulfanyl)pyrimidin-5-yl]acrylonitrile;
3-[4-Methylamino-2-(methylsulfanyl)pyrimidin-5-yl]acrylonitrile;
3-[4-Ethylamino-2-(methylsulfanyl)pyrimidin-5-yl]acrylonitrile;
3-[4-Propylamino-2-(methylsulfanyl)pyrimidin-5-yl]acrylonitrile;
3-[4-Isopropylamino-2-(methylsulfanyl)pyrimidin-5-yl]acrylonitrile;
3-[4-(Cyclopropylmethyl)amino-2-(methylsulfanyl)pyrimidin-5-yl]-acrylonitrile;
3-[4-Cyclopropylamino-2-(methylsulfanyl)pyrimidin-5-yl]acrylonitrile;
3-[4-Cyclopentylamino-2-(methylsulfanyl)pyrimidin-5-yl]acrylonitrile;
3-[4-Cyclohexylamino-2-(methylsulfanyl)pyrimidin-5-yl]acrylonitrile;
3-[4-(N-Ethyl-N-methylamino)-2-(methylsulfanyl)pyrimidin-5-yl]acrylonitrile;
3-[2-Methylsulfanyl-4-(pyrrolidin-1-yl)pyrimidin-5-yl]acrylonitrile;
3-[4-(N-Cyclopentyl-N-ethylamino)-2-(methylsulfanyl)pyrimidin-5-yl]acrylonitrile;
5-{2-[(2,4-Difluorophenyl)sulfonyl]vinyl}-N-methyl-2-(methylsulfanyl)pyrimidin-4-amine;
N-Cyclopentyl-5-{2-[(2,4-difluorophenyl)sulfonyl]vinyl}-2-(methylsulfanyl)pyrimidin-4-amine;
3-[4-Amino-2-(methylsulfinyl)pyrimidin-5-yl]acrylonitrile;
3-[4-Methylamino-2-(methylsulfinyl)pyrimidin-5-yl]acrylonitrile;
3-[4-Ethylamino-2-(methylsulfinyl)pyrimidin-5-yl]acrylonitrile;
3-[4-Propylamino-2-(methylsulfinyl)pyrimidin-5-yl]acrylonitrile;
3-[4-Isopropylamino-2-(methylsulfinyl)pyrimidin-5-yl]acrylonitrile;
3-[4-(Cyclopropylmethyl)amino-2-(methylsulfinyl)pyrimidin-5-yl]-acrylonitrile;
3-[4-Cyclopropylamino-2-(methylsulfinyl)pyrimidin-5-yl]acrylonitrile;
3-[4-Cyclopentylamino-2-(methylsulfinyl)pyrimidin-5-yl]acrylonitrile;
3-[4-Cyclohexylamino-2-(methylsulfinyl)pyrimidin-5-yl]acrylonitrile
3-[4-(N-Ethyl-N-methylamino)-2-(methylsulfinyl)pyrimidin-5-yl]acrylonitrile;
3-[2-Methylsulfinyl-4-(pyrrolidin-1-yl)pyrimidin-5-yl]acrylonitrile;
3-[4-(N-Cyclopentyl-N-ethylamino)-2-(methylsulfinyl)pyrimidin-5-yl]acrylonitrile;
5-{2-[(2,4-Difluorophenyl)sulfonyl]vinyl}-N-methyl-2-(methylsulfinyl)pyrimidin-4-amine; and
N-Cyclopentyl-5-{2-[(2,4-difluorophenyl)sulfinyl]vinyl}-2-(methylsulfinyl)pyrimidin-4-amine.

In some embodiments, the compound of formula (I) is selected from the following compounds, and salts thereof:

3-{4-Amino-2-[4-(4-methylpiperazin-1-yl)phenylamino]pyrimidin-5-yl}acrylonitrile;
3-{4-Methylamino-2-[4-(4-methylpiperazin-1-yl)-phenylamino]pyrimidin-5-yl}acrylonitrile;
3-{4-Ethylamino-2-[4-(4-methylpiperazin-1-yl)phenylamino]pyrimidin-5-yl}acrylonitrile;
3-{4-Propylamino-2-[4-(4-methylpiperazin-1-yl)phenylamino]pyrimidin-5-yl}acrylonitrile;
3-{4-Isopropylamino-2-[4-(4-methylpiperazin-1-yl)phenylamino]pyrimidin-5-yl}acrylonitrile;
3-{4-(Cyclopropylmethyl)amino-2-[4-(4-methylpiperazin-1-yl)phenylamino]pyrimidin-5-yl}acrylonitrile;
3-{4-Cyclopropylamino-2-[4-(4-methylpiperazin-1-yl)phenylamino]pyrimidin-5-yl}acrylonitrile;
3-{4-Cyclopentylamino-2-[4-(4-methylpiperazin-1-yl)phenylamino]pyrimidin-5-yl}acrylonitrile;
3-{4-Cyclohexylamino-2-[4-(4-methylpiperazin-1-yl)phenylamino]pyrimidin-5-yl}acrylonitrile;
3-{4-Cyclopentylamino-2-[(4-morpholin-4-yl)phenylamino]pyrimidin-5-yl}acrylonitrile;
3-[4-Cyclopentylamino-2-(1H-indol-5-ylamino)pyrimidin-5-yl]acrylonitrile;
3-{4-Cyclopentylamino-2-[4-(1-methylpiperidin-4-yl)phenylamino]pyrimidin-5-yl}acrylonitrile;
3-[2-(1H-Indol-5-ylamino)-4-(methylamino)pyrimidin-5-yl]acrylonitrile;
3-{4-(Cyclopentylamino)-2-[(4-methoxyphenyl)amino]pyrimidin-5-yl)acrylonitrile;
3-{4-Cyclopentylamino-2-[4-(1-ethylpiperazin-4-yl)-phenylamino]-pyrimidin-5-yl}acrylonitrile;
3-[2-(Benzylamino)-4-(cyclopentylamino)pyrimidin-5-yl]acrylonitrile;
3-(4-(Cyclopentylamino)-2-((5-(4-methylpiperazin-1-yl)pyridin-2-yl)amino)pyrimidin-5-yl)acrylonitrile;
3-{4-(Cyclopentylamino)-2-[(4-methoxyphenyl)amino]pyrimidin-5-yl)acrylonitrile;
3-{4-[(Cyclopropylmethyl)amino]-2-[4-(4-ethylpiperazin-1-yl)phenylamino]pyrimidin-5-yl}acrylonitrile;
3-{4-[(Cyclopropylmethyl)amino]-2-[(1H-indol-5-yl)amino]pyrimidin-5-yl)acrylonitrile;
3-{4-(N-Ethyl-N-methylamino)-2-[4-(4-methylpiperazin-1-yl)phenylamino]pyrimidin-5-yl}acrylonitrile;
3-{2-[4-(4-methylpiperazin-1-yl)phenylamino]-4-(pyrrolidin-1-yl)pyrimidin-5-yl}acrylonitrile;
3-{4-(N-Cyclopentyl-N-ethylamino)-2-[4-(4-methylpiperazin-1-yl)phenylamino]pyrimidin-5-yl}acrylonitrile;

3-{4-[N-(Cyclopropylmethyl)-N-ethylamino]-2-[4-(morpholin-4-yl)phenylamino]pyrimidin-5-yl}acrylonitrile;

N-[5-(2-Cyanovinyl)-4-(cyclopentylamino)pyrimidin-2-yl]-N-[4-(4-methylpiperazin-1-yl)phenyl]-5-((3aS,4S,6aR)-2-oxohexahydro-1H-thieno[3,4-d]imidazol-4-yl)pentanamide;

5-{2-[2,4-(Difluorophenyl)sulfonyl]vinyl}-$N^2$-(1H-indol-5-yl)-$N^4$-methylpyrimidine-2,4-diamine;

$N^4$-Cyclopentyl-5-{2-[(2,4-difluorophenyl)sulfonyl]vinyl}-$N^2$-[4-(4-methylpiperazin-1-yl)phenyl]pyrimidine-2,4-diamine; and 5-{2-[2,4-(Difluorophenyl)sulfonyl]vinyl}-$N^2$-(1H-indol-6-yl)-$N^4$-methylpyrimidine-2,4-diamine.

In some embodiments, the compound of formula (I) is selected from the following compounds, and salts thereof:

N-Methyl-2-(methylsulfanyl)-5-(2-nitrovinyl)pyrimidin-4-amine;

N-Methyl-2-(methylsulfinyl)-5-(2-nitrovinyl)pyrimidin-4-amine;

$N^4$-Methyl-$N^2$-[4-(4-methylpiperazin-1-yl)phenyl]-5-(2-nitrovinyl)pyrimidine-2,4-diamine;

N-Cyclopentyl-2-(methylsulfanyl)-5-(2-nitrovinyl)pyrimidin-4-amine;

N-Cyclopentyl-2-(methylsulfinyl)-5-(2-nitrovinyl)pyrimidin-4-amine;

$N^4$-Cyclopentyl-$N^2$-[4-(4-methylpiperazin-1-yl)phenyl]-5-(2-nitrovinyl)pyrimidine-2,4-diamine;

3-(4-(Methylamino)-2-{[4-(4-methylpiperazin-1-yl)phenyl]amino}pyrimidin-5-yl)acrylic acid;

3-(4-(Cyclopentylamino)-2-{[4-(4-methylpiperazin-1-yl)phenyl]amino}pyrimidin-5-yl)acrylic acid;

4-[4-(Methylamino)-2-(methylsulfanyl)pyrimidin-5-yl]but-3-en-2-one;

4-[4-(Methylamino)-2-(methylsulfinyl)pyrimidin-5-yl]but-3-en-2-one;

4-(4-(methylamino)-2-{[4-(4-methylpiperazin-1-yl)phenyl]amino}pyrimidin-5-yl)but-3-en-2-one;

4-[4-(Cyclopentylamino)-2-(methylsulfanyl)pyrimidin-5-yl]but-3-en-2-one;

4-[4-(Cyclopentylamino)-2-(methylsulfinyl)pyrimidin-5-yl]but-3-en-2-one;

4-(4-(Cyclopentylamino)-2-{[4-(4-methylpiperazin-1-yl)phenyl]amino}pyrimidin-5-yl)but-3-en-2-one;

3-[4-(Cyclopentylamino)-2-morpholinopyrimidin-5-yl]acrylonitrile;

3-{4-[(1-Methyl-1H-pyrazol-3-yl)amino]-2-(methylsulfanyl)pyrimidin-5-yl}acrylonitrile;

3-{4-[(1-Methyl-1H-pyrazol-3-yl)amino]-2-(methylsulfinyl)pyrimidin-5-yl}acrylonitrile;

3-(4-[(1-Methyl-1H-pyrazol-3-yl)amino]-2-{[4-(4-methylpiperazin-1-yl)phenyl]amino}pyrimidin-5-yl)acrylonitrile;

3-[4-(Cyclopentylamino)-2-{[2-methoxy-4-(4-methylpiperazin-1-yl)phenyl]amino}pyrimidin-5-yl]acrylonitrile;

5-{2-[(2,4-Difluorophenyl)sulfonyl]vinyl}-$N^4$-methyl-$N^2$-[4-(4-methylpiperazin-1-yl)phenyl]pyrimidine-2,4-diamine;

5-{2-[(2,4-Difluorophenyl)sulfonyl]vinyl}-$N^2$-methyl-$N^2$-(4-morpholinophenyl)pyrimidine-2,4-diamine;

5-{2-[(2,4-Difluorophenyl)sulfonyl]vinyl}-$N^2$-(4-methoxyphenyl)-$N^4$-methylpyrimidine-2,4-diamine;

5-{2-[(2,4-Difluorophenyl)sulfonyl]vinyl}-$N^4$-methyl-$N^2$-(3,4,5-trimethoxyphenyl)pyrimidine-2,4-diamine;

$N^2$-(1H-Benzo[d]imidazol-2-yl)-5-{2-[(2,4-difluorophenyl)sulfonyl]vinyl}-$N^4$-methylpyrimidine-2,4-diamine;

5-{2-[(2,4-Difluorophenyl)sulfonyl]vinyl}-$N^2$-(1H-indazol-5-yl)-$N^4$-methylpyrimidine-2,4-diamine;

N-Cyclopentyl-5-(2-((4-methoxyphenyl)sulfonyl)vinyl)-2-(methylsulfanyl)pyrimidin-4-amine;

N-Cyclopentyl-5-{2-[(4-methoxyphenyl)sulfonyl]vinyl}-2-(methylsulfinyl)pyrimidin-4-amine;

$N^4$-Cyclopentyl-5-{2-[(4-methoxyphenyl)sulfonyl]vinyl}-$N^2$-[4-(4-methylpiperazin-1-yl)phenyl]pyrimidine-2,4-diamine;

$N^4$-Cyclopentyl-$N^2$-(1H-indol-5-yl)-5-{2-[(4-methoxyphenyl)sulfonyl]vinyl}pyrimidine-2,4-diamine;

5-{2-[(2,4-Difluorophenyl)sulfonyl]vinyl}-$N^4$-methyl-$N^2$-[5-(4-methylpiperazin-1-yl)pyridin-2-yl]pyrimidine-2,4-diamine;

$N^4$-Cyclopentyl-$N^2$-(4-methoxyphenyl)-5-{2-[(4-methoxyphenyl)sulfonyl]vinyl}pyrimidine-2,4-diamine;

$N^2$-(1H-Benzo[d]imidazol-5-yl)-5-{2-[(2,4-difluorophenyl)sulfonyl]vinyl}-$N^4$-methylpyrimidine-2,4-diamine;

N-Cyclopentyl-5-{2-[(4-methoxyphenyl)sulfonyl]vinyl}-2-morpholinopyrimidin-4-amine;

N-Cyclopentyl-5-{2-[(4-fluoro-2-morpholinophenyl)sulfonyl]vinyl}-2-morpholinopyrimidin-4-amine;

5-{2-[(4-Methoxyphenyl)sulfonyl]vinyl}-N-(1-methyl-1H-pyrazol-3-yl)-2-(methylsulfanyl)pyrimidin-4-amine;

5-{2-[(4-Methoxyphenyl)sulfonyl]vinyl}-N-(1-methyl-1H-pyrazol-3-yl)-2-(methylsulfinyl)pyrimidin-4-amine;

5-{2-[(4-Methoxyphenyl)sulfonyl]vinyl}-$N^4$-(1-methyl-1H-pyrazol-3-yl)-$N^2$-[4-(4-methylpiperazin-1-yl)phenyl]pyrimidine-2,4-diamine;

5-{2-[(2,4-Difluorophenyl)sulfonyl]vinyl}-$N^4$-(1-methyl-1H-pyrazol-3-yl)-2-(methylsulfanyl)pyrimidin-4-amine;

5-{2-[(2,4-Difluorophenyl)sulfonyl]vinyl}-N-(1-methyl-1H-pyrazol-3-yl)-2-(methylsulfinyl)pyrimidin-4-amine;

5-{2-[(2,4-Difluorophenyl)sulfonyl]vinyl}-N-(1-methyl-1H-pyrazol-3-yl)-$N^2$-[4-(4-methylpiperazin-1-yl)phenyl]pyrimidine-2,4-diamine;

5-{2-[(2,4-Difluorophenyl)sulfonyl]vinyl}-$N^2$-(1H-indol-5-yl)-$N^4$-(1-methyl-1H-pyrazol-3-yl)pyrimidine-2,4-diamine;

5-{2-[(2,4-Difluorophenyl)sulfonyl]vinyl}-$N^4$-(1-methyl-1H-pyrazol-3-yl)-$N^2$-(4-morpholinophenyl)pyrimidine-2,4-diamine;

5-{2-[(2,4-Difluorophenyl)sulfonyl]vinyl}-$N^4$-(1-methyl-1H-pyrazol-3-yl)-$N^2$-(quinolin-6-yl)pyrimidine-2,4-diamine;

3-(4-(Cyclopentylamino)-2-(methylsulfanyl)pyrimidin-5-yl)acrylic acid ethyl ester;

3-(4-(Cyclopentylamino)-2-(methylsulfinyl)pyrimidin-5-yl) acrylic acid ethyl ester; and 3-[4-(Cyclopentylamino)-2-{[4-(4-methylpiperazin-1-yl)phenyl]amino}pyrimidin-5-yl]acrylic acid ethyl ester.

In some embodiments, the —CH═CH—$R^1$ group of the compounds described above, or any of the embodiments thereof, has (E)-stereochemistry, which is preferred.

In some embodiments, the —CH═CH—$R^1$ group of the compounds described above, or any of the embodiments thereof, has (Z)-stereochemistry.

The features of the compounds described above which are, for clarity, described in the context of separate embodiments, can also be provided in combination in a single embodiment.

Conversely, various features described herein which are, for brevity, described in the context of a single embodiment, can also be provided separately or in any suitable subcombination.

III. Synthesis

Compounds provided herein, including salts thereof, can be prepared using known organic synthesis techniques and can be synthesized according to any of numerous possible synthetic routes.

The reactions for preparing compounds as described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, e.g., in *Protecting Group Chemistry*, 1$^{st}$ Ed., Oxford University Press, 2000; *March's Advanced Organic chemistry: Reactions, Mechanisms, and Structure*, 5$^{th}$ Ed., Wiley-Interscience Publication, 2001; and Petursson et al., "*Protecting Groups in Carbohydrate Chemistry,*" *J. Chem. Educ.*, 1997, 74(11), 1297.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" Blom, et al., *J. Combi. Chem.* 2004, 6(6) 874-883 and normal phase silica chromatography, Still et al., *J. Org. Chem.*, 1978, 43(14), 2923-25.

Compounds of formula (I), including embodiments thereof, can be prepared using a compound of formula (II) as a starting material:

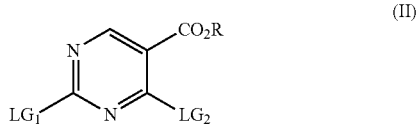

(II)

wherein $CO_2R$ represents a suitable ester group, e.g., an alkyl ester, e.g. a methyl or ethyl ester and $LG_1$ and $LG_2$ represent leaving groups, e.g., halo groups, e.g., chlorine.

The compound of formula (II) can be converted to a compound of formula (I) by a reaction scheme as illustrated in Scheme 1 incorporating, e.g., the following steps:

(1) reacting with a suitable amine compound of formula NHR$^{3A}$R$^{3B}$ to introduce the group —NR$^{3A}$R$^{3B}$ (by nucleophilic substitution of the leaving group $LG_2$);

(2) reacting with a suitable amine, hydroxy or mercapto compound of formula R$^{2A}$-AH (wherein A is NR$^{2B}$, O or S) (by nucleophilic substitution of the leaving group $LG_1$); and (3) converting the ester group to an aldehyde group followed by a suitable alkene-forming reaction to introduce the CH=CHR$^1$ group.

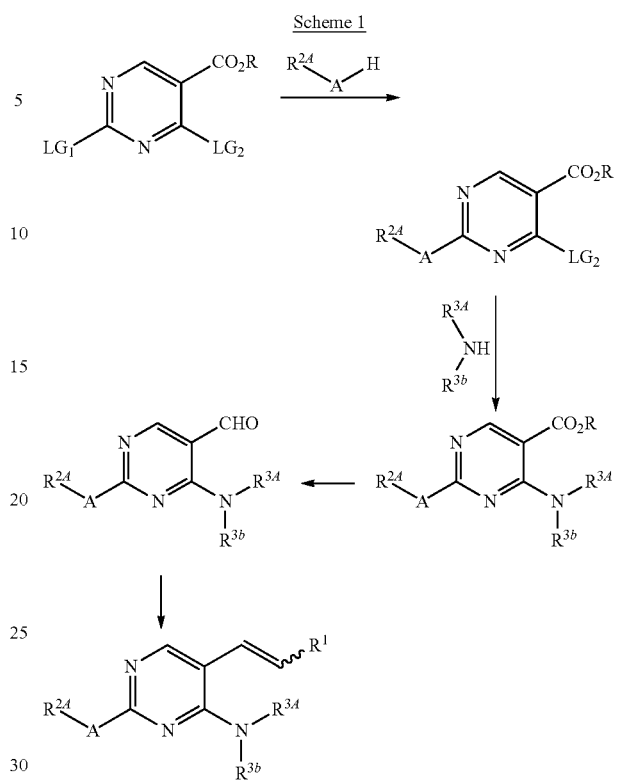

The nucleophilic substitution reactions performed to introduce the groups —NR$^{3A}$R$^{3B}$; or R$^{2A}$-A- can be carried out, e.g., by reacting in the presence of the compound of formula NHR$^{3A}$R$^{3B}$ or the compound of formula R$^{2A}$-AH. The nucleophilic displacement reaction can be promoted by heating, or by the presence of a base, or both. In addition, nucleophilic displacement by alkoxide can be promoted by the presence of copper (I) oxide, while nucleophilic displacement by amino compounds can be promoted by the presence of an organometallic catalyst, e.g., using Buchwald-Hartwig cross-coupling conditions.

Compounds of formula (I), or intermediate compounds, wherein A is S (i.e., a thioether) can be converted to compounds wherein A is S(O) (i.e., a sulfoxide) or S(O)$_2$ (i.e., a sulfone) by reacting the thioether with a suitable oxidizing agent under suitable conditions. Suitable oxidizing agents include, e.g., hydrogen peroxide, peroxyacid compounds (e.g., mCPBA), and potassium peroxymonosulfate. Reaction under mild conditions in the presence of 1 equiv. of the oxidizing agent produces a sulfoxide, whereas reaction in the presence of excess oxidizing agent produces a sulfone.

Conversion of the ester group to an aldehyde can be performed either by performing a selective reduction of the ester group to an aldehyde using a suitable selective reducing agent (e.g., diisobutylaluminum hydride) or by reducing the ester group to a primary alcohol (e.g., using lithium aluminum hydride), followed by oxidation of the alcohol to an aldehyde (e.g., using manganese dioxide). Further examples of reagents suitable for effecting such transformations are described, e.g., in Larock, *Comprehensive Organic Transformations: A Guide to Functional Group Preparations*, 2$^{nd}$ Ed. (Wiley 1999).

Conversion of the aldehyde to an alkene can be performed either by performing a suitable alkene-forming condensation reaction, for example as shown in Scheme 1. An aldehyde of formula (III) can be reacted under basic conditions with a compound of formula (IV-A) to effect formation of a C=C bond via deprotonation of the compound of formula (IV-A) followed by nucleophilic reaction of the resulting anion with the aldehyde, following by dehydration of the resulting intermediate. In the Scheme shown below, a suitable precursor group (e.g., a suitable leaving group, $LG_1$ or $LG_2$, or a precursor thereof) can be used in place of the -A-$R^{2A}$ group or —$NR^{3A}R^{3B}$ group. In addition, a suitable functional group can be included in the compound of formula (IV), e.g., a silyl group (see compound IV-B), or a phosphine or phosphonate group (compound IV-C and IV-D) to effect alkene formation via a Peterson, Wittig, or Wadsworth-Emmons-type olefination reaction.

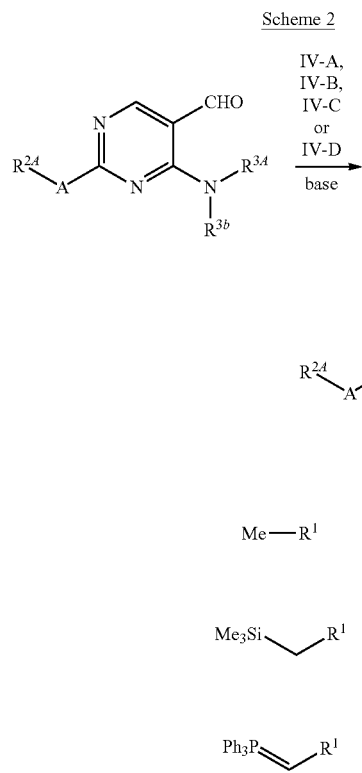

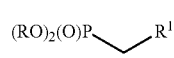

In a variant of the procedure shown above, when $R^1$ is a carbonyl group (aldehyde, ketone or carboxylic acid or ester) the condensation can be carried out with a carboxylic acid derivative followed by decarboxylation of the intermediate dicarbonyl compound as illustrated in

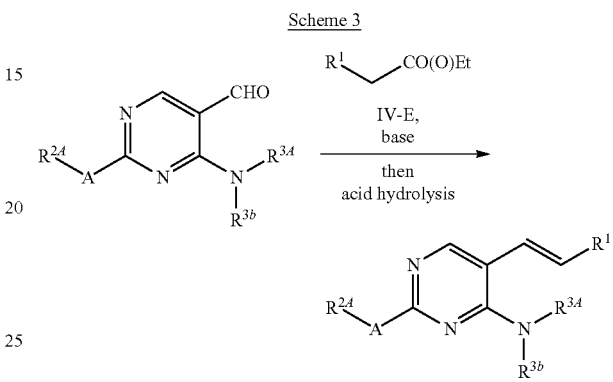

An illustrative method for preparing compounds of formula (I) wherein $R^1$ is CN and A is $NR^{2B}$ is shown in Scheme 4 below. In the synthetic route shown in Scheme 4, the known compound (1) is reacted with an appropriate amine to prepare a compound of formula (2) by nucleophilic substitution of the chloro group of compound (1). The resulting compound of formula (2) is then reduced to the substituted methanol compound (3), which is then oxidized to the aldehyde of formula (4). Alternatively, a compound of formula (4) can be prepared by nucleophilic of a suitably substituted aldehyde such as the compound of formula (5). The compound of formula (4) is then subjected to an olefination reaction to provide the acrylonitrile compound (5). Finally, an amino group is introduced at the 2-position of the pyrimidine ring by activating the thioether group as a leaving group via oxidation to a sulfoxide (6), allowing the second amine substituent to be introduced into compound (7) via nucleophilic substitution of the sulfoxide group.

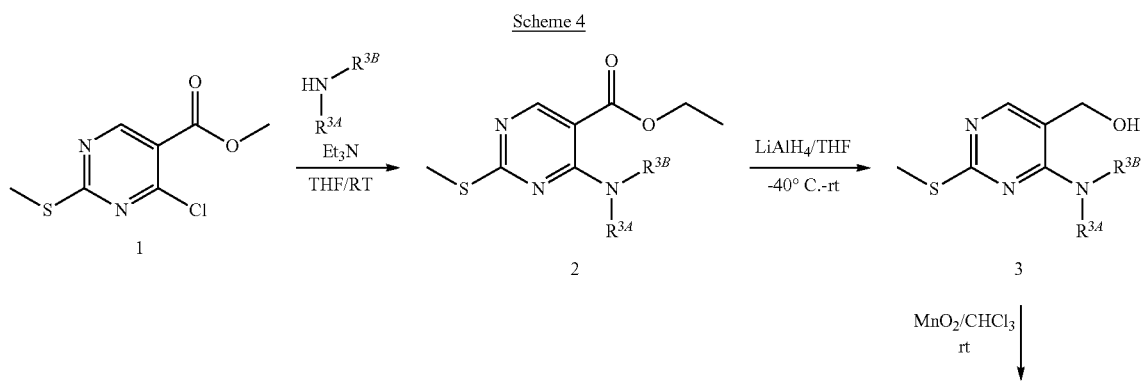

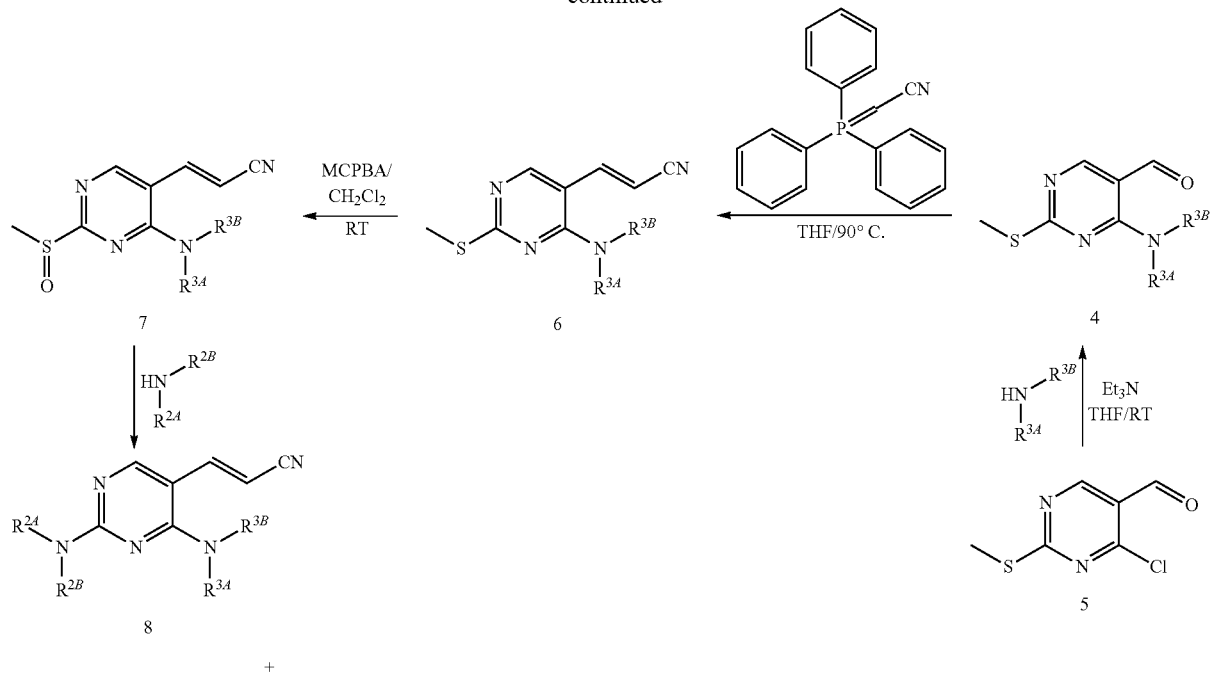

An illustrative method for preparing compounds of formula (I) wherein $R^1$ is $S(O)_2Ar^1$ and A is $NR^{2B}$ is shown in Scheme 5 below. In the synthetic route shown in Scheme 5, the thiol (9) is reacted with the known compound (10) to prepare a compound of formula (11) by nucleophilic substitution of the iodo group of compound (10). The resulting compound of formula (11) is then oxidized to a sulfone compound of formula (12), which is then reacted with an aldehyde of formula (4) in an olefination reaction to provide the vinylic sulfone compound (13). Finally, the amino group is introduced at the 2-position as described above by activating the thioether group as a leaving group via oxidation to a sulfoxide (14), allowing the second amine substituent to be introduced into compound (15) via nucleophilic substitution of the sulfoxide group. Analogous schemes can be used to introduce other groups of formula $S(O)_jAr^1$ or $S(O)_k(C_{1-6}\text{ alkylene})Ar^1$.

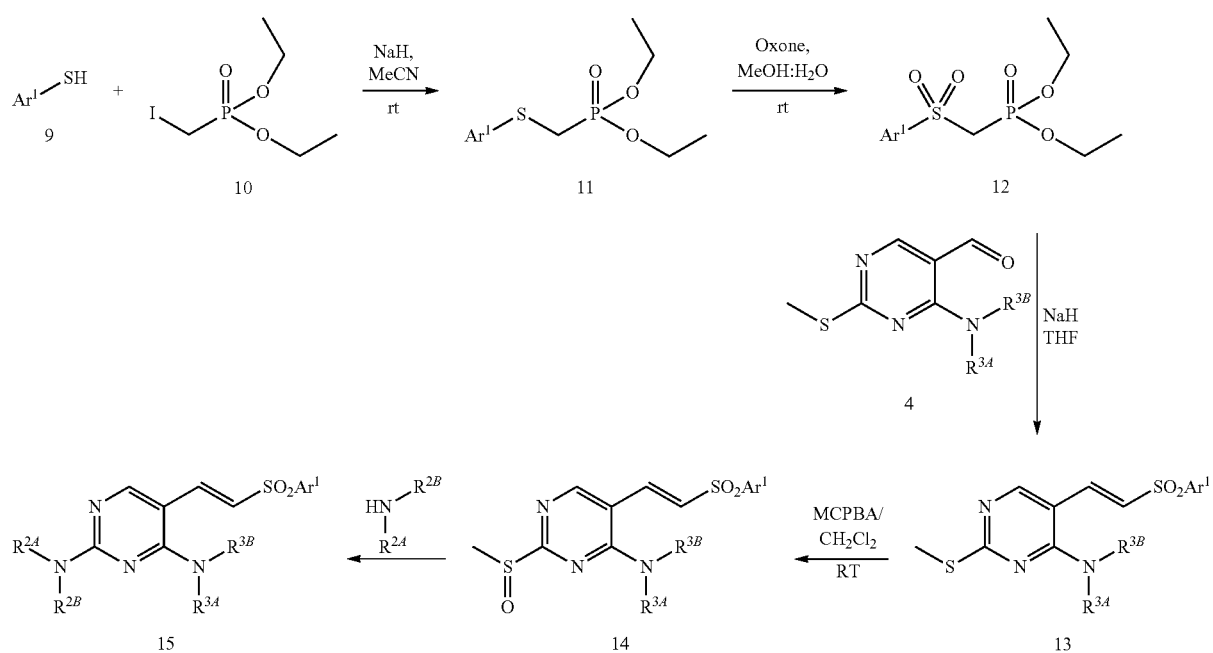

Schemes that can be used to prepare other compounds according to formula (I) are shown in Schemes 6 to 11 below:
Scheme 6
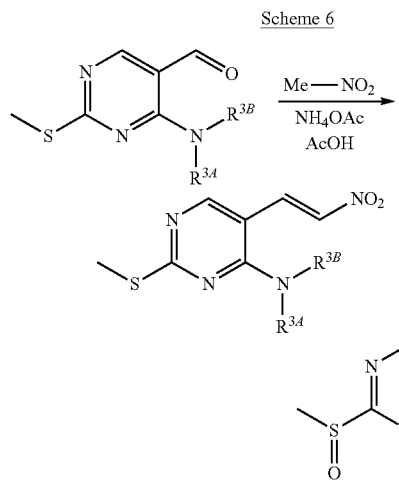
Scheme 7
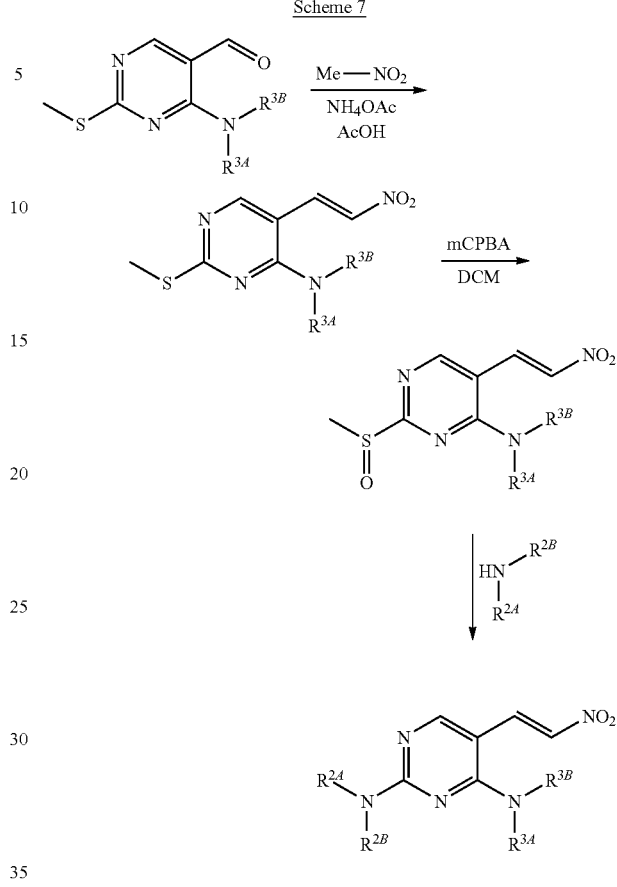
Scheme 8
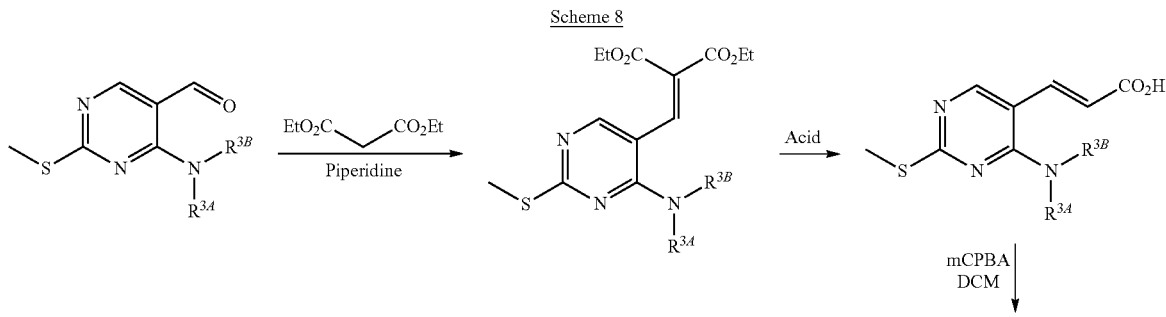
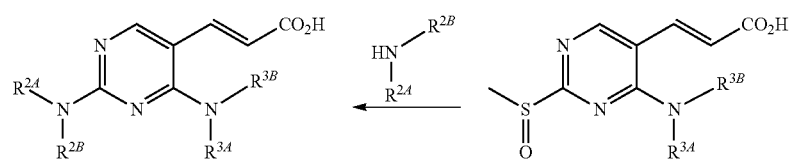

Scheme 9
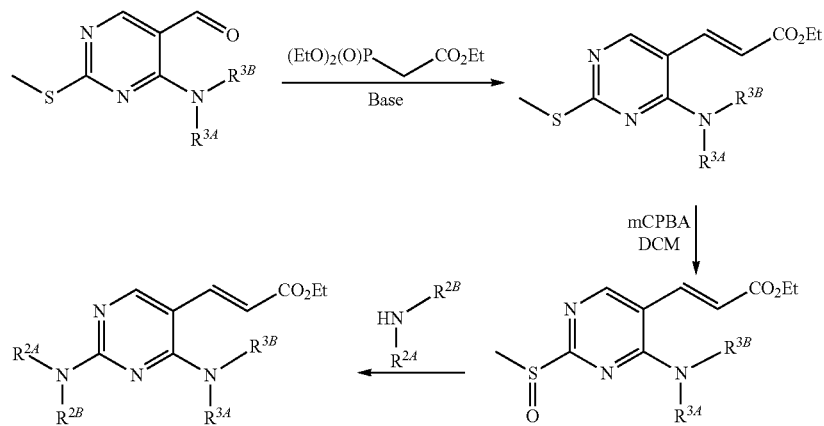
Scheme 10
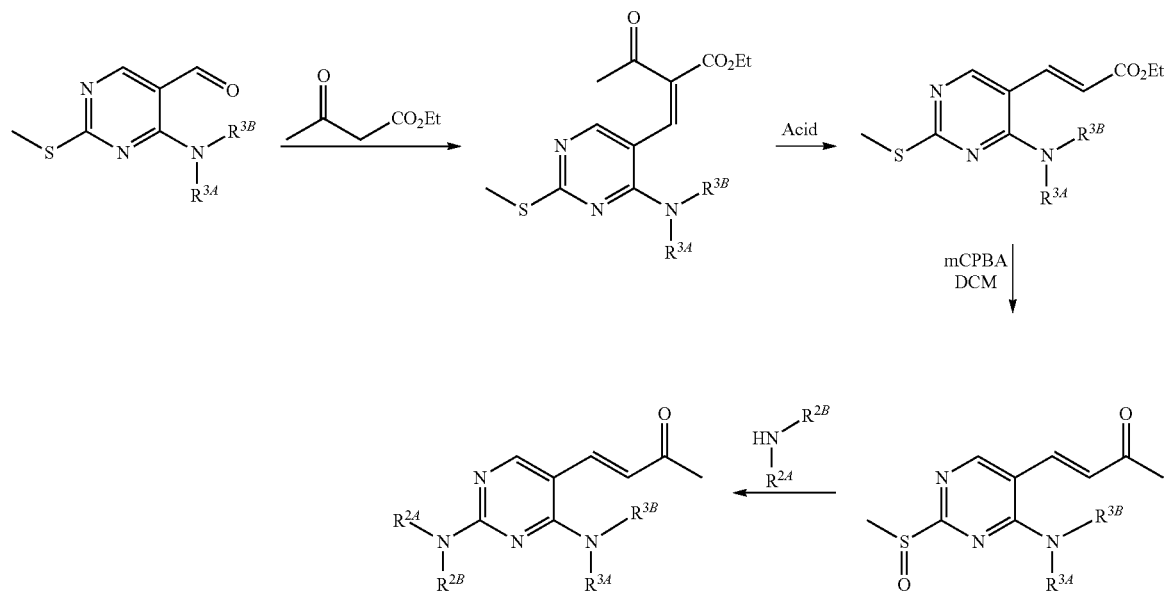
Scheme 11
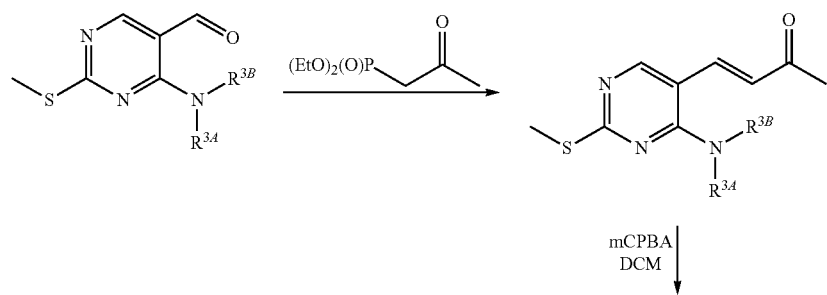

-continued

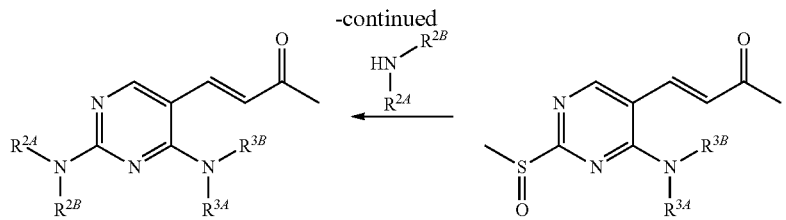

The foregoing methods may provide predominantly the (E)-stereoisomer, predominantly the (Z)-stereoisomer, or a mixture of stereoisomers. The geometric isomers can be separated, interconverted, or equilibrated by methods known to a person skilled in the art. Generally, the (E)-isomer is more stable and the major product in alkene forming reactions that are under thermodynamic control. Methods for stereoselective synthesis of (Z)-alkenes are reviewed by Siau et al., *Top. Curr. Chem.*, 2012, 327, 33-58. For additional methods of preparing (Z)-alkenes see Still et al., Tetrahedron Lett., 1983, 24, 4405-08 and Messik et al., *Synthesis*, 2013, 45(2), 167-170.

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn and C. W. Rees (Pergamon Press, 1996), *Comprehensive Organic Functional Group Transformations II*, Ed. A. R. Katritzky and R. J. K. Taylor (Editor) (Elsevier, 2$^{nd}$ Edition, 2004), *Comprehensive Heterocyclic Chemistry*, Ed. A. R. Katritzky and C. W. Rees (Pergamon Press, 1984) and *Comprehensive Heterocyclic Chemistry II*, Ed. A. R. Katritzky, C. W. Rees and E. F. V. Scriven (Pergamon Press, 1996).

IV. Pharmaceutical Formulations and Dosage Forms

When employed as pharmaceuticals, the compounds described herein can be administered in the form of pharmaceutical compositions, in which an active ingredient is combined with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

These compositions can be prepared in a manner well known in the pharmaceutical art and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners, and the like, may be necessary or desirable.

This disclosure also includes pharmaceutical compositions which contain, as the active ingredient, a compound as described herein or a pharmaceutically acceptable salt thereof, in combination with one or more pharmaceutically acceptable carriers (excipients). In some embodiments, the composition is suitable for topical administration. In making the compositions described herein, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, an active compound can be milled to provide the appropriate particle size prior to combining with the other ingredients. If an active compound is substantially insoluble, it can be milled to a particle size of less than 200 mesh. If an active compound is substantially water soluble, the particle size can be adjusted by milling to provide a substantially uniform distribution in the formulation, e.g. about 40 mesh.

The compounds described herein may be milled using known milling procedures such as wet milling to obtain a particle size appropriate for tablet formation and for other formulation types. Finely divided (nanoparticulate) preparations of the compounds described herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions described herein contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions described herein contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 300 to about 350, about 350 to about 400, or about 450 to about 500 mg of the active ingredient.

In some embodiments, the compositions described herein contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages of the compounds described herein may be used in the methods and uses described below.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound as described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient.

The tablets or pills described herein can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerine monostearate, PEG-glycerine monostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2, or at least about 5 wt % of the compound as described herein. The topical formulations can be suitably packaged in tubes of, e.g., 100 g which are optionally associated with instructions for the treatment of the select indication.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound described herein can vary according to, e.g., the particular use for which the treatment is made, the manner of administration of the compound, the health and condition of the patient, and the judgment of the prescribing physician. The proportion or concentration of a compound in a pharmaceutical composition can vary depending upon a number of factors including dosage, chemical characteristics (e.g., hydrophobicity), and the route of administration. For example, the compounds as described herein can be provided in an aqueous physiological buffer solution containing about 0.1 to about 10% w/v of the compound for parenteral administration. Some typical dose ranges are from about 1 mg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Methods of Use

Provided herein are methods of treating a cellular proliferative disorder in a patient. The method includes administering to the patient a therapeutically effective amount of a compound of formula (I), or a pharmaceutically acceptable salt thereof, or any of the embodiments thereof.

A "cellular proliferative disorder" means a disorder wherein cells are made by the body at an atypically accelerated rate. The expression "kinase-dependent proliferative disorder" refers to a proliferative disorder wherein the abnormally high cell proliferation is driven by the expression of a protein kinase.

A cellular proliferative disorder can include cancer. Non-limiting examples of cancers include bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer and testicular cancer.

More particularly, cancers that may be treated by the compound, compositions and methods described herein include, but are not limited to, the following:

1) Breast cancers, including, e.g., $ER^+$ breast cancer, $ER^-$ breast cancer, $her2^-$ breast cancer, $her2^+$ breast cancer, stromal tumors such as fibroadenomas, phyllodes tumors and sarcomas and epithelial tumors such as large duct papillomas; carcinomas of the breast including in situ (non-invasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and $her2$ negative ($her2^-$). In some embodiments, the breast cancer may have a high risk Oncotype score.

2) Cardiac cancers, including, e.g., sarcoma, e.g., angiosarcoma, fibrosarcoma, rhabdomyosarcoma, and liposarcoma; myxoma; rhabdomyoma; fibroma; lipoma and teratoma.

3) Lung cancers, including, e.g., bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, e.g., cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, e.g., cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, e.g., hepatoma, e.g., hepatocellular carcinoma; cholangiocarcinoma; hepatoblastoma; angiosarcoma; hepatocellular adenoma; and hemangioma.

7) Bone cancers, including, e.g., osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, e.g., cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, e.g., cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, e.g., cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia.

11) Skin cancers, including, e.g., malignant melanoma, basal cell carcinoma, squamous cell carcinoma, Kaposi's sarcoma, moles dysplastic nevi, lipoma, angioma, dermatofibroma, keloids, and psoriasis.

12) Adrenal gland cancers, including, e.g., neuroblastoma.

13) Pancreatic cancers, including, e.g., exocrine pancreatic cancers such as adenocarcinomas (M8140/3), adenosquamous carcinomas, signet ring cell carcinomas, hepatoid carcinomas, colloid carcinomas, undifferentiated carcinomas, and undifferentiated carcinomas with osteoclast-like giant cells; and exocrine pancreatic tumors.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound of formula (I) may be combined with existing methods of treating cancers, e.g., by chemotherapy, irradiation, or surgery (e.g., oophorectomy). In some embodiments, a compound of formula (I) can be administered before, during, or after another anticancer agent or treatment.

A cellular proliferative disorder can also include hemangiomatosis in newborns, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenoisis, and cirrhosis.

Also provided herein is a method of treating a neurological disorder in a patient. The method comprises administering to the patient a therapeutically effective amount of a compound as described herein or a pharmaceutically acceptable derivative thereof.

A neurological disorder can include Alzheimer's disease, Parkinson's disease, autism, enuresis, amyotrophic lateral sclerosis (ALS), hypoxia, hypoglycemia, epilepsy, Huntington's disease, multiple sclerosis, stroke and ischemia associated with stroke, neural paropathy, motor neuron diseases, sciatic crush, and peripheral neuropathy.

Treatment of the disorders as described herein may be accomplished through the inhibition of one or more kinases, e.g., ABL1, ABL2/ARG, PIK3-α, PIK3-β, PIK3-γ, PIK3-δ, c-Src, Fgr, and RIPK2, and mutants thereof. In some embodiments, the kinase is selected from ABL1 and PIK3-α. Accordingly, provided herein is a method of inhibiting one or more kinases in a patient, the method comprising administering to the patient a therapeutically effective amount of a compound of formula (I) or a pharmaceutically acceptable salt thereof.

In some embodiments, the methods described herein can be used in vitro, e.g., inhibiting one or more kinases in a cell, inhibiting cellular proliferation of cancer cells, inducing cell death of cancer cells, and inducing apoptosis of cancer cells. Such in vitro methods can be performed by contacting a cell (e.g., a cancer cell) with an effective amount of a compound of formula (I). Uses of such in vitro methods include, but are not limited to, use in a screening assay (e.g., wherein the compound is used as a positive control or standard compared to compounds of unknown activity or potency in inhibiting kinase activity).

EXAMPLES

General Procedure A. Preparation of 4-Alkylamino-2-methylsulfanyl-pyrimidine-5-carboxylic acid Ethyl Ester Compounds (2a-i)

Intermediate compounds (2a)-(2j) were prepared by the procedure described below and illustrated in Scheme 12.

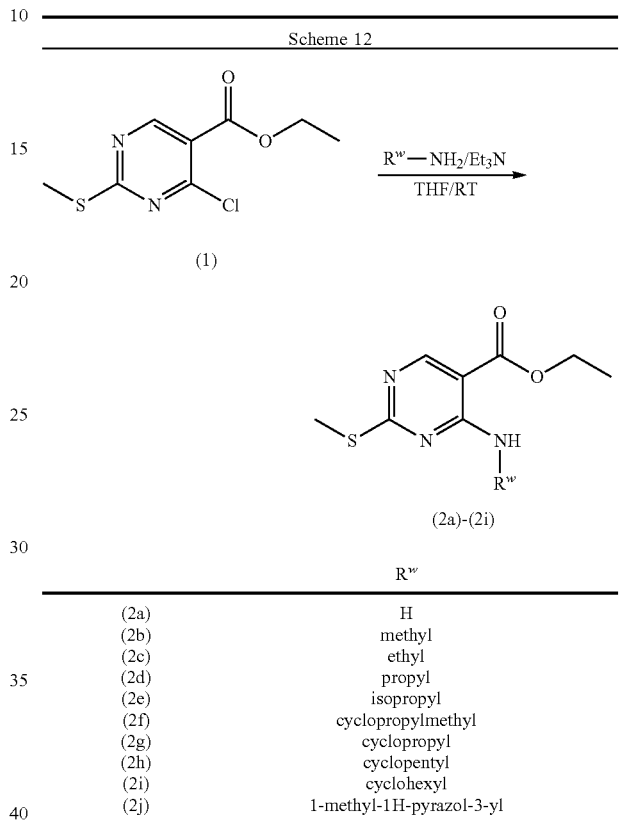

Scheme 12

|      | $R^w$ |
|------|-------|
| (2a) | H |
| (2b) | methyl |
| (2c) | ethyl |
| (2d) | propyl |
| (2e) | isopropyl |
| (2f) | cyclopropylmethyl |
| (2g) | cyclopropyl |
| (2h) | cyclopentyl |
| (2i) | cyclohexyl |
| (2j) | 1-methyl-1H-pyrazol-3-yl |

4-Chloro-2-(methylsulfanyl)pyrimidine-5-carboxylic acid ethyl ester (1) (1 equiv.), was dissolved in THF to which triethylamine (3 equiv.) alkyl amine (1.1 equiv.) was added and stirred overnight at room temperature. The precipitated salts were filtered and the solvent evaporated under reduced pressure. The resulting oil was dissolved in EtOAc, washed with sodium bicarbonate, then dried over $Na_2SO_4$. The salts were filtered, and the solvent was evaporated in vacuum to give the product.

Preparation 1.
4-Amino-2-(methylsulfanyl)pyrimidine-5-carboxylic acid ethyl ester (2a)

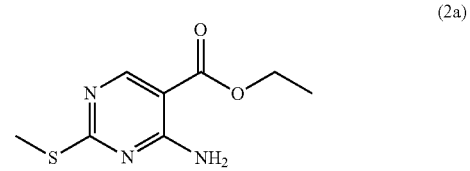

Starting from 4-chloro-2-(methylsulfanyl)pyrimidine-5-carboxylic acid ethyl ester (1) and ammonium hydroxide, (2a) was obtained in 90% yield using the method described in General Procedure A. $^1$H NMR (300 MHz, CDCl$_3$), δ 1.25 (t, OCH$_2$CH$_3$, 3H), 2.45 (s, S—CH$_3$, 3H), 4.30 (q, OCH$_2$CH$_3$, 2H), 8.10 (br s, NH$_2$, 2H), 8.58 (s, Ar—H, 1H).

Preparation 2. 4-Methylamino-2-(methylsulfanyl) pyrimidine-5-carboxylic acid ethyl ester (2b)

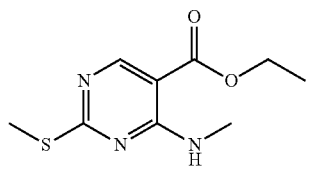

Starting from 4-chloro-2-(methylsulfanyl)pyrimidine-5-carboxylic acid ethyl ester (1) and methylamine, compound (2b) was obtained in 85% yield using the method described in General Procedure A. $^1$H NMR (300 MHz, CDCl$_3$), δ 1.25 (t, OCH$_2$CH$_3$, 3H), 3.12 (d, NH—CH$_3$, 3H), 2.50 (s, S—CH$_3$, 3H), 4.28 (q, OCH$_2$CH$_3$, 2H), 8.90 (br s, NH, H), 8.55 (s, Ar—H, 1H).

Preparation 3. 4-Ethylamino-2-(methylsulfanyl) pyrimidine-5-carboxylic acid ethyl ester

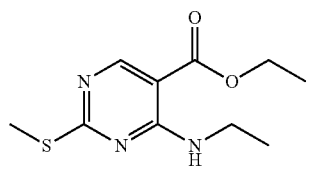

Starting from 4-chloro-2-(methylsulfanyl)pyrimidine-5-carboxylic acid ethyl ester (1) and ethylamine, compound (2c) was obtained in 85% yield using the method described in General Procedure A. $^1$H NMR (300 MHz, CDCl$_3$), δ 1.24 (t, NHCH$_2$CH$_3$, 3H), 1.29 (t, OCH$_2$CH$_3$, 3H), 2.45 (s, S—CH$_3$, 3H), 3.54-3.50 (m, NHCH$_2$CH$_3$, 2H), 4.30 (q, OCH$_2$CH$_3$, 2H), 8.10 (bs, NH, 1H), 8.65 (s, Ar—H, 1H).

Preparation 4. 4-Propylamino-2-(methylsulfanyl) pyrimidine-5-carboxylic acid ethyl ester (2d)

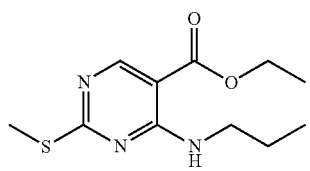

Starting from 4-chloro-2-(methylsulfanyl)pyrimidine-5-carboxylic acid ethyl ester (1) and propylamine, compound (2d) was obtained in 89% yield using the method described in General Procedure A. $^1$H NMR (300 MHz, CDCl$_3$), δ 1.00 (t, NHCH$_2$CH$_2$CH$_3$, 3H), 1.35 (t, OCH$_2$CH$_3$, 3H), 1.70-1.60 (m, NHCH$_2$CH$_2$CH$_3$ 2H), 2.42 (s, S—CH$_3$, 3H), 3.58-3.44 (m, NHCH$_2$CH$_2$CH$_3$, 2H), 4.25 (q, OCH$_2$CH$_3$, 2H), 8.26 (br s, NH, 1H), 8.60 (s, Ar—H, 1H).

Preparation 5. 4-Isopropylamino-2-(methylsulfanyl) pyrimidine-5-carboxylic acid ethyl ester (2e)

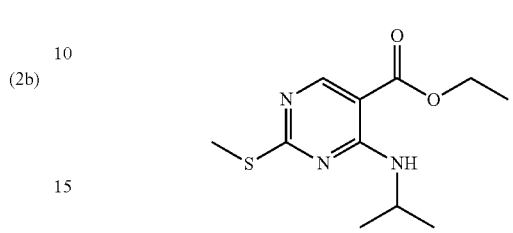

Starting from 4-chloro-2-(methylsulfanyl)pyrimidine-5-carboxylic acid ethyl ester (1) and isopropyl amine, compound (2e) was obtained in 87% yield using the method described in General Procedure A. $^1$H NMR (300 MHz, CDCl$_3$), δ 1.19 (d, CH—(CH$_3$)$_2$, 6H), 1.29 (t, OCH$_2$CH$_3$, 3H), 2.45 (s, S—CH$_3$, 3H), 4.06 (q, OCH$_2$CH$_3$, 2H), 4.37-4.305 (m, CH—CH$_3$)$_2$, 1H), 8.05 (bs, NH, 1H), 8.5 (s, Ar—H, 1H).

Preparation 6. 4-(Cyclopropylmethylamino)-2-(methylsulfanyl)pyrimidine-5-carboxylic acid ethyl ester (2f)

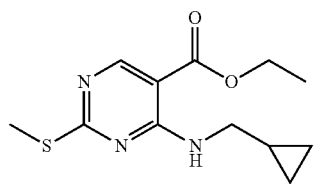

Starting from 4-chloro-2-(methylsulfanyl)pyrimidine-5-carboxylic acid ethyl ester (1) and cyclopropylmethyl amine, compound (2f) was obtained in 90% yield using the method described in General Procedure A. $^1$H NMR (300 MHz, CDCl$_3$), δ 0.56-0.55 (m, CH$_2$, 2H), 0.60-0.58 (m, CH$_2$, 2H), 1.14-1.10 (m, CH-Cyclopropyl, 1H), 1.40 (t, OCH$_2$CH$_3$, 3H), 2.53 (s, S—CH$_3$, 3H), 3.43-3.39 (m, CH$_2$—NH, 2H), 4.33 (q, OCH$_2$CH$_3$, 2H), 8.33 (bs, NH, 1H), 8.63 (s, Ar—H, 1H).

Preparation 7. 4-Cyclopropylamino-2-(methylsulfanyl)pyrimidine-5-carboxylic acid ethyl ester (2g)

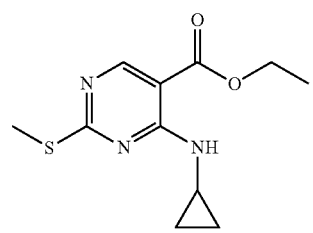

Starting from 4-chloro-2-(methylsulfanyl)pyrimidine-5-carboxylic acid ethyl ester (1) and cyclopropyl amine, compound (2g) was obtained in 86% yield using the method described in General Procedure A. $^1$H NMR (300 MHz, CDCl$_3$), δ 0.63-0.61 (m, CH$_2$, 2H), 0.89-0.84 (m, CH$_2$, 2H), 1.40 (t, OCH$_2$CH$_3$, 3H), 2.58 (s, S—CH$_3$, 3H), 3.01-2.95 (m, CH-Cyclopropyl, 1H), 4.32 (q, OCH$_2$CH$_3$, 2H), 8.24 (bs, NH, 1H), 8.63 (s, Ar—H, 1H).

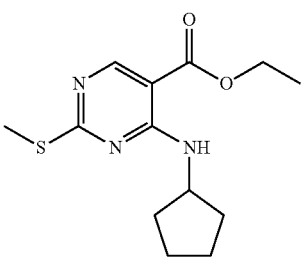

(2h)

Starting from 4-chloro-2-(methylsulfanyl)pyrimidine-5-carboxylic acid ethyl ester (1) and cyclopentyl amine, compound (2h) was obtained in 90% yield using the method described in General Procedure A. $^1$H NMR (300 MHz, CDCl$_3$), δ 1.35 (t, OCH$_2$CH$_3$, 3H), 1.50-1.79 (m, 3CH$_2$, 6H), 2.52 (s, S—CH$_3$, 3H), 2.00-2.10 (m, CH$_2$, 2H), 4.49-4.54 (m, NH—CH—, 1H), 4.30 (q, OCH$_2$CH$_3$, 2H), 8.25 (bs, NH, 1H), 8.60 (s, Ar—H, 1H).

Preparation 9. 4-Cyclohexylamino-2-(methylsulfanyl)pyrimidine-5-carboxylic acid ethyl ester (2i)

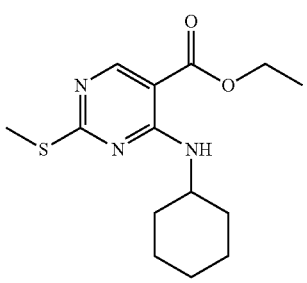

(2i)

Starting from 4-chloro-2-(methylsulfanyl)pyrimidine-5-carboxylic acid ethyl ester (1) and cyclohexyl amine, compound (2i) was obtained in 85% yield using the method described in General Procedure A. $^1$H NMR (300 MHz, CDCl$_3$), δ 1.30-1.41 (m, 2CH$_2$ & OCH$_2$CH$_3$, 7H), 1.59-1.64 (m, CH$_2$, 2H), 1.73-1.81 (m, CH$_2$, 2H), 1.94-2.27 (m, 2H), 2.51 (s, S—CH$_3$ 3H), 4.09-4.14 (m, NH—CH—, 1H), 4.30 (q, OCH$_2$CH$_3$, 2H), 8.22 (bs, NH, 1H), 8.60 (s, Ar—H, 1H).

General Procedure B. Preparation of [4-Alkylamino-2-(methylsulfanyl)pyrimidin-5-yl]methanol Compounds (3a)-(3i)

Intermediate compounds (3a)-(3j) were prepared by the procedure described below and illustrated in Scheme 13.

Scheme 13

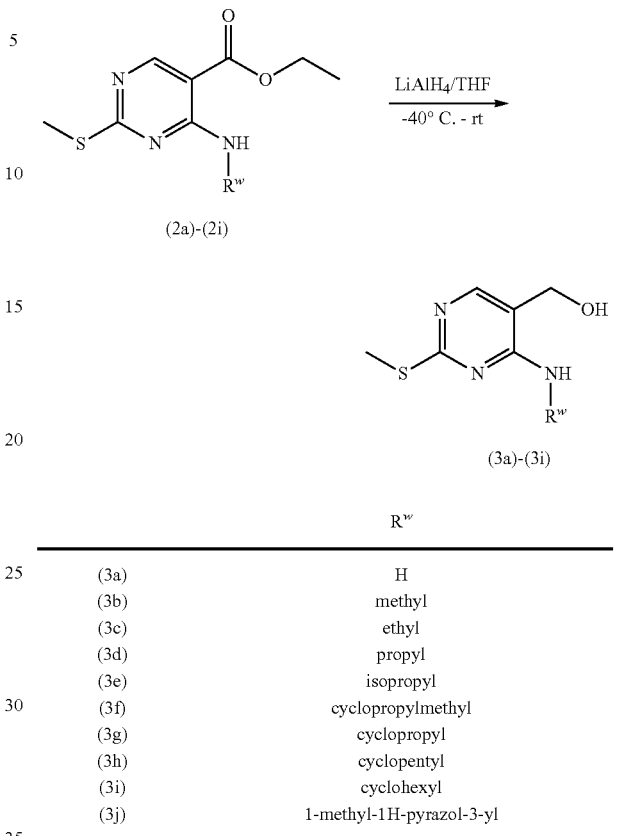

| | R$^w$ |
|---|---|
| (3a) | H |
| (3b) | methyl |
| (3c) | ethyl |
| (3d) | propyl |
| (3e) | isopropyl |
| (3f) | cyclopropylmethyl |
| (3g) | cyclopropyl |
| (3h) | cyclopentyl |
| (3i) | cyclohexyl |
| (3j) | 1-methyl-1H-pyrazol-3-yl |

Lithium aluminum hydride (1.5 equiv.) was suspended in THF under a nitrogen atmosphere, and the mixture was cooled with dry ice. The compound (2) (1 equiv.) was dissolved in THF and added dropwise to the cooled solution while keeping the reaction temperature below −20° C. The reaction mixture was allowed to warm to room temperature, and stirred for 5 h. The reaction was then quenched by the addition of water (5 mL), 15% NaOH (10 mL) and then further water (15 mL). The white solid that precipitated was filtered and the filtrate was evaporated under reduced pressure to obtain the product as a yellow solid.

Preparation 10. [4-Amino-2-(methylsulfanyl)pyrimidin-5-yl]methanol (3a)

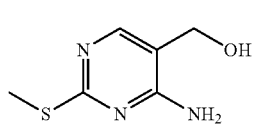

(3a)

Starting from compound (2a), 95% of compound (3a) was obtained in 95% yield using the method described in General Procedure B. $^1$H NMR (300 MHz, DMSO-d$_6$), δ 2.56 (s, S—CH$_3$, 3H), 4.25 (s, CH$_2$OH, 2H), 5.30 (br s, OH, 1H), 6.70 (br s, NH$_2$, 2H), 7.85 (s, Ar—H, 1H).

Preparation 11. [4-Methylamino-2-(methylsulfanyl)pyrimidin-5-yl]methanol (3b)

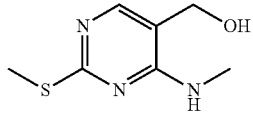
(3b)

Starting from compound (2b), compound (3b) was obtained in 93% yield using the method described in General Procedure B. $^1$H NMR (300 MHz, DMSO-d$_6$), δ 2.55 (s, S—CH$_3$, 3H), 3.0 (d, N—CH$_3$, 3H), 4.24 (s, CH$_2$OH, 2H), 6.70 (br s, NH, 1H), 7.92 (s, Ar—H, 1H).

Preparation 12. [4-Ethylamino-2-(methylsulfanyl)pyrimidin-5-yl]methanol (3c)

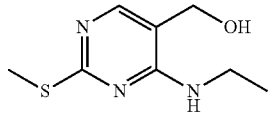
(3c)

Starting from compound (2c), compound (3c) was obtained in 95% yield using the method described in General Procedure B. $^1$H NMR (300 MHz, CDCl$_3$), δ 1.26 (t, NHCH$_2$CH$_3$, 3H), 2.51 (s, S—CH$_3$, 3H), 3.52-2.48 (m, NHCH$_2$CH$_3$, 2H), 4.49 (s, CH$_2$OH, 2H), 4.65 (bs, OH, 1H), 5.90 (bs, NH, 1H), 7.62 (s, Ar—H, 1H).

Preparation 13. [4-Propylamino-2-(methylsulfanyl)pyrimidine-5-yl]methanol (3d)

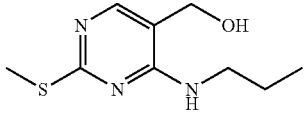
(3d)

Starting from compound (2d), compound (3d) was obtained in 95% yield using the method described in General Procedure B. $^1$H NMR (300 MHz, CDCl$_3$), δ 0.97 (t, CH$_2$CH$_3$, 3H), 1.55-1.68 (m, NHCH$_2$CH$_2$CH$_3$, 2H), 2.49 (s, S—CH$_3$, 3H), 3.42 (q, NHCH$_2$CH$_2$CH$_3$ 2H), 4.48 (s, CH$_2$OH, 2H), 6.00 (br s, NH, 1H), 7.58 (s, Ar—H, 1H).

Preparation 14. [4-Isopropylamino-2-(methylsulfanyl)pyrimidine-5-yl]methanol (3e)

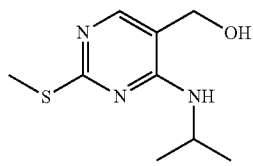
(3e)

Starting from compound (2e), compound (3e) was obtained in 95% yield using the method described in General Procedure B. $^1$H NMR (300 MHz, CDCl$_3$), δ 1.27 (d, CH—(CH$_3$)$_2$, 6H), 2.50 (s, S—CH$_3$, 3H), 4.38-4.31 (m, CH—CH$_3$)$_2$, 4.46 (s, CH$_2$OH, 2H), 5.80 (bs, NH, 1H), 7.57 (s, Ar—H, 1H).

Preparation 15. [4-(Cyclopropylmethyl)amino-2-(methylsulfanyl)pyrimidine-5-yl]methanol (3f)

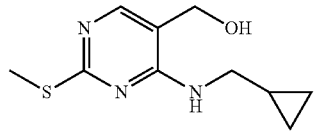
(3f)

Starting from compound (2f), compound (3f) was obtained in 92% yield using the method described in General Procedure B. $^1$H NMR (300 MHz, CDCl$_3$), δ 0.03-0.015 (m, CH$_2$, 2H), 0.31-0.28 (m, CH$_2$, 2H), 0.87-0.82 (m, CH-Cyclopropyl, 1H), 2.25 (s, S—CH$_3$, 3H), 3.12-3.08 (m, CH$_2$—NH, 2H), 4.25 (s, CH$_2$OH, 2H), 5.88 (bs, NH, 1H), 7.31 (s, Ar—H, 1H).

Preparation 16. [4-Cyclopropylamino-2-(methylsulfanyl)pyrimidine-5-yl]methanol (3g)

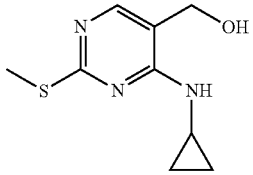
(3g)

Starting from compound (2g), compound (3g) was obtained in 90% yield using the method described in General Procedure B. $^1$H NMR (300 MHz, CDCl$_3$), δ 0.67-0.65 (m, CH$_2$, 2H), 0.90-0.86 (m, CH$_2$, 2H), 2.55 (s, S—CH$_3$, 3H), 3.01-2.95 (m, CH-Cyclopropyl, 1H), 4.28 (s, C<u>H</u>$_2$H, 1H), 8.50 (bs, NH, 1H), 8.67 (s, Ar—H, 1H).

Preparation 17. [4-Cyclopentylamino-2-(methylsulfanyl)pyrimidine-5-yl]methanol (3h)

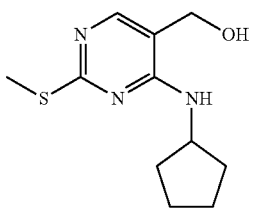
(3h)

Starting from compound (2h), compound (3h) was obtained in 90% yield using the method described in General Procedure B. $^1$H NMR (300 MHz, CDCl$_3$), δ 1.40-1.49 (m, CH$_2$, 2H), 1.62-1.78 (m, 2CH$_2$, 4H), 2.00-2.15 (m, CH$_2$, 2H), 2.50 (s, S—CH₃, 3H), 4.45-4.50 (m, CH-cyclopentyl, 1H), 4.52 (s, CH₂OH, 2H), 5.80 (br s, NH, 1H), 7.65 (s, Ar—H, 1H).

Preparation 18. [4-Cyclohexylamino-2-(methylsulfanyl)pyrimidine-5-yl]methanol (3i)

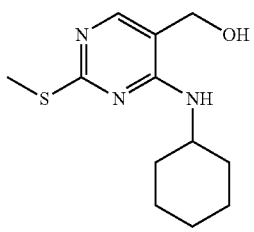

(3i)

Starting from compound (2i), compound (3i) was obtained in 90% yield using the method described in General Procedure B. ¹H NMR (300 MHz, CDCl₃), δ 1.24-1.43 (m, 2CH₂, 4H), 1.61-1.78 (m, 2CH₂, 4H), 1.99-2.08 (m, CH₂, 2H), 2.51 (s, S—CH₃, 3H), 3.95-4.08 (m, CH-Cyclohexyl, 1H), 4.45 (s, CH₂OH, 2H), 5.8 (br s, NH, 1H), 7.59 (s, Ar—H, 1H).

General Procedure C. Preparation of 4-Alkylamino-2-methylsulfanyl-pyrimidine-5-carboxaldehyde Compounds (4a)-(4i)

Intermediate compounds (4a)-(4i) and (4m) were prepared by the procedure described below and illustrated in Scheme 14.

Scheme 14

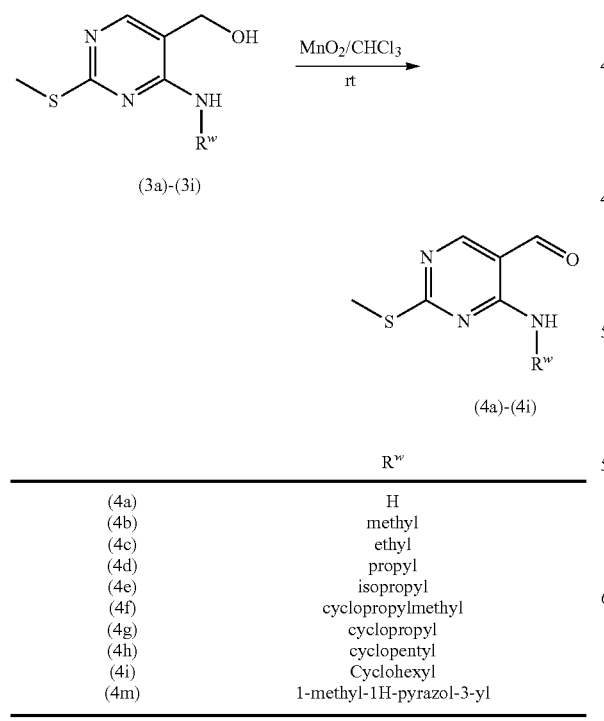

| | R^w |
|---|---|
| (4a) | H |
| (4b) | methyl |
| (4c) | ethyl |
| (4d) | propyl |
| (4e) | isopropyl |
| (4f) | cyclopropylmethyl |
| (4g) | cyclopropyl |
| (4h) | cyclopentyl |
| (4i) | Cyclohexyl |
| (4m) | 1-methyl-1H-pyrazol-3-yl |

The compound (3) (1 equiv.) was dissolved in chloroform to which MnO₂ (6 equiv.) was added. The resulting suspension was stirred overnight, an additional portion of MnO₂ (1.5 equiv.) was added and stirring was continued for a further 12 h. The solids were removed by filtration through a diatomaceous earth pad, which was washed with further chloroform. The chloroform was evaporated in vacuum to obtain the product (4).

Preparation 19. 4-Amino-2-(methylsulfanyl)pyrimidine-5-carboxaldehyde (4a)

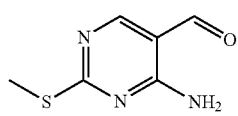

(4a)

Starting from compound (3a), compound (4a) was obtained in 72% yield using the method described in General Procedure C. ¹H NMR (300 MHz, DMSO-d₆), δ 2.55 (s, S—CH₃, 3H), 5.74 (bs, NH, 1H), 8.20 (bs, NH, 1H), 8.45 (s, Ar—H, 1H), 9.80 (s, HC=O, 1H).

Preparation 20. 4-Methylamino-2-(methylsulfanyl)pyrimidine-5-carboxaldehyde (4b)

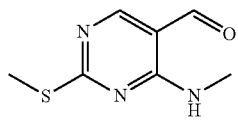

(4b)

Starting from compound (3b), compound (4b) was obtained in 75% yield using the method described in General Procedure C. ¹H NMR (300 MHz, CDCl₃), δ 2.55 (s, S—CH₃, 3H), 3.05 (d, N—CH₃, 3H), 7.90 (bs, NH, 1H), 8.42 (s, Ar—H, 1H), 9.69 (s, HC=O, 1H).

Preparation 21. 4-Ethylamino-2-(methylsulfanyl)pyrimidine-5-carboxaldehyde (4c)

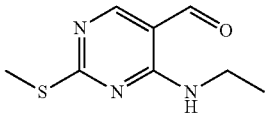

(4c)

Starting from compound (3c), compound (4c) was obtained in 72% yield using the method described in General Procedure C. ¹H NMR (300 MHz, CDCl₃), δ 1.29 (t, CH₂CH₃, 3H), 2.57 (s, S—CH₃, 3H), 3.64-3.60 (m, N—CH₂CH₃, 3H), 8.29 (s, Ar—H, 1H), 8.58 (s, NH, 1H), 9.69 (s, HC=O, 1H).

Preparation 22. 4-Propylamino-2-(methylsulfanyl)pyrimidine-5-carboxaldehyde (4d)

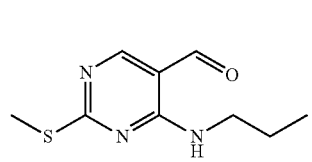

(4d)

Starting from compound (3d), compound (4d) was obtained in 72% yield using the method described in General Procedure C. $^1$H NMR (300 MHz, CDCl$_3$), δ 0.91 (t, N—CH$_2$CH$_2$CH$_3$, 3H) 1.73-1.59 (m, N—CH$_2$CH$_2$CH$_3$, 2H), 2.54 (s, S—CH$_3$, 3H), 3.57-3.53 (m, N—CH$_2$CH$_2$CH$_3$, 2H), 8.28 (s, Ar—H, 1H), 8.63 (s, NH, 1H), 9.69 (s, HC=O, 1H).

Preparation 23. 4-Isopropylamino-2-(methylsulfanyl)pyrimidine-5-carboxaldehyde (4e)

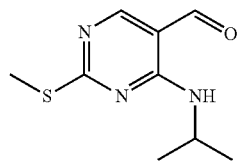

(4e)

Starting from compound (3e), compound (4e) was obtained in 75% yield using the method described in General Procedure C. $^1$H NMR (300 MHz, CDCl$_3$), δ 1.23 (d, CH(CH$_3$)$_2$, 6H), 2.47 (s, S—CH$_3$, 3H), 4.43-4.32 (m, —CH(CH$_3$)$_2$, 1H), 8.21 (s, Ar—H, 1H), 8.40 (bs, NH, 1H), 9.61 (s, HC=O, 1H).

Preparation 24. 4-(Cyclopropylmethyl)amino-2-(methylsulfanyl)pyrimidine-5-carboxaldehyde (4f)

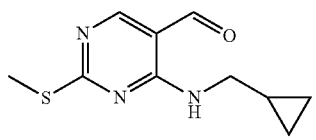

(4f)

Starting from compound (3f), compound (4f) was obtained in 75% yield using the method described in General Procedure C. $^1$H NMR (300 MHz, CDCl$_3$), δ 0.06-0.048 (m, CH$_2$, 2H), 0.36-0.33 (m, CH$_2$, 2H), 0.89-0.84 (m, N—CH$_2$CH—, 1H), 2.30 (s, S—CH$_3$, 3H), 3.22-3.18 (m, N—CH$_2$—, 2H), 8.05 (s, Ar—H, 1H), 8.45 (bs, NH, 1H), 9.46 (s, HC=O, 1H).

Preparation 25. 4-Cyclopropylamino-2-(methylsulfanyl)pyrimidine-5-carboxaldehyde (4g)

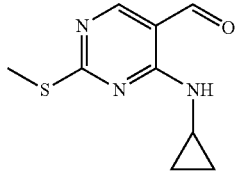

(4g)

Starting from compound (3g), compound (4g) was obtained in 75% yield using the method described in General Procedure C. $^1$H NMR (300 MHz, CDCl$_3$), δ 0.68-0.65 (m, CH$_2$, 2H), 0.93-0.87 (m, CH$_2$, 2H), 2.60 (s, S—CH$_3$, 3H), 3.08-3.00 (m, N—CH—, 2H), 8.31 (s, Ar—H, 1H), 8.62 (bs, NH, 1H), 9.69 (s, HC=O, 1H).

Preparation 26. 4-Cyclopentylamino-2-(methylsulfanyl)pyrimidine-5-carboxaldehyde (4h)

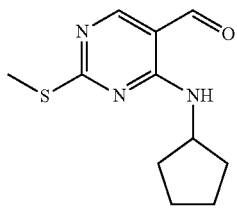

(4h)

Starting from compound (3h), compound (4h) was obtained in 77% yield using the method described in General Procedure C. $^1$H NMR (300 MHz, CDCl$_3$), δ 1.50-1.82 (m, 3CH$_2$, 6H), 2.01-2.12 (m, CH$_2$, 2H), 2.52 (s, S—CH$_3$, 3H), 4.49-4.54 (m, N—CH—, 1H), 8.25 (s, Ar—H, 1H), 8.60 (bs, NH, 1H), 9.65 (s, HC=O, 1H).

Preparation 27. 4-Cyclohexylamino-2-(methylsulfanyl)pyrimidine-5-carboxaldehyde (4i)

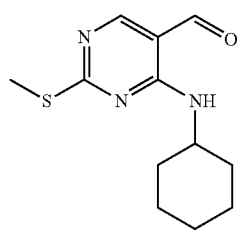

(4i)

Starting from compound (3i), compound (4i) was obtained in 76% yield using the method described in General Procedure C. $^1$H NMR (300 MHz, CDCl$_3$), δ 1.44-1.22 (m, 2CH$_2$, 4H), 1.80-1.60 (m, 2CH$_2$, 4H), 2.05-1.97 (m, CH$_2$, 2H), 2.51 (s, S—CH$_3$, 3H), 4.09-4.01 (m, NH—CH—, 1H), 8.15 (s, Ar—H, 1H), 8.55 (bs, NH, 1H), 9.62 (s, HC=O, 1H).

General Procedure D. Preparation of 4-Amino-2-methylsulfanyl-pyrimidine-5-carboxaldehyde Compounds (4j-l)

Intermediate compounds (4j)-(4l) were prepared by the procedure described below and illustrated in Scheme 15.

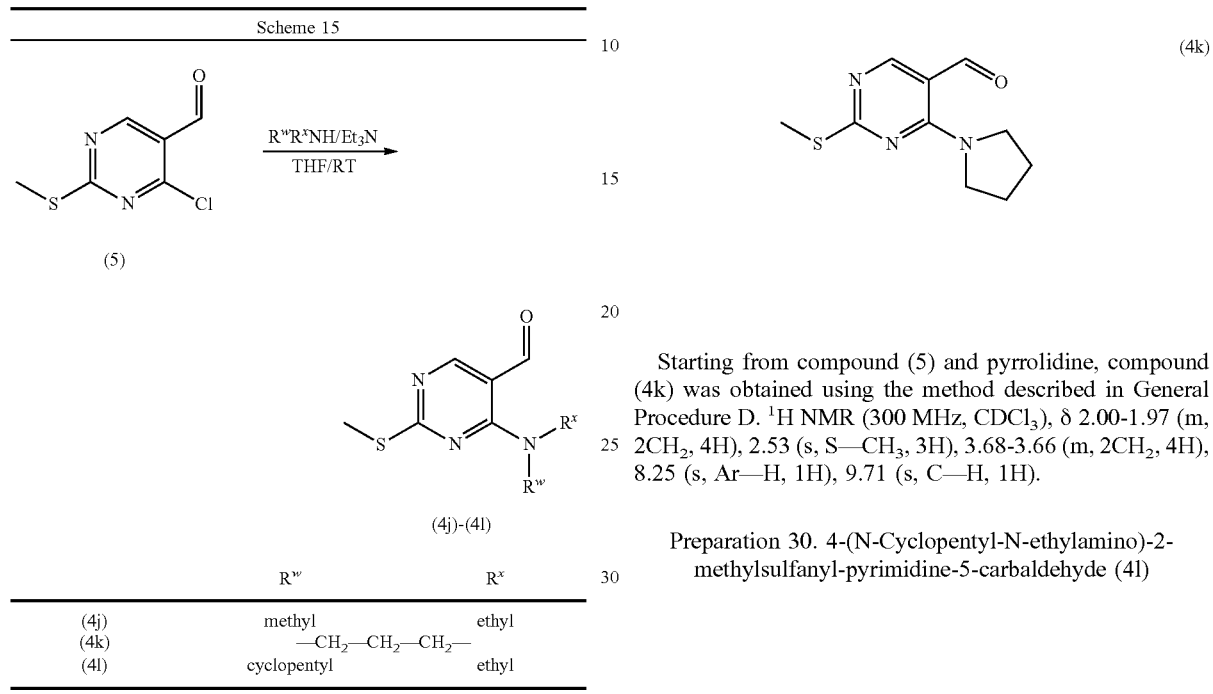

| | R*w* | R*x* |
|---|---|---|
| (4j) | methyl | ethyl |
| (4k) | —CH₂—CH₂—CH₂— | |
| (4l) | cyclopentyl | ethyl |

4-Chloro-2-(methylsulfanyl)pyrimidine-5-carboxaldehyde (5) (1 equiv.), was dissolved in THF to which triethylamine (3 equiv.) and the amine (1.1 equiv.) were added. The solution was stirred overnight at room temperature. The precipitated salts were filtered and the solvent was evaporated under reduced pressure. The resulting oil was dissolved in EtOAc, washed with sodium bicarbonate, then dried over Na₂SO₄. The salts were filtered, and the solvent was evaporated under reduced pressure to give the product (4).

Preparation 28. 4-(Ethyl-methyl-amino)-2-methylsulfanyl-pyrimidine-5-carboxaldehyde (4j)

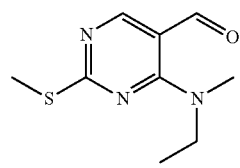

Starting from compound (5) and ethylmethylamine, compound (4j) was obtained using the method described in General Procedure D. ¹H NMR (300 MHz, CDCl₃), δ 1.29 (t, CH₂—CH₃, 3H), 2.55 (s, S—CH₃, 3H), 3.10 (s, N—CH₃, 3H), 3-77-3.70 (q, N—CH₂—, 2H), 8.45 (s, Ar—H, 1H), 9.73 (s, C—H, 1H).

Preparation 29. 2-Methylsulfanyl-4-pyrrolidin-1-yl-pyrimidine-5-carbaldehyde (4k)

Starting from compound (5) and pyrrolidine, compound (4k) was obtained using the method described in General Procedure D. ¹H NMR (300 MHz, CDCl₃), δ 2.00-1.97 (m, 2CH₂, 4H), 2.53 (s, S—CH₃, 3H), 3.68-3.66 (m, 2CH₂, 4H), 8.25 (s, Ar—H, 1H), 9.71 (s, C—H, 1H).

Preparation 30. 4-(N-Cyclopentyl-N-ethylamino)-2-methylsulfanyl-pyrimidine-5-carbaldehyde (4l)

Starting from compound (5) and N-cyclopentyl-N-ethylamine, compound (4l) was obtained using the method described in General Procedure D. ¹H NMR (300 MHz, CDCl₃), δ 1.14 (t, CH₂—CH₃, 3H), 1.58-1.52 (m, 3CH₂, 6H), 1.96-1.88 (m, CH₂, 2H), 2.46 (s, S—CH₃, 3H), 3.58-3.51 (q, CH₂, 2H), 4.33-4.30 (m, C—H, 1H), 8.36 (s, Ar—H, 1H), 9.66 (s, C—H, 1H).

General Procedure E. Preparation of 3-[4-Alkylamino-2-(methylsulfanyl)pyrimidin-5-yl]acrylonitrile Compounds (6a)-(6i)

Intermediate compounds (6a)-(6m) were prepared by the procedure described below and illustrated in Scheme 16.

Scheme 16

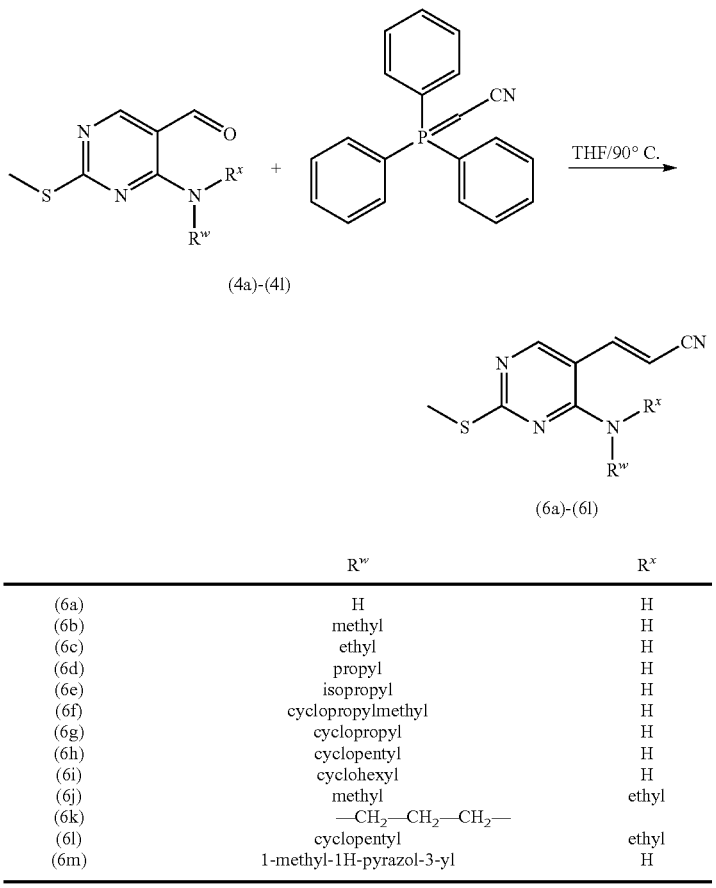

| | $R^w$ | $R^x$ |
|---|---|---|
| (6a) | H | H |
| (6b) | methyl | H |
| (6c) | ethyl | H |
| (6d) | propyl | H |
| (6e) | isopropyl | H |
| (6f) | cyclopropylmethyl | H |
| (6g) | cyclopropyl | H |
| (6h) | cyclopentyl | H |
| (6i) | cyclohexyl | H |
| (6j) | methyl | ethyl |
| (6k) | —CH$_2$—CH$_2$—CH$_2$— | |
| (6l) | cyclopentyl | ethyl |
| (6m) | 1-methyl-1H-pyrazol-3-yl | H |

The aldehyde 4 (1 equiv.) was dissolved in anhydrous benzene to which (triphenylphosphoranylidene)acetonitrile (1.1 equiv.) was added and stirred for 5-7 h at 90° C. After completion of the reaction, checked by TLC, the reaction mixture was brought to room temperature and the solvent was removed under reduced pressure to get crude product. The pure compound (6) was obtained by flash chromatography with 12-15% ethyl acetate in hexane.

Example 1. 3-[4-Amino-2-(methylsulfanyl)pyrimidin-5-yl]acrylonitrile (6a)

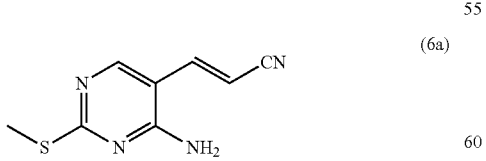

(6a)

Starting from compound (4a), compound (6a) was obtained in 65% yield using the method described in General Procedure E. $^1$H NMR (300 MHz, CDCl$_3$), δ 2.43 (s, S—CH$_3$, 3H), 6.30 (d, =CH, J=16.2 Hz, 1H), 7.4 (bs, NH, 1H), 7.63 (d, =CH, J=16.2 Hz, 1H), 8.40 (s, Ar—H, 1H).

Example 2. 3-[4-Methylamino-2-(methylsulfanyl)pyrimidin-5-yl]acrylonitrile (6b)

Starting from compound (4b), compound (6b) was obtained in 63% yield using the method described in General Procedure E. $^1$H NMR (300 MHz, CDCl$_3$), δ 2.46 (s, S—CH$_3$, 3H), 2.86 (d, N—CH$_3$, 3H), 6.31 (d, =CH, J=16.2 Hz, 1H), 7.62 (d, =CH, J=16.2 Hz, 1H), 7.69 (bs, NH, 1H), 8.32 (s, Ar—H, 1H).

Example 3. 3-[4-Ethylamino-2-(methylsulfanyl)pyrimidin-5-yl]acrylonitrile (6c)

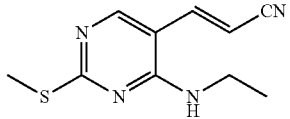
(6c)

Starting from compound (4c), compound (6c) was obtained in 63% yield using the method described in General Procedure E. $^1$H NMR (300 MHz, DMSO-d$_6$), δ 1.15 (t, N—CH$_2$CH$_3$, 3H), 2.51 (s, S—CH$_3$, 3H), 3.45-3.33 (m, N—CH$_2$CH$_3$, 2H), 6.29 (d, =CH, J=16.2 Hz, 1H), 7.68-7.63 (m, =CH, & NH, 2H), 8.33 (s, Ar—H, 1H).

Example 4. 3-[4-Propylamino-2-(methylsulfanyl)pyrimidin-5-yl]acrylonitrile (6d)

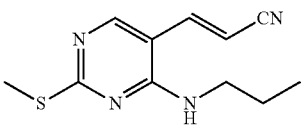
(6d)

Starting from compound (4d), compound (6d) was obtained in 63% yield using the method described in General Procedure E. $^1$H NMR (300 MHz, CDCl$_3$), δ 0.90 (t, N—CH$_2$CH$_2$CH$_3$, 3H), 1.62-1.55 (m, N—CH$_2$CH$_2$CH$_3$, 2H), 2.45 (s, S—CH$_3$, 3H), 3.44-3.37 (m, N—CH$_2$CH$_2$CH$_3$ 2H), 5.57 (bs, NH, 1H), 6.67 (d, =CH, J=16.2 Hz, 1H), 7.29 (d, =CH, J=16.2 Hz, 1H), 8.00 (s, Ar—H, 1H).

Example 5. 3-[4-Isopropylamino-2-(methylsulfanyl)pyrimidin-5-yl]acrylonitrile (6e)

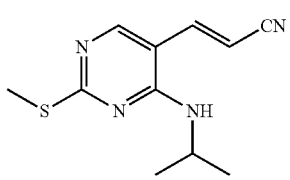
(6e)

Starting from compound (4e), compound (6e) was obtained in 63% yield using the method described in General Procedure E. $^1$H NMR (300 MHz, CDCl$_3$), δ 1.31 (d, N—CH—(CH$_3$)$_2$, 6H), 2.54 (s, S—CH$_3$, 3H), 4.49-4.40 (m, N—CH(CH$_3$)$_2$, 1H), 4.86 (bs, NH, 1H), 5.74 (d, =CH, J=16.5 Hz, 1H), 7.25 (d, =CH, J=16.5 Hz, 1H), 8.09 (s, Ar—H, 1H).

Example 6. 3-[4-(Cyclopropylmethyl)amino-2-(methylsulfanyl)pyrimidin-5-yl]-acrylonitrile (6f)

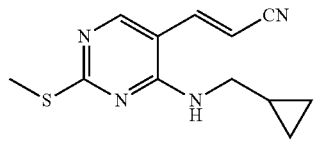
(6f)

Starting from compound (4f), compound (6f) was obtained in 65% yield using the method described in General Procedure E. $^1$H NMR (300 MHz, CDCl$_3$), δ 0.32-0.29 (m, CH$_2$, 2H), 0.62-0.60 (m, CH$_2$, 2H), 1.12-1.09 (m, N—CH$_2$—CH—, 1H), 2.54 (s, S—CH$_3$, 3H), 3.42-3.38 (m, N—CH$_2$—, 2H), 5.08 (bs, NH, 1H), 5.76 (d, =CH, J=16.5 Hz, 1H), 7.25 (d, =CH, J=16.2 Hz, 1H), 8.11 (s, Ar—H, 1H).

Example 7. 3-[4-Cyclopropylamino-2-(methylsulfanyl)pyrimidin-5-yl]acrylonitrile (6g)

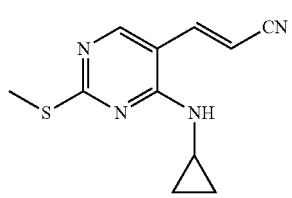
(6g)

Starting from compound (4g), compound (6g) was obtained in 65% yield using the method described in General Procedure E. $^1$H NMR (300 MHz, CDCl$_3$), δ 0.63-0.61 (m, CH$_2$, 2H), 0.90-0.87 (m, CH$_2$, 2H), 2.57 (s, S—CH$_3$, 3H), 2.94-2.88 (m, N—CH—, 1H), 5.41 (bs, NH, 1H), 5.74 (d, =CH, J=16.2 Hz, 1H), 7.29 (d, =CH, J=16.5 Hz, 1H), 8.11 (s, Ar—H, 1H).

Example 8. 3-[4-Cyclopentylamino-2-(methylsulfanyl)pyrimidin-5-yl]acrylonitrile (6h)

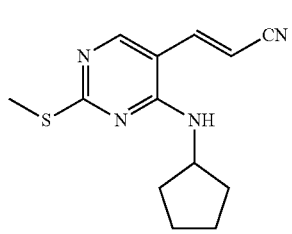
(6h)

Starting from compound (4h), compound (6h) was obtained in 65% yield using the method described in General Procedure E. $^1$H NMR (300 MHz, CDCl$_3$), δ 1.54-1.48 (m, CH$_2$, 2H), 1.80-1.70 (m, 2CH$_2$, 4H), 2.16-2.10 (m, CH$_2$, 2H), 2.54 (s, S—CH$_3$, 3H), 4.51-4.44 (m, N—CH—, 1H), 5.07 (bs, NH, 1H), 5.73 (d, =CH, J=16.2 Hz, 1H), 7.26 (d, =CH, J=16.5 Hz, 1H), 8.09 (s, Ar—H, 1H).

Example 9. 3-[4-Cyclohexylamino-2-(methylsulfanyl)pyrimidin-5-yl]acrylonitrile (6i)

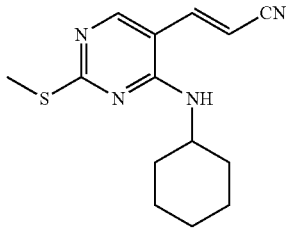

(6i)

Starting from compound (4i), compound (6i) was obtained in 65% yield using the method described in General Procedure E. $^1$H NMR (300 MHz, CDCl$_3$), δ 1.46-1.24 (m, 2CH$_2$, 4H), 1.83-1.67 (m, 2CH$_2$, 4H), 2.09-2.04 (m, CH$_2$, 2H), 2.54 (s, S—CH$_3$, 3H), 4.12-4.07 (m, N—CH—, 1H), 4.99 (bs, NH, 1H), 5.73 (d, =CH, J=16.5 Hz, 1H), 7.26 (d, =CH, J=16.5 Hz, 1H), 8.08 (s, Ar—H, 1H).

Example 10. 3-[4-(N-Ethyl-N-methylamino)-2-(methylsulfanyl)pyrimidin-5-yl]acrylonitrile (6j)

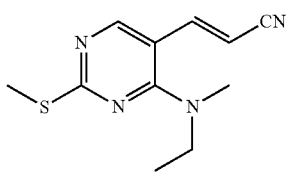

(6j)

Starting from compound (4j), compound (6j) was obtained using the method described in General Procedure E. $^1$H NMR (300 MHz, CDCl$_3$), δ 1.18 (t, CH$_2$—C$\underline{H}_3$, 3H), 2.43 (s, S—CH$_3$, 3H), 3.02 (s, N—CH$_3$, 3H), 3.51-3.44 (q, N—CH$_2$—, 2H), 5.53 (d, =H, J=16.2 Hz, 1H), 7.28 (d, =H, J=16.5 Hz, 1H), 7.97 (s, Ar—H, 1H).

Example 11. 3-[2-Methylsulfanyl-4-(pyrrolidin-1-yl)pyrimidin-5-yl]acrylonitrile (6k)

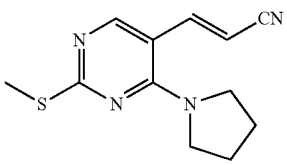

(6k)

Starting from compound (4k), compound (6k) was obtained using the method described in General Procedure E. $^1$H NMR (300 MHz, CDCl$_3$), δ 2.01-1.96 (m, 2CH$_2$, 4H), 2.52 (s, S—CH$_3$, 3H), 3.69-3.65 (m, 2CH$_2$, 4H), 5.54 (d, =H, J=16.2 Hz, 1H), 7.62 (d, =H, J=16.5 Hz, 1H), 8.05 (s, Ar—H, 1H).

Example 12. 3-[4-(N-Cyclopentyl-N-ethylamino)-2-(methylsulfanyl)pyrimidin-5-yl]acrylonitrile (6l)

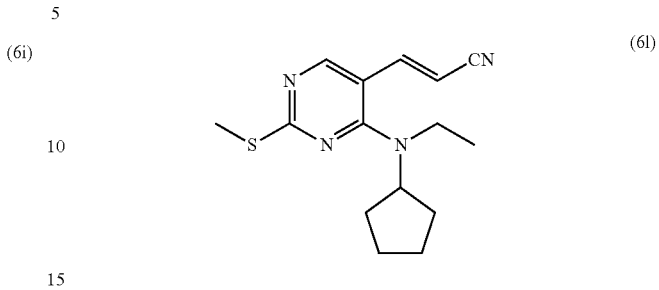

(6l)

Starting from compound (4l), compound (6l) was obtained using the method described in General Procedure E. $^1$H NMR (300 MHz, CDCl$_3$), δ 1.30 (t, CH$_2$—C$\underline{H}_3$, 3H), 1.78-1.72 (m, 3CH$_2$, 6H), 1.93-1.86 (m, CH$_2$, 2H), 2.53 (s, S—CH$_3$, 3H), 3.52-3.45 (q, N—CH$_2$—, 2H), 4.24-4.17 (m, —C—H—, 1H), 5.65 (d, =H, J=16.5 Hz, 1H), 7.34 (d, =H, J=16.5 Hz, 1H), 8.09 (s, Ar—H, 1H).

General Procedure F. Example of 3-(2-Methanesulfinyl-4-alkylamino-pyrimidine-5-yl)-acrylonitrile Compounds (7a)-(7l)

Intermediate compounds (7a)-(7m) were prepared by the procedure described below and illustrated in Scheme 17.

Scheme 17

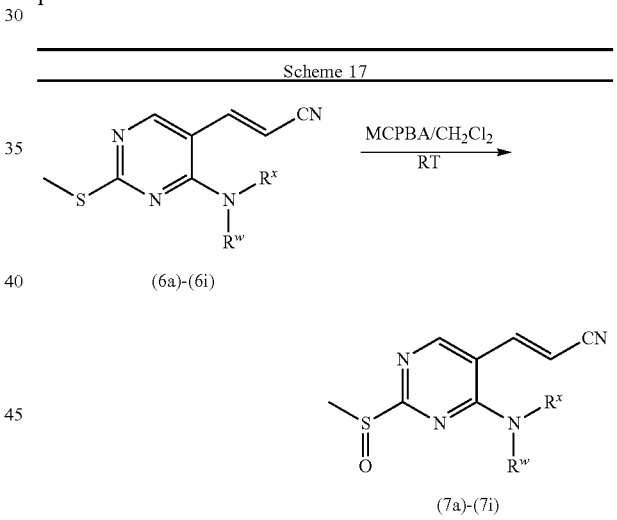

| | R$^w$ | R$^x$ |
|---|---|---|
| (7a) | H | |
| (7b) | methyl | |
| (7c) | ethyl | |
| (7d) | propyl | |
| (7e) | isopropyl | |
| (7f) | cyclopropylmethyl | |
| (7g) | cyclopropyl | |
| (7h) | cyclopentyl | |
| (7i) | cyclohexyl | |
| (7j) | methyl | ethyl |
| (7k) | —CH$_2$—CH$_2$—CH$_2$— | |
| (7l) | cyclopentyl | ethyl |
| (7m) | 1-methyl-1H-pyrazol-3-yl | H |

A solution of compound 6 (1 equiv.), and mCPBA (1.25 equiv.) in DCM was stirred at room temperature for about 12 h. After completion of the reaction, the reaction mixture was washed with saturated NaHCO$_3$, and the organic layer was dried over Na$_2$SO$_4$ and evaporated under reduced pressure to obtain the product 7, which was used for next reaction without further purification.

The following intermediate compounds were prepared by the method of General Procedure E described above.

Example 13. 3-[4-Amino-2-(methylsulfinyl)pyrimidin-5-yl]acrylonitrile (7a)

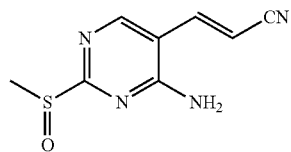
(7a)

Example 14. 3-[4-Methylamino-2-(methylsulfinyl)pyrimidin-5-yl]acrylonitrile (7b)

(7b)

Example 15. 3-[4-Ethylamino-2-(methylsulfinyl)pyrimidin-5-yl]acrylonitrile (7c)

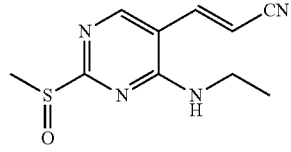
(7c)

Example 16. 3-[4-Propylamino-2-(methylsulfinyl)pyrimidin-5-yl]acrylonitrile (7d)

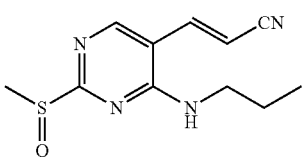
(7d)

Example 17. 3-[4-Isopropylamino-2-(methylsulfinyl)pyrimidin-5-yl]acrylonitrile (7e)

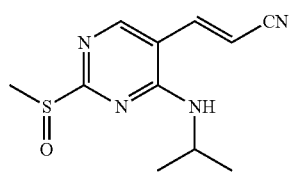
(7e)

Example 18. 3-[4-(Cyclopropylmethyl)amino-2-(methylsulfinyl)pyrimidin-5-yl]-acrylonitrile (7f)

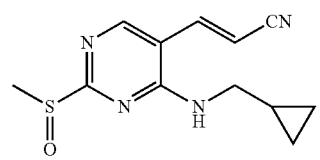
(7f)

Example 19. 3-[4-Cyclopropylamino-2-(methylsulfinyl)pyrimidin-5-yl]acrylonitrile (7g)

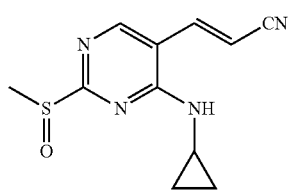
(7g)

Example 20. 3-[4-Cyclopentylamino-2-(methylsulfinyl)pyrimidin-5-yl]acrylonitrile (7h)

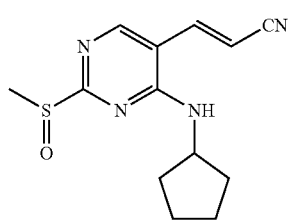
(7h)

Example 21. 3-[4-Cyclohexylamino-2-(methylsulfinyl)pyrimidin-5-yl]acrylonitrile (7i)

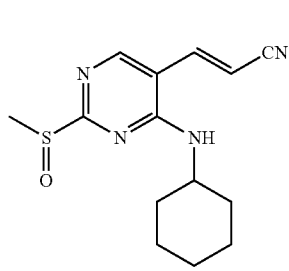

(7i)

Example 22. 3-[4-(N-Ethyl-N-methylamino)-2-(methylsulfinyl)pyrimidin-5-yl]acrylonitrile (7j)

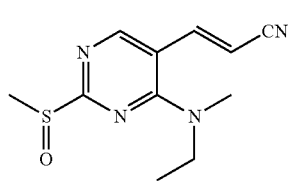

(7j)

Example 23. 3-(2-Methylsulfinyl-4-pyrrolidin-1-ylpyrimidin-5-yl)acrylonitrile (7k)

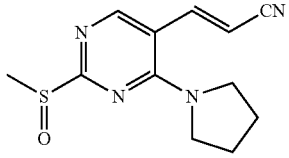

(7k)

Example 24. 3-[4-(N-Cyclopentyl-N-ethylamino)-2-(methylsulfinyl)pyrimidin-5-yl]acrylonitrile (7l)

(7l)

General Procedure G. Preparation of 3-[4-Alkylamino-2-(4-substituted-phenylamino)-pyrimidin-5-yl]-acrylonitrile (8a)-(8x) from Compounds (7a)-(7l)

Compounds (8a)-(8x) and (8z)-(8bb) were prepared by the procedure described below and illustrated in Scheme 18.

Scheme 18

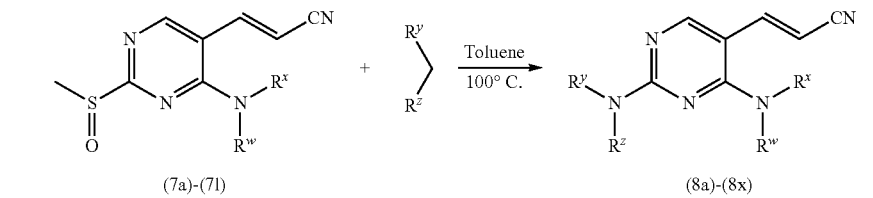

(7a)-(7l) → (8a)-(8x)

| | $R^w$ | $R^x$ | $R^y$ | $R^z$ |
|---|---|---|---|---|
| (8a) | H | H | 4-(4-methylpiperazin-1-yl)phenyl | H |
| (8b) | methyl | H | 4-(4-methylpiperazin-1-yl)phenyl | H |
| (8c) | ethyl | H | 4-(4-methylpiperazin-1-yl)phenyl | H |
| (8d) | propyl | H | 4-(4-methylpiperazin-1-yl)phenyl | H |
| (8e) | isopropyl | H | 4-(4-methylpiperazin-1-yl)phenyl | H |
| (8f) | cyclopropylmethyl | H | 4-(4-methylpiperazin-1-yl)phenyl | H |
| (8g) | cyclopropyl | H | 4-(4-methylpiperazin-1-yl)phenyl | H |
| (8h) | cyclopentyl | H | 4-(4-methylpiperazin-1-yl)phenyl | H |
| (8i) | cyclohexyl | H | 4-(4-methylpiperazin-1-yl)phenyl | H |
| (8j) | cyclopentyl | H | 4-(morpholin-4-yl)phenyl | H |
| (8k) | cyclopentyl | H | 1H-indol-5-yl | H |
| (8l) | cyclopentyl | H | 4-(1-methylpiperidin-4-yl)phenyl | H |

Scheme 18

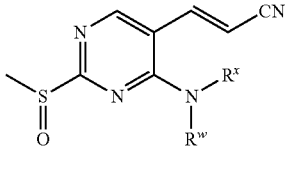

| | $R^w$ | $R^x$ | $R^y$ | $R^z$ |
|---|---|---|---|---|
| (8m) | methyl | H | 1H-indol-5-yl | H |
| (8n) | cyclopentyl | H | 4-methoxyphenyl | H |
| (8o) | cyclopentyl | H | 4-(4-ethylpiperazin-1-yl)phenyl | H |
| (8p) | cyclopentyl | H | benzyl | H |
| (8q) | cyclopentyl | H | 5-(1-methylpiperazin-4-yl)pyridin-2-yl | H |
| (8r) | cyclopropylmethyl | H | 4-(morpholin-4-yl)phenyl | H |
| (8s) | cyclopropylmethyl | H | 4-methoxyphenyl | H |
| (8t) | cyclopropylmethyl | H | 4-(4-ethylpiperazin-1-yl)phenyl | H |
| (8u) | cyclopropylmethyl | H | 1H-indol-5-yl | H |
| (8v) | methyl | ethyl | 4-methoxyphenyl | H |
| (8w) | —$CH_2$—$CH_2$—$CH_2$— | | 4-(4-ethylpiperazin-1-yl)phenyl | H |
| (8x) | cyclopentyl | ethyl | 1H-indol-5-yl | H |
| (8z) | cyclopentyl | H | —$CH_2$—$CH_2$—O—$CH_2$—$CH_2$— | |
| (8aa) | 1-methyl-1H-pyrazol-3-yl | H | 4-(4-methylpiperazin-1-yl)phenyl | H |
| (8bb) | 1-methyl-1H-pyrazol-3-yl | | 2-methoxy-4-(4-methylpiperazin-1-yl)phenyl | |

A mixture of compound 7 (1 equiv.) and an aromatic amine (1.2 equiv.) in toluene was stirred at 100° C. overnight. The reaction mixture was cooled and solids were collected by filtration and the product 8 was purified flash column chromatography on silica gel using 2-4% methanol in chloroform as the eluant.

Example 25. 3-{4-Amino-2-[4-(4-methylpiperazin-1-yl)phenylamino]pyrimidin-5-yl}acrylonitrile (8a)

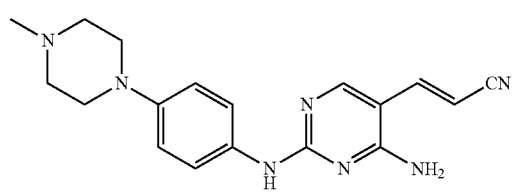

(8a)

Starting from compound (7a) and 4-(4-methylpiperazin-1-yl)aniline, compound (8a) was obtained in 40% yield using the method described in General Procedure G. m.p.>300° C.; $^1$H NMR (300 MHz, DMSO-$d_6$), δ 2.22 (s, N—$CH_3$, 3H), 2.54 (bs, 2$CH_2$, 4H), 3.35 (bs, 2$CH_2$, 4H), 6.04 (d, =CH, J=16.8 Hz, 1H), 7.02-6.85 (m, $NH_2$ & 2Ar—H, 4H), 7.55-7.85 (m, =CH & 2Ar—H, 3H), 8.37 (s, Ar—H, 1H), 9.25 (bs, NH, 1H).

Example 26. 3-{4-Methylamino-2-[4-(4-methylpiperazin-1-yl)-phenylamino]pyrimidin-5-yl}acrylonitrile (8b)

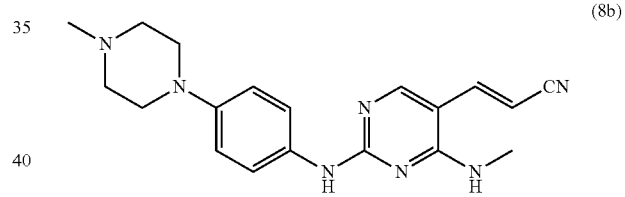

(8b)

Starting from compound (7b) and 4-(4-methylpiperazin-1-yl)aniline, compound (8b) was obtained in 45% yield using the method described in General Procedure G. m.p.>300° C.; $^1$H NMR (300 MHz, DMSO-$d_6$), δ 2.23 (s, N—$CH_3$, 3H), 2.50 (bs, 2$CH_2$, 4H), 2.88 (d, NH—$CH_3$, 3H), 3.06 (bs, 2$CH_2$, 4H), 6.04 (d, =CH, J=16.2 Hz, 1H), 6.86 (d, Ar—H, J=9.0 Hz, 2H), 7.40 (bs, NH, 1H), 7.64-7.55 (m, =CH, & Ar—H, 3H), 8.32 (s, Ar—H, 1H), 9.35 (bs, NH, 1H).

Example 27. 3-{4-Ethylamino-2-[4-(4-methylpiperazin-1-yl)phenylamino]pyrimidin-5-yl}acrylonitrile (8c)

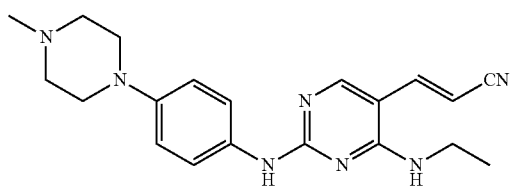

(8c)

Starting from compound (7c) and 4-(4-methylpiperazin-1-yl)aniline, compound (8c) was obtained in 47% yield using the method described in General Procedure G. m.p.>300° C.; $^1$H NMR (300 MHz, CDCl$_3$), δ 1.31 (t, —CH$_2$CH$_3$, 3H), 2.23 (s, N—CH$_3$, 3H), 2.62-2.59 (m, 2CH$_2$, 4H), 3.21-3.18 (m, 2CH$_2$, 4H), 3.61-3.52 (m, N—CH$_2$CH$_3$, 2H), 4.90 (bs, NH, 1H), 5.57 (d, =CH, J=16.2 Hz, 1H), 6.93 (d, Ar—H, J=9.0 Hz, 2H), 7.03 (d, NH, 1H), 7.20 (d, =CH, J=16.2 Hz, 1H), 7.50 (d, Ar—H, J=9.0 Hz, 2H), 8.08 (s, Ar—H, 1H).

Example 28. 3-{4-Propylamino-2-[4-(4-methylpiperazin-1-yl)phenylamino]pyrimidin-5-yl}acrylonitrile (8d)

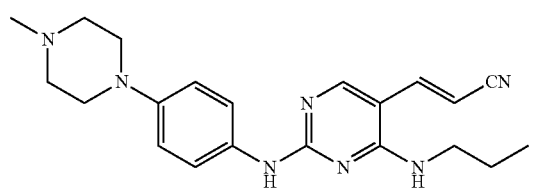

(8d)

Starting from compound (7d) and 4-(4-methylpiperazin-1-yl)aniline, compound (8d) was obtained in 45% yield using the method described in General Procedure G. m.p.>300° C.; $^1$H NMR (300 MHz, CDCl$_3$), δ 1.02 (t, N—CH$_2$CH$_2$CH$_3$, 3H), 1.74-1.66 (m, N—CH$_2$CH$_2$CH$_3$, 2H), 2.34 (s, N—CH$_3$, 3H), 2.61 (bs, 2CH$_2$, 4H), 3.22 (bs, 2CH$_2$, 4H), 3.52-3.45 (m, N—CH$_2$CH$_2$CH$_3$, 2H), 5.02 (bs, NH, 1H), 5.55 (d, =CH, J=15.9 Hz, 1H), 6.93 (d, Ar—H, J=8.7 Hz, 2H), 7.09 (bs, NH, 1H), 7.22 (d, =CH, J=16.2 Hz, 1H), 7.50 (d, Ar—H, J=8.4 Hz, 2H), 8.05 (s, Ar—H, 1H).

Example 29. 3-{4-Isopropylamino-2-[4-(4-methylpiperazin-1-yl)phenylamino]pyrimidin-5-yl}acrylonitrile (8e)

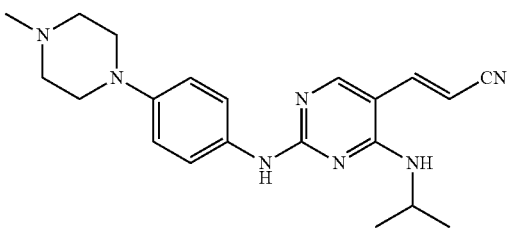

(8e)

Starting from compound (7e) and 4-(4-methylpiperazin-1-yl)aniline, compound (8e) was obtained in 43% yield using the method described in General Procedure G. m.p.>300° C.; $^1$H NMR (300 MHz, DMSO-d$_6$), δ 1.20 (d, CH—(CH$_3$)$_2$, 6H), 2.22 (s, N—CH$_3$, 3H), 2.47-2.43 (m, 2CH$_2$, 4H), 3.09-3.04 (m, 2CH$_2$, 4H), 4.35-5.26 (m, N—CH—, 1H), 6.03 (d, =CH, J=16.2 Hz, 1H), 6.85 (d, Ar—H, J=9.0 Hz, 2H), 7.09 (d, NH, 1H), 7.61 (d, Ar—H, J=9.0 Hz, 2H), 6.73 (d, =CH, J=16.2 Hz, 1H), 8.35 (s, Ar—H, 1H), 9.32 (bs, NH, 1H).

Example 30. 3-{4-(Cyclopropylmethyl)amino-2-[4-(4-methylpiperazin-1-yl)phenylamino]pyrimidin-5-yl}acrylonitrile (8f)

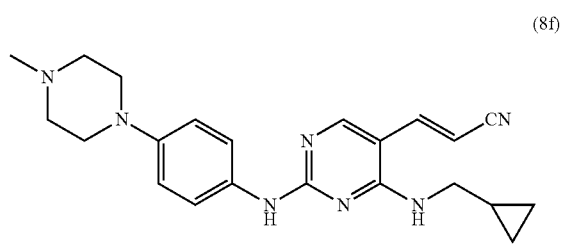 [SMILES: CN1CCN(c2ccc(Nc3ncc(/C=C/C#N)c(NCC4CC4)n3)cc2)CC1]

(8f)

Starting from compound (7f) and 4-(4-methylpiperazin-1-yl)aniline, compound (8f) was obtained in 45% yield using the method described in General Procedure G. m.p.>300° C.; $^1$H NMR (300 MHz, DMSO-d$_6$), δ 0.014-0.00 (m, CH$_2$, 2H), 0.22-0.20 (m, CH$_2$, 2H), 0.91-0.87 (m, N—CH$_2$—CH—, 1H), 1.98 (s, N—CH$_3$, 3H), 2.26 (bs, 2CH$_2$, 4H), 2.81 (bs, 2CH$_2$, 4H), 3.05-3.03 (m, N—CH$_2$—, 2H), 5.79 (d, =CH, J=16.2 Hz, 1H), 6.61 (d, Ar—H, J=9.3 Hz, 2H), 7.27 (bs, NH, 1H), 7.35 (d, Ar—H, J=8.7 Hz, 2H), 6.43 (d, =CH, J=16.2 Hz, 1H), 8.11 (s, Ar—H, 1H), 9.09 (bs, NH, 1H).

Example 31. 3-{4-Cyclopropylamino-2-[4-(4-methylpiperazin-1-yl)phenylamino]pyrimidin-5-yl}acrylonitrile (8g)

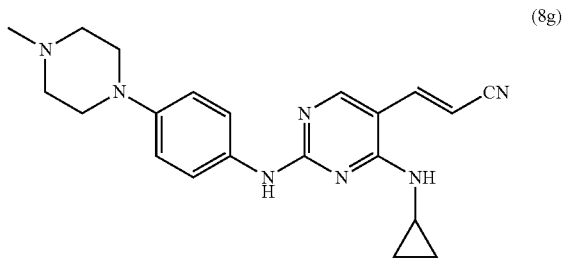 [SMILES: CN1CCN(c2ccc(Nc3ncc(/C=C/C#N)c(NC4CC4)n3)cc2)CC1]

(8g)

Starting from compound (7g) and 4-(4-methylpiperazin-1-yl)aniline, compound (8g) was obtained in 40% yield using the method described in General Procedure G. m.p.>300° C.; $^1$H NMR (300 MHz, CDCl$_3$), δ 0.60-0.57 (m, CH$_2$, 2H), 0.80-0.78 (m, CH$_2$, 2H), 2.23 (s, N—CH$_3$, 3H), 2.50-2.47 (m, 2CH$_2$, 4H), 2.89-2.86 (m, N—CH—, 1H), 3.06-3.03 (m, 2CH$_2$, 4H), 6.04 (d, =CH, J=16.5 Hz, 1H), 6.86 (d, Ar—H, J=9.3 Hz, 2H), 7.51 (d, NH, 1H), 7.64 (d, =CH, J=16.2 Hz, 1H), 7.78 (d, Ar—H, J=9.0 Hz, 2H), 8.36 (s, Ar—H, 1H), 9.43 (bs, NH, 1H).

Example 32. 3-{4-Cyclopentylamino-2-[4-(4-methylpiperazin-1-yl)phenylamino]pyrimidin-5-yl}acrylonitrile (8h)

Example 34. 3-{4-Cyclopentylamino-2-[(4-morpholin-4-yl)phenylamino]pyrimidin-5-yl}acrylonitrile (8j)

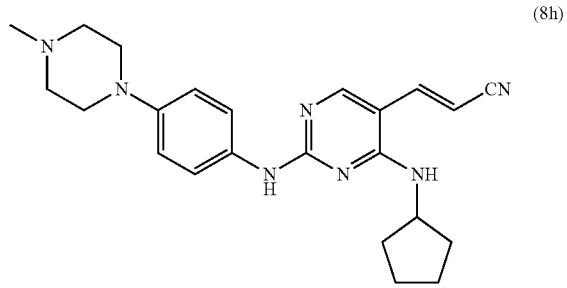 [SMILES: CN1CCN(c2ccc(Nc3ncc(/C=C/C#N)c(NC4CCCC4)n3)cc2)CC1]

(8h)

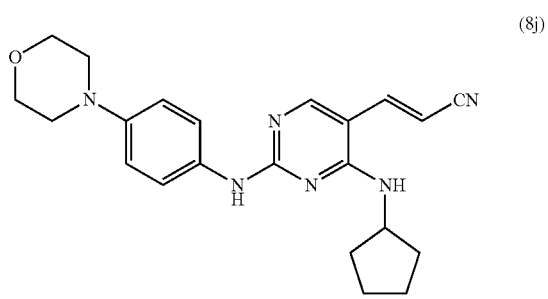 [SMILES: N#C/C=C/c1cnc(Nc2ccc(N3CCOCC3)cc2)nc1NC1CCCC1]

(8j)

Starting from compound (7h) and 4-(4-methylpiperazin-1-yl)aniline, compound (8h) was obtained in 48% yield using the method described in General Procedure G. m.p.>300° C.; $^1$H NMR (300 MHz, DMSO-d$_6$), δ 1.71-1.56 (m, 3CH$_2$, 6H), 2.00-1.95 (m, CH$_2$, 2H), 2.23 (s, N—CH$_3$, 3H), 2.55 (bs, 2CH$_2$, 4H), 3.06 (bs, 2CH$_2$, 4H), 4.39-4.37 (m, N—CH—, 1H), 6.03 (d, =CH, J=15.9 Hz, 1H), 6.85 (d, Ar—H, J=9.0 Hz, 2H), 7.15 (d, NH, 1H), 7.62 (d, Ar—H, J=8.7 Hz, 2H), 6.77 (d, =CH, J=16.2 Hz, 1H), 8.34 (s, Ar—H, 1H), 9.32 (bs, NH, 1H).

Starting from compound (7h) and 4-(morpholin-4-yl)aniline, compound (8j) was obtained in 43% yield using the method described in General Procedure G. m.p.>300° C.; $^1$H NMR (300 MHz, DMSO-d$_6$), δ 1.56 (bs, 2CH$_2$, 4H), 1.71 (bs, CH$_2$, 2H), 1.97 (bs, CH$_2$, 2H), 3.04-3.01 (m, 2CH$_2$, 4H), 3.74-3.71 (m, 2CH$_2$, 4H), 4.39-4.37 (bs, N—CH—, 1H), 6.04 (d, =CH, J=16.2 Hz, 1H), 6.86 (d, Ar—H, J=9.0 Hz, 2H), 7.17 (d, NH, 1H), 7.63 (d, Ar—H, J=9.3 Hz, 2H), 6.76 (d, =CH, J=16.2 Hz, 1H), 8.35 (s, Ar—H, 1H), 9.35 (bs, NH, 1H).

Example 33. 3-{4-Cyclohexylamino-2-[4-(4-methylpiperazin-1-yl)phenylamino]pyrimidin-5-yl}acrylonitrile (8i)

Example 35. 3-[4-Cyclopentylamino-2-(1H-indol-5-ylamino)pyrimidin-5-yl]acrylonitrile (8k)

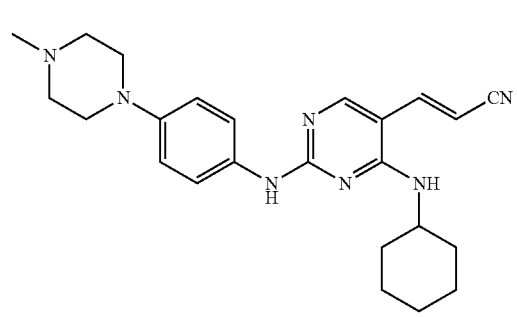

(8i)

(8k)

Starting from compound (7i) and 4-(4-methylpiperazin-1-yl)aniline, compound (8i) was obtained in 43% yield using the method described in General Procedure G. m.p.>300° C.; $^1$H NMR (300 MHz, DMSO-d$_6$), δ 1.36-1.23 (m, 3CH$_2$, 6H), 1.95-1.93 (m, 2CH$_2$, 4H), 2.22 (s, N—CH$_3$, 3H), 2.46-2.43 (m, 2CH$_2$, 4H), 3.06-3.03 (m, 2CH$_2$, 4H), 4.00 (bs, N—CH—, 1H), 6.02 (d, =CH, J=16.2 Hz, 1H), 6.84 (d, Ar—H, J=9.3 Hz, 2H), 7.10 (d, NH, 1H), 7.61 (d, Ar—H, J=9.0 Hz, 2H), 6.74 (d, =CH, J=16.2 Hz, 1H), 8.34 (s, Ar—H, 1H), 9.32 (bs, NH, 1H).

Starting from compound (7h) and 5-aminoindole, compound (8k) was obtained in 43% yield using the method described in General Procedure G. m.p. 225-227° C.; $^1$H NMR (300 MHz, CDCl$_3$), δ 1.54-1.50 (m, CH$_2$, 2H), 1.72-1.68 (m, 2CH$_2$, 4H), 2.19-2.14 (m, CH$_2$, 2H), 4.50-4.43 (bs, N—CH—, 1H), 4.90 (d, NH, 1H), 5.55 (d, =CH, J=16.5 Hz, 1H), 6.52-6.51 (m, Ar—H, 1H), 6.37-7.17 (m, 4Ar—H, & =CH, 5H), 8.02 (bs, NH, 1H), 8.09 (s, Ar—H, 1H), 8.18 (bs, NH, 1H).

Example 36. 3-{4-Cyclopentylamino-2-[4-(1-methylpiperidin-4-yl)phenylamino]pyrimidin-5-yl}acrylonitrile (8l)

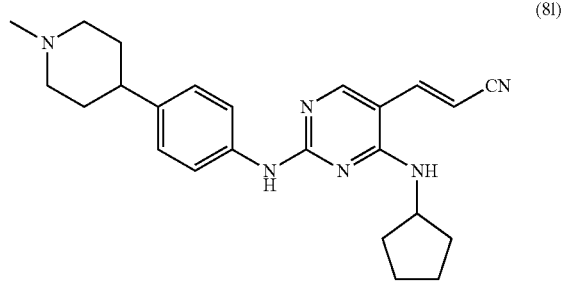 [SMILES: CN1CCC(c2ccc(Nc3ncc(/C=C/C#N)c(NC4CCCC4)n3)cc2)CC1]

Starting from compound (7h) and 4-(1-methylpiperidine-4-yl)aniline, compound (8l) was obtained in 43% yield using the method described in General Procedure G. m.p.>300° C.; ¹H NMR (300 MHz, DMSO-d₆), δ 1.28-1.20 (m, CH₂, 2H), 1.56-1.48 (m, 2CH₂, 4H), 1.70-1.66 (m, 2CH₂, 4H), 1.97-1.96 (m, CH₂, 2H), 2.49 (s, N—CH₃, 3H), 2.59-2.55 (m, Ar—C—CH, 1H), 3.33 (bs, CH₂, 2H), 3.56-3.52 (bs, CH₂, 2H), 4.38-4.36 (m, N—CH—, 1H), 6.03 (d, =CH, J=16.2 Hz, 1H), 6.84 (d, Ar—H, J=9.0 Hz, 2H), 7.13 (d, NH, 1H), 7.59 (d, Ar—H, J=9.0 Hz, 2H), 7.75 (d, =CH, J=16.5 Hz, 1H), 8.34 (s, Ar—H, 1H), 9.31 (bs, NH, 1H).

Example 37. 3-[2-(1H-Indol-5-ylamino)-4-(methylamino)pyrimidin-5-yl]acrylonitrile (8m)

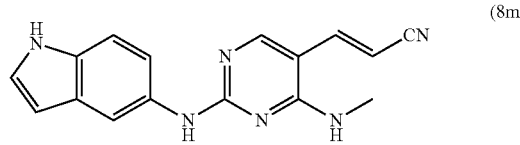

Starting from compound (7b) and 5-aminoindole, compound (8m) was obtained in 45% using the method described in General Procedure G. ¹H NMR (300 MHz, DMSO-d₆), δ 2.92 (d, N—CH₃, 3H), 6.04 (d, =CH, J=16.2 Hz, 1H), 6.33 (bs, Ar—H, 1H), 7.27-7.18 (m, Ar—H, 2H), 7.41-7.38 (m, 2H, Ar—H, 2H), 7.61 (d, =CH, J=16.2 Hz, 1H), 8.04 (bs, NH, 1H), 8.34 (s, Ar—H, 1H), 9.37 (bs, NH, 1H).

Example 38. 3-{4-(Cyclopentylamino)-2-[(4-methoxyphenyl)amino]pyrimidin-5-yl)acrylonitrile (8n)

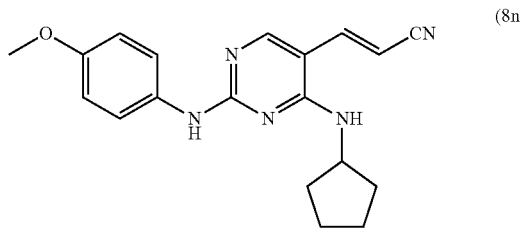

Starting from compound (7h) and 4-methoxyaniline, compound (8n) was obtained in 60% yield using the method described in General Procedure G. ¹H NMR (300 MHz, DMSO-d₆), δ 1.56 (bs, CH₂, 4H), 1.71 (bs, CH₂, 2H), 1.97 (bs, CH₂, 2H), 3.71 (s, OCH₃, 3H), 4.38-4.36 (m, NH—CH, 1H), 6.04 (d, =CH, J=16.2 Hz, 1H), 6.84 (d, Ar—H, J=9.0 Hz, 2H), 7.18 (d, NH, 1H), 7.66 (d, Ar—H, J=9.0 Hz, 2H), 7.76 (d, =CH, J=16.2 Hz, 1H), 8.36 (s, Ar—H, 1H), 9.39 (bs, NH, 1H).

Example 39. 3-{4-Cyclopentylamino-2-[4-(1-ethylpiperazin-4-yl)-phenylamino]-pyrimidin-5-yl}acrylonitrile (8o)

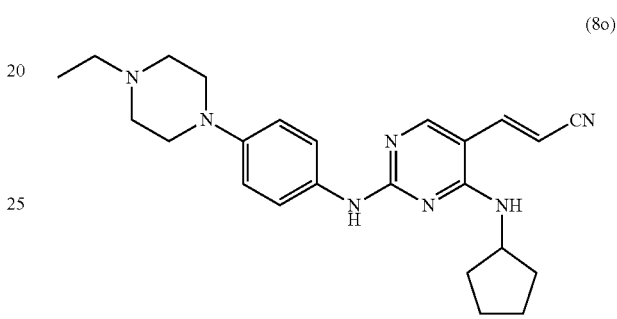

Starting from compound (7h) and 4-(1-ethylpiperidine-4-yl)aniline, compound (8o) was obtained in 45% yield using the method described in General Procedure G. ¹H NMR (300 MHz, DMSO-d₆), δ 1.03 (t, CH₃, 3H), 1.56 (bs, 2CH₂, 4H), 1.72 (bs, CH₂, 2H), 1.97 (bs, CH₂, 2H), 2.5 (bs, 2CH₂, 4H), 3.06 (bs, 2CH₂, 4H), 4.38 (bs, N—CH—, 1H), 6.03 (d, =CH, J=16.2 Hz, 1H), 6.85 (d, Ar—H, J=8.1 Hz, 2H), 7.17 (bs, NH, 1H), 7.62 (d, Ar—H, J=7.5 Hz, 2H), 7.76 (d, =CH, J=16.5 Hz, 1H), 8.35 (s, Ar—H, 1H), 9.33 (bs, NH, 1H).

Example 40. 3-[2-(Benzylamino)-4-(cyclopentylamino)pyrimidin-5-yl]acrylonitrile (8p)

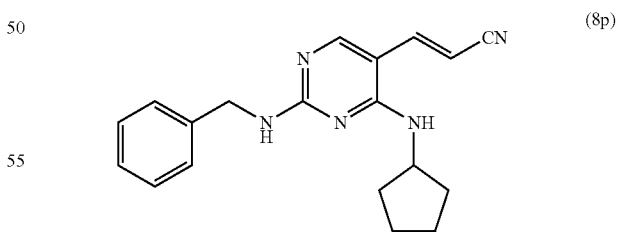

Starting from compound (7h) and benzylamine, compound (8p) was obtained in 50% yield using the method described in General Procedure G. ¹H NMR (300 MHz, DMSO-d₆), δ 1.88-1.48 (m, 4CH₂, 8H), 4.45 (bs, CH₂, 2H), 5.92 (d, =CH, J=15.9 Hz, 6.98 (bs, NH, 1H), 7.29-7.18 (m, Ar—H, 5H), 7.69 (d, =CH, J=16.2 Hz, 1H), 7.84 (bs, NH, 1H), 8.24 (s, Ar—H, 1H).

Example 41. 3-(4-(Cyclopentylamino)-2-((5-(4-methylpiperazin-1-yl)pyridin-2-yl)amino)pyrimidin-5-yl)acrylonitrile (8q)

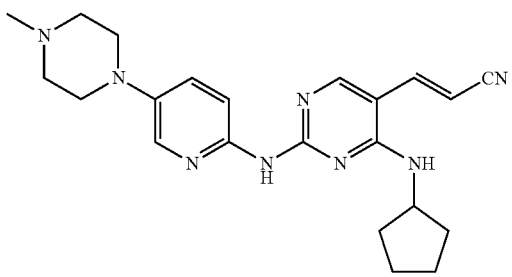

(8q)

Starting from compound (7h), and 2-amino-5-(4-methylpiperazin-1-yl)pyridine, compound (8q) was obtained in 50% yield using the method described in General Procedure G. $^1$H NMR (300 MHz, DMSO-d$_6$), δ 1.59-1.53 (m, 2CH$_2$, 4H), 1.70 (bs, CH$_2$, 2H), 1.91 (bs, CH$_2$, 2H), 2.20 (s, N—CH$_3$, 3H), 2.36-2.20 (m, 2CH$_2$, 4H), 3.67-3.63 (m, 2CH$_2$, 4H), 4.29 (bs, N—CH—, 1H), 6.06 (d, =CH, J=16.2 Hz, 1H), 7.20 (d, Ar—H, J=8.8 Hz, 1H), 7.74 (d, =CH, J=16.2 Hz, 1H), 8.31 (d, Ar—H, J=6.2 Hz, 1H), 8.64 (bs, Ar—H, 2H), 9.31 (bs, NH, 1H).

Example 42. 3-{4-[N-(Cyclopropylmethyl)amino]-2-[4-(morpholin-4-yl)phenylamino]pyrimidin-5-yl}acrylonitrile (8r)

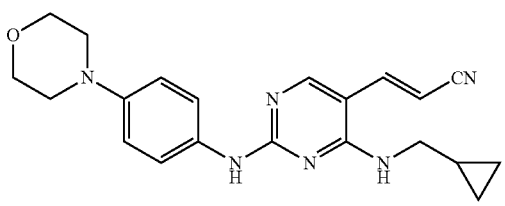

(8r)

Starting from compound (7f), and 4-(morpholin-4-yl)aniline, compound (8r) was obtained in 50% yield using the method described in General Procedure G. $^1$H NMR (300 MHz, CDCl$_3$), δ 0.32-0.30 (m, CH$_2$, 2H), 0.64-0.62 (m, CH$_2$, 2H), 1.14 (bs, C—H, 1H), 3.15 (bs, 2CH$_2$, 4H), 3.39-3.35 (m, CH$_2$, 2H), 3.89 (bs, 2CH$_2$, 4H), 5.03 (bs, NH, 1H), 5.60 (d, =CH, J=16.5 Hz, 1H), 6.92 (d, Ar—H, J=7.4 Hz, 2H), 7.02 (d, NH, 1H), 7.29 (d, =CH, J=16.2 Hz, 1H), 7.50 (d, Ar—H, J=7.4 Hz, 2H), 8.09 (s, Ar—H, 1H).

Example 43. 3-{4-(Cyclopentylamino)-2-[(4-methoxyphenyl)amino]pyrimidin-5-yl)acrylonitrile (8s)

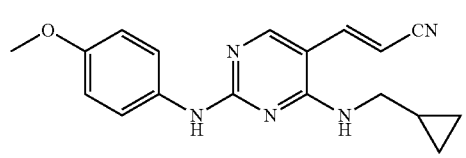

(8s)

Starting from compound (6f) and 4-methoxyaniline, compound (8s) was obtained in 50% yield using the method described in General Procedure G. $^1$H NMR (300 MHz, DMSO-d$_6$), δ 0.01 (bs, CH$_2$, 2H), 0.22-0.20 (m, CH$_2$, 2H), 0.89 (bs, C—H, 1H), 3.03-3.01 (m, CH$_2$, 2H), 3.48 (s, OCH$_3$, 3H), 5.81 (d, =CH, J=15.9 Hz, 1H), 6.60 (d, Ar—H, J=8.7 Hz, 2H), 7.29 (bs, NH, 1H), 7.48-7.39 (m, Ar—H & =CH, 3H), 8.12 (s, Ar—H, 1H), 9.14 (s, NH, 1H).

Example 44. 3-{4-[(Cyclopropylmethyl)amino]-2-[4-(4-ethylpiperazin-1-yl)phenylamino]pyrimidin-5-yl}acrylonitrile (8t)

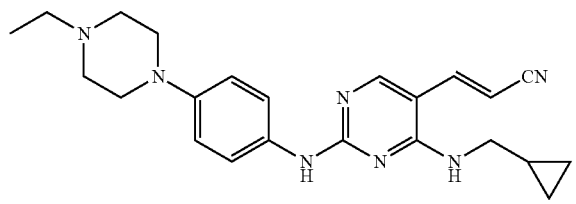

(8t)

Starting from compound (7f) and 4-(4-ethylpiperazin-1-yl)aniline, compound (8t) was obtained in 50% yield using the method described in General Procedure G. $^1$H NMR (300 MHz, DMSO-d$_6$), δ 0.013 (bs, CH$_2$, 2H), 0.22-0.199 (m, CH$_2$, 2H), 0.81-0.76 (t, CH$_3$, 3H), 0.89-0.85 (m, C—H, 1H), 2.15-2.06 (m, CH$_2$, 2H), 2.26 (bs, CH$_2$, 2H), 2.81 (bs, 2CH$_2$, 4H), 3.09-3.01 (m, 2CH$_2$, 4H), 5.79 (d, =CH, J=16.2 Hz, 1H), 6.60 (d, Ar—H, J=8.7 Hz, 2H), 7.26 (bs, NH, 1H), 7.35 (d, Ar—H, J=8.7 Hz, 2H), 7.43 (d, =CH, J=16.2 Hz, 1H), 8.10 (s, Ar—H, 1H), 9.07 (bs, NH, 1H).

Example 45. 3-{4-[(Cyclopropylmethyl)amino]-2-[(1H-indol-5-yl)amino]pyrimidin-5-yl)acrylonitrile (8u)

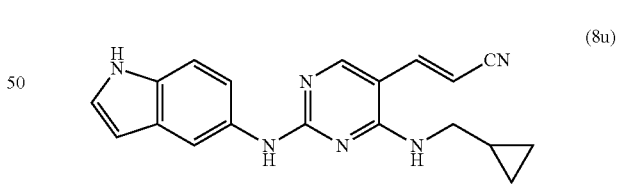

(8u)

Starting from compound (7f) and 5-aminoindole, compound (8u) was obtained in 50% yield using the method described in General Procedure G. $^1$H NMR (300 MHz, DMSO-d$_6$), δ 0.27-0.27 (m, CH$_2$, 2H), 0.47-0.44 (m, CH$_2$, 2H), 1.18 (bs, C—H, 1H), 3.36 (bs, CH$_2$, 2H), 6.05 (d, =CH, J=16.2 Hz, 1H), 6.31 (s, Ar—H, 1H), 7.34-7.25 (m, Ar—H, 3H), 7.53 (bs, NH, 1H), 7.69 (d, =CH, J=16.2 Hz, 1H), 8.07 (s, Ar—H, 1H), 8.37 (s, Ar—H, 1H), 9.35 (bs, NH, 1H), 10.92 (bs, NH, 1H).

Example 46. 3-{4-(N-Ethyl-N-methylamino)-2-[4-(4-methylpiperazin-1-yl)phenylamino]pyrimidin-5-yl}acrylonitrile (8v)

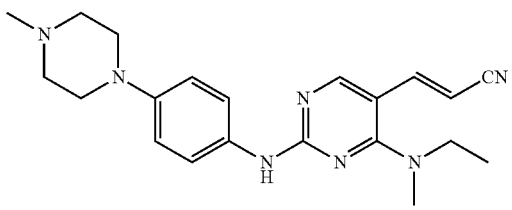

Starting from compound (7j) and 4-(4-methylpiperazin-1-yl)aniline, compound (8v) was obtained in 50% yield using the method described in General Procedure G. $^1$H NMR (300 MHz, CDCl$_3$), δ 1.25 (t, CH$_3$, 3H), 2.36 (s, N—CH$_3$, 3H), 2.61-2.58 (bs, 2CH$_2$, 4H), 3.05 (s, N—CH$_3$, 3H), 3.20-3.05 (bs, 2CH$_2$, 4H), 3.50 (q, —CH$_2$—, 2H), 5.44 (d, =CH, J=16.2 Hz, 1H), 6.92 (d, Ar—H, J=9.0 Hz, 2H), 7.35 (d, =CH, J=16.2 Hz, 1H), 7.47 (d, Ar—H, J=9 Hz, 2H), 8.07 (s, Ar—H, 1H), 9.32 (bs, NH, 1H).

Example 47. 3-{2-[4-(4-Methylpiperazin-1-yl)phenylamino]-4-(pyrrolidin-1-yl)pyrimidin-5-yl}acrylonitrile (8w)

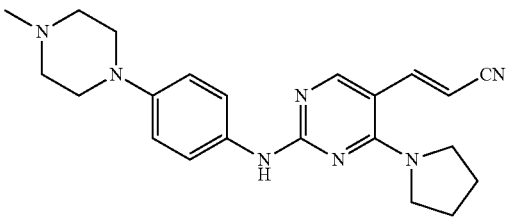

Starting from v(7k) and 4-(4-methylpiperazin-1-yl)aniline, compound (8w) was obtained in 50% yield using the method described in General Procedure G. $^1$H NMR (300 MHz, CDCl$_3$), δ 2.00-1.95 (m, 2CH$_2$, 4H), 2.27 (s, N—CH$_3$, 3H), 2.62-2.58 (m, 2CH$_2$, 4H), 3.20-3.17 (m, 2CH$_2$, 4H), 3.68-3.63 (m, 2CH$_2$, 4H), 5.40 (d, =CH, J=16.2 Hz, 1H), 6.92 (d, Ar—H, J=9.0 Hz, 2H), 7.21 (d, NH, 1H), 7.50 (d, Ar—H, J=9.0 Hz, 2H), 6.61 (d, =CH, J=16.2 Hz, 1H), 8.08 (s, Ar—H, 1H).

Example 48. 3-{4-(N-Cyclopentyl-N-ethylamino)-2-[4-(4-methylpiperazin-1-yl)phenylamino]pyrimidin-5-yl}acrylonitrile (8x)

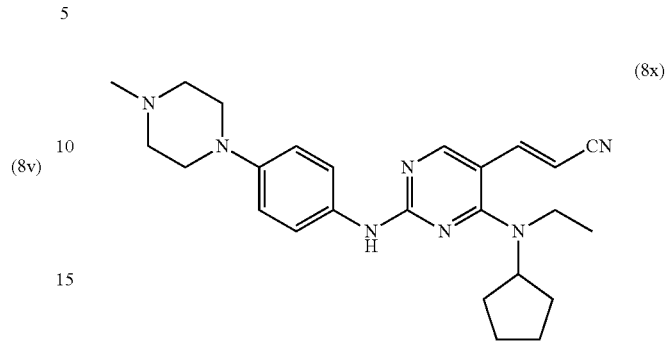

Starting from compound (7l), and 4-(4-methyl-piperazin-1-yl)aniline, compound (8x) was obtained in 50% yield using the method described in General Procedure G. $^1$H NMR (300 MHz, CDCl$_3$), δ 1.18 (t, CH$_3$, 3H), 1.90-1.58 (m, 4CH$_2$, 8H), 2.37 (s, N—CH$_3$, 3H), 2.62-2.58 (m, 2CH$_2$, 4H), 3.21-3.17 (m, 2CH$_2$, 4H), 3.47-3.40 (q, CH$_2$, 2H), 4.20-4.15 (m, N—CH—, 1H), 5.55 (d, =CH, J=16.2 Hz, 1H), 6.93 (d, Ar—H, J=7.7 Hz, 2H), 7.29 (d, =CH, J=16.5 Hz, 1H), 7.46 (d, Ar—H, J=9.0 Hz, 2H), 8.10 (s, Ar—H, 1H), 9.30 (bs, NH, 1H).

Example 49. N-[5-(2-Cyanovinyl)-4-(cyclopentylamino)pyrimidin-2-yl]-N-[4-(4-methylpiperazin-1-yl)phenyl]-5-((3aS,4S,6aR)-2-oxohexahydro-1H-thieno[3,4-d]imidazol-4-yl)pentanamide (8y)

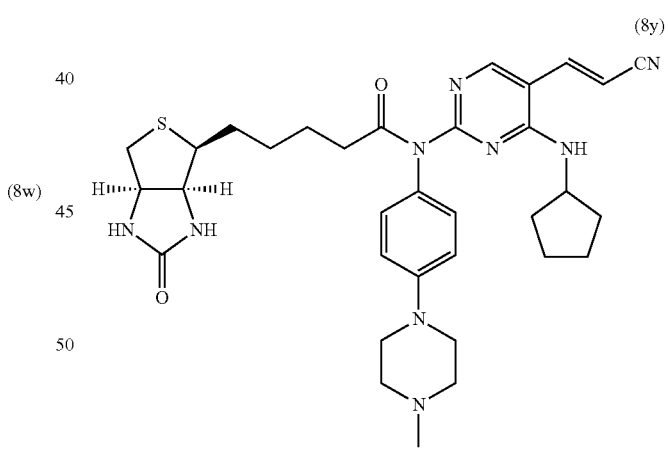

Biotin (1.22 mmol), EDC (2.4 mmol), DMAP (1.22 mmol) were taken in to DMF (40 mL) and stirred at RT for 10 min. Compound (8h) (1.22 mmol) was added to the reaction mixture and stirring was continued for 6 h. The reaction mixture was diluted with water and extracted with DCM, and dried over Na$_2$SO$_4$ and the solvent was removed under reduced pressure. The crude product was purified by flash column chromatography. $^1$H NMR (300 MHz, CDCl$_3$), δ 1.35-1.32 (m, CH, 2H), 1.88-1.61 (m, 6CH$_2$, 12H), 1.92-1.88 (m, CH$_2$, 2H), 2.38 (s, N—CH$_3$, 3H), 2.62-2.59 (m, 2CH$_2$, 4H), 3.18-3.16 (m, C—H, 1H), 3.26-3.23 (m, 2CH$_2$, 4H), 4.14-4.10 (m, C—H, 1H), 4.36-4.32 (m, C—H, 1H), 4.54-4.50 (m, C—H, 1H), 4.73 (bs, NH, 1H), 5.04 (bs, NH, 1H), 5.26 (bs, NH, 1H), 5.78 (d, =CH, J=16.5 Hz, 1H), 6.93 (d, Ar—H, J=9.0 Hz, 2H), 7.12 (d, Ar—H, J=9.0 Hz, 2H), 7.21 (d, =CH, J=16.5 Hz, 1H), 8.26 (s, Ar—H, 1H).

General Procedure H. Preparation of Arylsulfanylmethylphosphonic acid Diethyl Esters (11)

Compounds (11a) and (11b) were prepared by the procedure described below and illustrated in Scheme 19.

Scheme 19

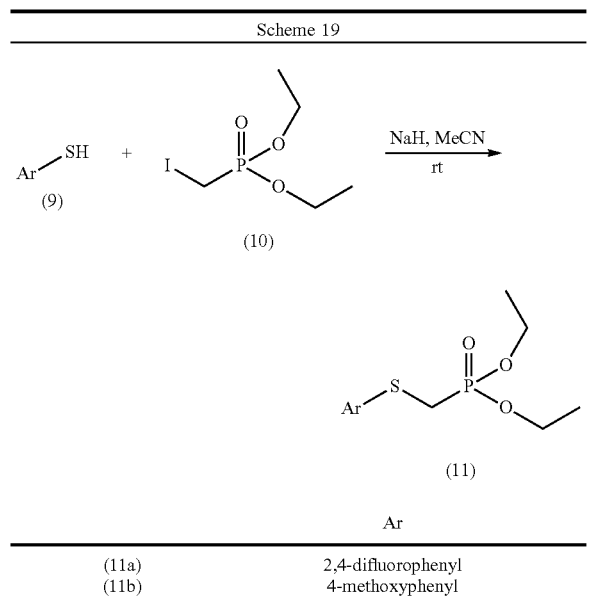

| | Ar |
|---|---|
| (11a) | 2,4-difluorophenyl |
| (11b) | 4-methoxyphenyl |

To a room temperature solution of NaH (60% in mineral oil, 1.2 equiv.) in acetonitrile under an argon atmosphere, arylthiol (9) (1 equiv.) was added dropwise. After 30 min., iodomethyldiethylphophonate (10) (1.1 mmol) was added and the mixture was stirred at room temperature overnight. After quenching the reaction with water, the mixture was extracted with ethyl acetate. The combined organic layers were dried over Na$_2$SO$_4$ and evaporated to afford the corresponding sulfane (11), which was used directly in the next step.

Preparation 31.
(2,4-Difluorophenylsulfanylmethyl)-phosphonic acid diethyl ester (11a)

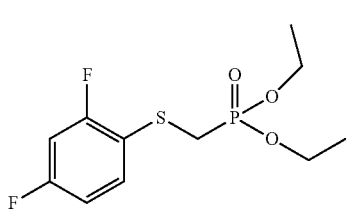

Starting from 2,4-difluorobenzenethiol (9a) and iodomethyldiethylphophonate (10), compound (11a) was obtained in 75% using the method described in General Procedure H. $^1$H NMR (300 MHz, CDCl$_3$), δ 7.52-7.45 (m, Ar—H, 1H), 6.82-6.75 (m, Ar—H, 2H), 4.06-3.99 (m, —OCH$_2$—, 4H), 3.03 (d, P—CH$_2$—, J=13.2 Hz, 2H), 0.83-0.76 (m, —CH$_3$, 6H).

General Procedure I. Synthesis of Arylsulfonylmethylphosphonic Acid Diethyl Ester (12)

Compounds (12a) and (12b) were prepared by the procedure described below and illustrated in Scheme 20.

Scheme 20

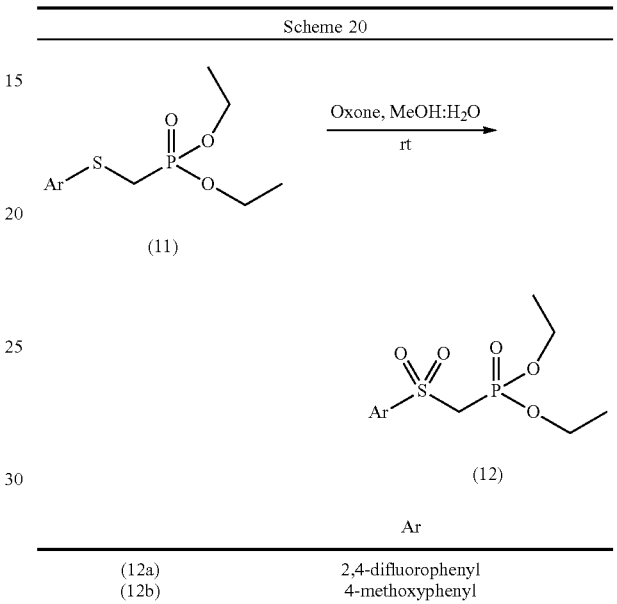

| | Ar |
|---|---|
| (12a) | 2,4-difluorophenyl |
| (12b) | 4-methoxyphenyl |

To a stirred solution of sulfane (11) (1 equiv.) in a 1/1 mixture MeOH/H$_2$O was slowly added potassium peroxymonosulfate (10 equiv.) and the corresponding mixture was stirred at room temperature overnight. Then, the MeOH was evaporated, the residue was dissolved in DCM and filtered through diatomaceous earth. Water was added to the resulting solution and the mixture was extracted with DCM. The organic phase was washed with brine and dried over Na$_2$SO$_4$. The crude product was purified by flash chromatography to give pure compound (12).

Preparation 32.
(2,4-difluorobenzenesulfonylmethyl)phosphonic acid diethyl ester (12a)

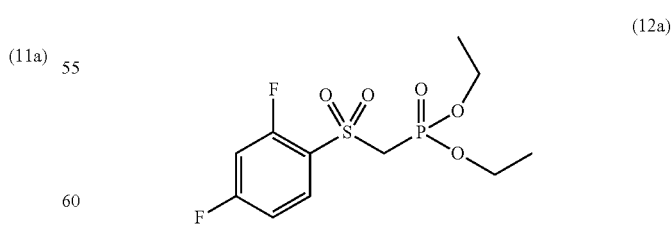

Starting from (2,4-difluorophenylsulfanylmethyl)phosphonic acid diethyl ester (11a) and potassium peroxymonosulfate, compound (12a) was obtained in 70% yield using the method described in General Procedure H. $^1$H NMR (300 MHz, CDCl$_3$), δ 7.97-7.89 (m, Ar—H, 1H), 7.04-6.89

(m, Ar—H, 2H), 4.13-4.03 (m, —OCH$_2$—, 4H), 3.85 (d, P—CH$_2$—, J=16.2 Hz, 2H), 0.81-0.76 (m, —CH$_3$, 6H).

General Procedure J. Synthesis of {5-[2-(Arylsulfonyl)vinyl]-2-(methylsulfanyl)pyrimidin-4-yl}alkylamines (13)

Compounds (13a)-(13e) were prepared by the procedure described below and illustrated in Scheme 21.

Scheme 21

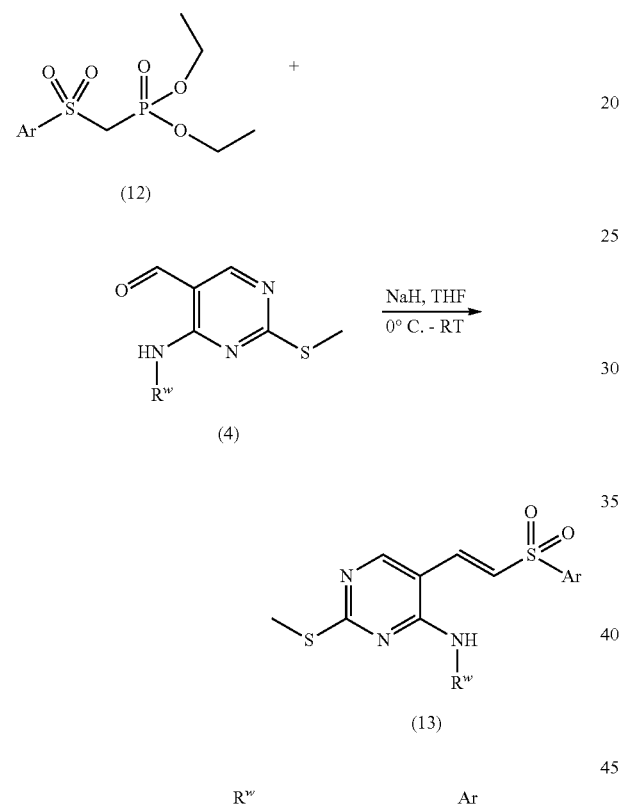

| | R$^w$ | Ar |
|---|---|---|
| (13a) | methyl | 2,4-difluorophenyl |
| (13b) | cyclopentyl | 2,4-difluorophenyl |
| (13c) | cyclopentyl | 4-methoxyphenyl |
| (13d) | 1-methyl-1H-pyraozl-3-yl | 4-methoxyphenyl |
| (13e) | 1-methyl-1H-pyrazol-3-yl | 2,4-difluorophenyl |

To a solution of phosphonate (12) (1.5 equiv.) in THF, NaH (1.5 equiv.) was added at 0° C. After stirring for 30 min., this solution was added to a solution of aldehyde (4) (1 equiv.) dissolved in THF. Then, the ice bath was removed and the solution was stirred at room temperature until completion of the reaction. Saturated NH$_4$Cl solution and ethyl acetate were added. The aqueous phase was extracted with ethyl acetate. The organic phase was dried over Na$_2$SO$_4$, filtered and evaporated. The crude product was purified by chromatography with 30% ethyl acetate in hexane to afford pure product (13).

Example 50. Synthesis of 5-{2-[(2,4-Difluorophenyl)sulfonyl]vinyl}-N-methyl-2-(methylsulfanyl)pyrimidin-4-amine (13a)

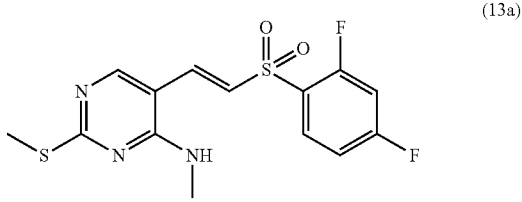 [SMILES: CNc1nc(SC)ncc1/C=C/S(=O)(=O)c1ccc(F)cc1F]

Starting from (2,4-difluorobenzenesulfonylmethyl)phosphonic acid diethyl ester (12a) and 4-N-methylamino-2-(methylsulfanyl)pyrimidinecarboxaldehyde (4b), compound (13a) was obtained in 70% yield using the method described in General Procedure J. $^1$H NMR (300 MHz, CDCl$_3$), δ 8.14 (s, Ar—H, 1H), 8.06-7.99 (m, Ar—H, 1H), 7.63 (d, =C—H, J=15.3 Hz), 7.11-7.05 (m, Ar—H, 1H), 7.01-6.94 (m, Ar—H, 1H), 6.84 (d, =C—H, J=15.0 Hz, 1H), 3.10 (d, N—CH$_3$, J=4.8 Hz, 3H), 2.56 (s, S—CH$_3$, 3H).

Example 51. Synthesis of N-Cyclopentyl-5-{2-[(2,4-difluorophenyl)sulfonyl]vinyl}-2-(methylsulfanyl)pyrimidin-4-amine (13b)

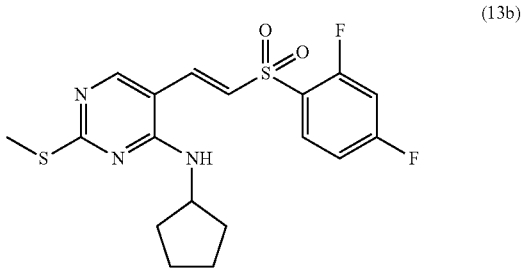 [SMILES: CSc1ncc(/C=C/S(=O)(=O)c2ccc(F)cc2F)c(NC2CCCC2)n1]

Starting from (2,4-difluorobenzenesulfonylmethyl)phosphonic acid diethyl ester (12a) and 4-cyclopentylamino-2-(methylsulfanyl)pyrimidine-5-carboxaldehyde (4h), compound (13b) was obtained in 75% yield using the method described in General Procedure J. $^1$H NMR (300 MHz, CDCl$_3$), δ 8.12 (s, Ar—H, 1H), 8.07-7.99 (m, Ar—H, 1H), 7.58 (d, =C—H, J=16.2 Hz, 1H), 7.12-7.09 (m, Ar—H, 1H), 7.06-6.95 (m, Ar—H, 1H), 6.85 (d, =C—H, J=16.5 Hz, 1H), 5.09 (d, N—H, J=6.3 Hz, 1H), 4-53-4.46 (m, C—H, 1H), 2.54 (s, S—CH$_3$, 3H), 2.20-2.10 (m, —CH$_2$—, 2H), 1.81-1.72 (m, —CH$_2$—, 4H), 1.68-1.66 (m, —CH$_2$—, 2H).

General Procedure K. Synthesis of Alkyl-{5-[2-(arylsulfonyl)-vinyl]-2-methanesulfinyl-pyrimidin-4-yl}-amine (14)

Compounds (14a)-(14e) were prepared by the procedure described below and illustrated in Scheme 22.

Scheme 22

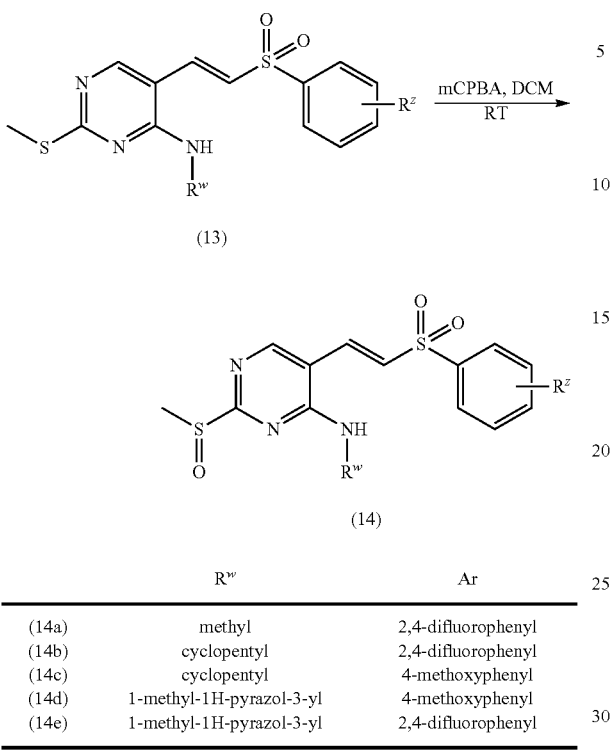

| | $R^w$ | Ar |
|---|---|---|
| (14a) | methyl | 2,4-difluorophenyl |
| (14b) | cyclopentyl | 2,4-difluorophenyl |
| (14c) | cyclopentyl | 4-methoxyphenyl |
| (14d) | 1-methyl-1H-pyrazol-3-yl | 4-methoxyphenyl |
| (14e) | 1-methyl-1H-pyrazol-3-yl | 2,4-difluorophenyl |

A solution of compound (13) (1 equiv.), and mCPBA (1.25 equiv.) in DCM was stirred at room temperature for about 12 h. After completion of the reaction, the reaction mixture was washed with saturated NaHCO$_3$, organic layer was dried over Na$_2$SO$_4$ and concentrated under reduced pressure to obtain the product (14) and was used for next reaction without further purification.

Example 52. Synthesis of 5-{2-[(2,4-Difluorophenyl)sulfonyl]vinyl}-N-methyl-2-(methylsulfinyl)pyrimidin-4-amine (14a)

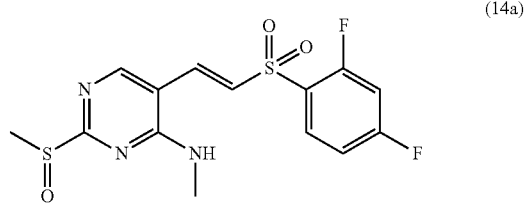 [SMILES: CNc1nc(S(C)=O)ncc1/C=C/S(=O)(=O)c1ccc(F)cc1F]

Example 53. Synthesis of N-Cyclopentyl-5-{2-[(2,4-difluorophenyl)sulfonyl]vinyl}-2-(methylsulfinyl)pyrimidin-4-amine (14b)

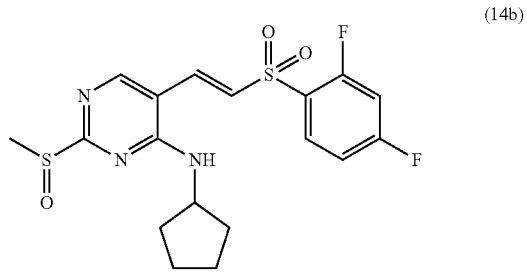 [SMILES: CS(=O)c1ncc(/C=C/S(=O)(=O)c2ccc(F)cc2F)c(NC2CCCC2)n1]

General Procedure L. Synthesis of 2-Substituted 5-(arylsulfonylvinyl)-N$^4$-alkyl-N$^2$-aryl-pyrimidine-2,4-diamine (15)

Compounds (15a)-(15u) were prepared by the procedure described below and illustrated in Scheme 23.

Scheme 23

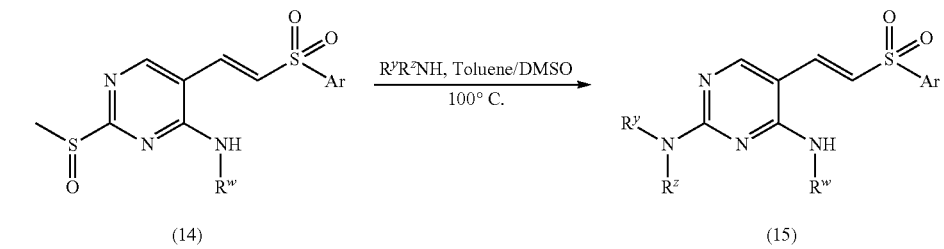

| | $R^w$ | $R^y$ | $R^z$ | Ar |
|---|---|---|---|---|
| (15a) | methyl | 1H-indol-5-yl | H | 2,4-difluorophenyl |
| (15b) | cyclopentyl | 4-(4-methylpiperazin-1-yl)phenyl | H | 2,4-difluorophenyl |
| (15c) | methyl | 1H-indol-6-yl | H | 2,4-difluorophenyl |
| (15d) | methyl | 4-(4-methylpiperazin-1-yl)phenyl | H | 2,4-difluorophenyl |
| (15e) | methyl | 4-(morpholin-4-yl)phenyl | H | 2,4-difluorophenyl |
| (15f) | methyl | 4-methoxyphenyl | H | 2,4-difluorophenyl |
| (15g) | methyl | 3,4,5-trimethoxyphenyl | H | 2,4-difluorophenyl |
| (15h) | methyl | 1H-Benzo[d]imidazol-2-yl | H | 2,4-difluorophenyl |
| (15i) | methyl | 1H-indazol-5-yl | H | 2,4-difluorophenyl |
| (15j) | cyclopentyl | 4-(4-methylpiperazin-1-yl)phenyl | H | 4-methoxyphenyl |
| (15k) | cyclopentyl | 1H-indol-5-yl | H | 4-methoxyphenyl |
| (15l) | cyclopentyl | 5-(4-methylpiperazin-1-yl)pyridin-2-yl | H | 4-methoxyphenyl |
| (15m) | cyclopentyl | 4-methoxyphenyl | H | 4-methoxyphenyl |
| (15n) | methyl | 1H-benzo[d]imidazol-5-yl | H | 2,4-difluorophenyl |

Scheme 23

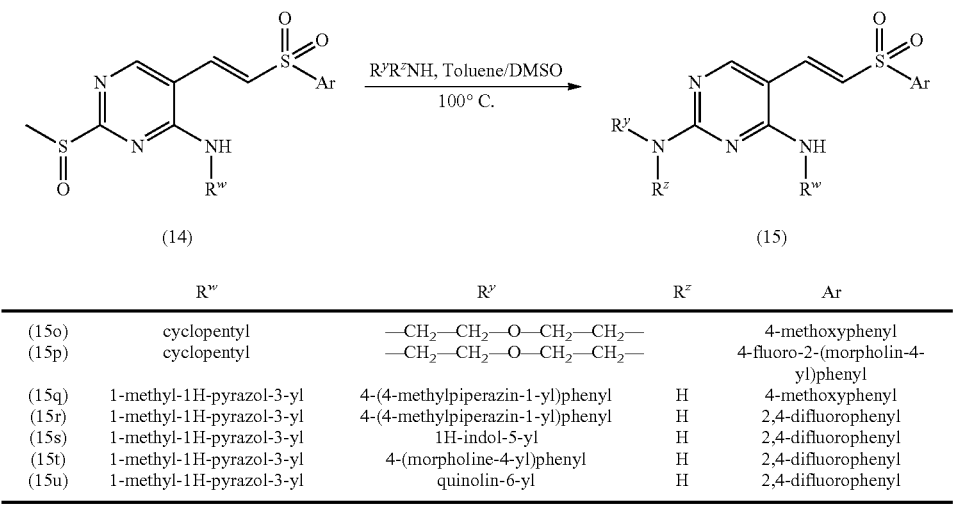

| | R^w | R^y | R^z | Ar |
|---|---|---|---|---|
| (15o) | cyclopentyl | —CH$_2$—CH$_2$—O—CH$_2$—CH$_2$— | | 4-methoxyphenyl |
| (15p) | cyclopentyl | —CH$_2$—CH$_2$—O—CH$_2$—CH$_2$— | | 4-fluoro-2-(morpholin-4-yl)phenyl |
| (15q) | 1-methyl-1H-pyrazol-3-yl | 4-(4-methylpiperazin-1-yl)phenyl | H | 4-methoxyphenyl |
| (15r) | 1-methyl-1H-pyrazol-3-yl | 4-(4-methylpiperazin-1-yl)phenyl | H | 2,4-difluorophenyl |
| (15s) | 1-methyl-1H-pyrazol-3-yl | 1H-indol-5-yl | H | 2,4-difluorophenyl |
| (15t) | 1-methyl-1H-pyrazol-3-yl | 4-(morpholine-4-yl)phenyl | H | 2,4-difluorophenyl |
| (15u) | 1-methyl-1H-pyrazol-3-yl | quinolin-6-yl | H | 2,4-difluorophenyl |

A mixture containing the compound (14) (1 equiv.) and an amine (1.2 equiv.) in toluene/DMSO was stirred at 100 OC overnight. The reaction mixture was allowed to cool and solids were collected by filtration. The product was purified by flash column chromatography using 2-4% methanol in chloroform as eluents to give purified compound (15).

Example 54. 5-{2-[2,4-(Difluorophenyl)sulfonyl]vinyl}-N$^2$-(1H-indol-5-yl)-N$^4$-methylpyrimidine-2,4-diamine (15a)

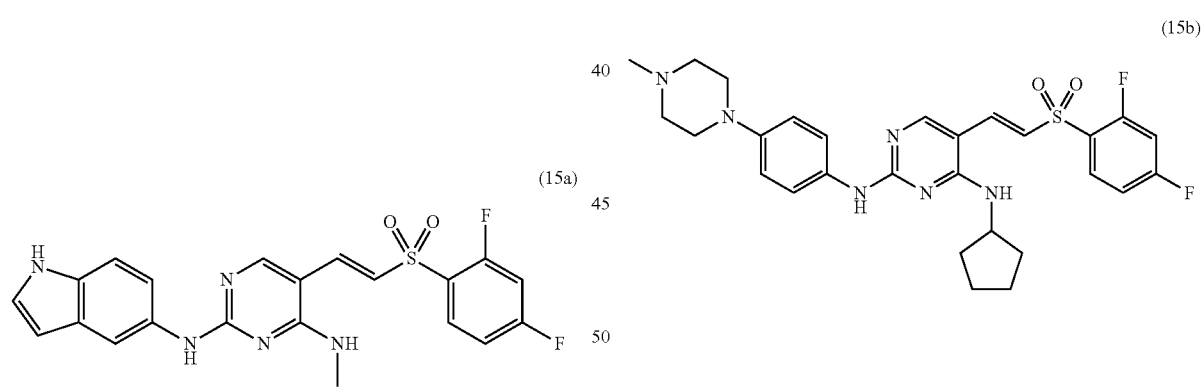

Starting from compound (14a) and 5-aminoindole, compound (15a) was obtained in 55% yield using the method described in General Procedure L. $^1$H NMR (300 MHz, CDCl$_3$), δ 10.91 (s, NH, 1H), 9.46 (s, NH, 1H), 8.42 (s, Ar—H, 1H), 8.04-7.93 (m, NH & Ar—H, 2H), 7.72 (d, =CH, J=15.0 Hz, 1H), 7.62-7.54 (m, Ar—H, 2H), 7.41-7.26 (m, Ar—H, 4H), 7.15 (d, =CH, J=15.3 Hz, 1H), 6.33 (s, Ar—H, 1H), 2.93 (d, N—CH$_3$, J=4.2 Hz, 3H).

Example 55. Synthesis of N$^4$-Cyclopentyl-5-{2-[(2,4-difluorophenyl)sulfonyl]vinyl}-N$^2$-[4-(4-methylpiperazin-1-yl)phenyl]pyrimidine-2,4-diamine (15b)

Starting from compound (14b) and 4-(4-methyl-piperazin-1-yl)-phenylamine, compound (16b) was obtained in 60% yield using the method described in General Procedure L. $^1$H NMR (300 MHz, CDCl$_3$), δ 8.12 (s, Ar—H, 1H), 8.05-7.97 (m, Ar—H, 1H), 7.58-7.48 (m, =CH & Ar—H, 3H), 7.08-6.90 (m, Ar—H, 4H), 6.62 (d, =—H, J=15.9 Hz, 1H), 5.08 (d, N—H, J=6.3 Hz, 1H), 4-46-4.44 (m, C—H, 1H), 3.21-3.17 (m, —CH$_2$, 4H), 2.61-2.58 (m, —CH$_2$—, 4H), 2.36 (s, N—CH$_3$, 3H), 2.18-2.05 (m, —CH$_2$—, 2H), 1.77-1.69 (m, —CH$_2$—, 4H), 1.53-1.51 (m, —CH$_2$—, 2H).

Example 56. Synthesis of 5-{2-[2,4-(Difluorophenyl)sulfonyl]vinyl}-N²-(1H-indol-6-yl)-N⁴-methyl-pyrimidine-2,4-diamine (15c)

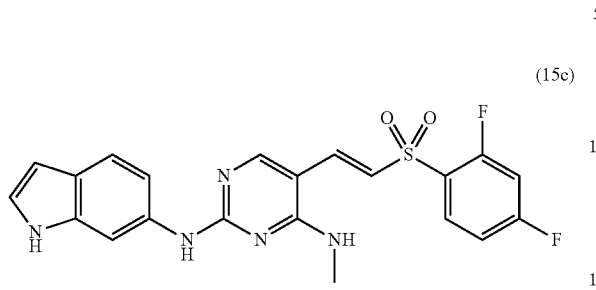

(15c)

Starting from {5-[2-(2,4-difluoro-benzenesulfonyl)-vinyl]-2-methanesulfinyl-pyrimidin-4-yl}-methyl-amine (14a) and 6-aminoindole, compound (15c) was obtained in 50% yield using the method described in General Procedure L. ¹H NMR (300 MHz, DMSO-$d_6$), δ 10.99 (s, NH, 1H), 9.58 (s, NH, 1H), 8.44 (s, Ar—H, 1H), 8.15 (bs, NH, 1H), 8.02-7.94 (m, Ar—H, 1H), 7.73 (d, =CH, J=15.0 Hz, 1H), 7.62-7.55 (m, Ar—H, 2H), 7.40-7.33 (m, Ar—H, 2H), 7.26-7.16 (m, 2Ar—H & =CH, 3H), 6.32 (s, Ar—H, 1H), 2.98 (d, N—CH₃, J=4.2 Hz, 3H).

Example 57. N-methyl-2-(methylsulfanyl)-5-(2-nitrovinyl)pyrimidin-4-amine (16a)

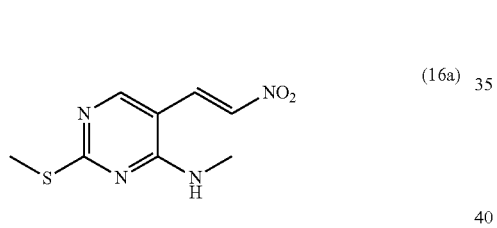

(16a)

The title compound is prepared starting from compound (4b) via reaction with nitromethane and ammonium acetate in acetic acid at 70° C. The solvent is evaporated under reduced pressure, the residue is partitioned between DCM and water, and the organic layer is washed with aq. NaHCO₃ and brine, then dried (MgSO₄), filtered and evaporated.

Example 58. N-methyl-2-(methylsulfinyl)-5-(2-nitrovinyl)pyrimidin-4-amine (16b)

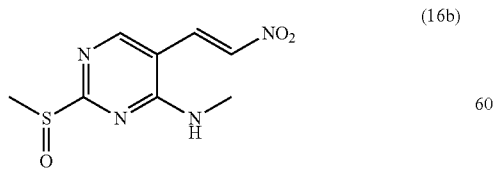

(16b)

The title compound is prepared starting from compound (16a) by a method analogous to that described in General Procedure F.

Example 59. N⁴-methyl-N²-[4-(4-methylpiperazin-1-yl)phenyl]-5-(2-nitrovinyl)pyrimidine-2,4-diamine (16c)

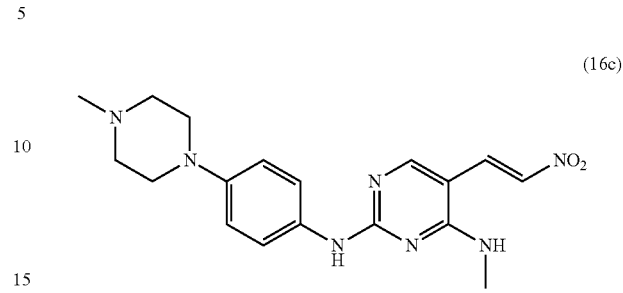

(16c)

The title compound is prepared starting from compound (16b) and 4-(4-methylpiperazin-1-yl)aniline by a method analogous to that described in General Procedure G.

Example 60. N-Cyclopentyl-2-(methylsulfanyl)-5-(2-nitrovinyl)pyrimidin-4-amine (16d)

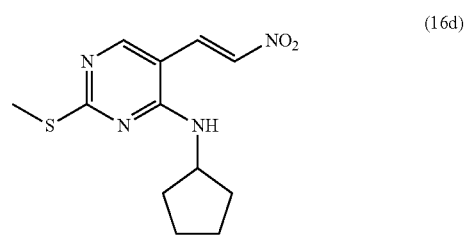 [SMILES: CSc1ncc(/C=C/[N+](=O)[O-])c(NC2CCCC2)n1]

(16d)

The title compound is prepared starting from compound (4h) by a method analogous to that described for the preparation of compound (16a).

Example 61. N-Cyclopentyl-2-(methylsulfinyl)-5-(2-nitrovinyl)pyrimidin-4-amine (16e)

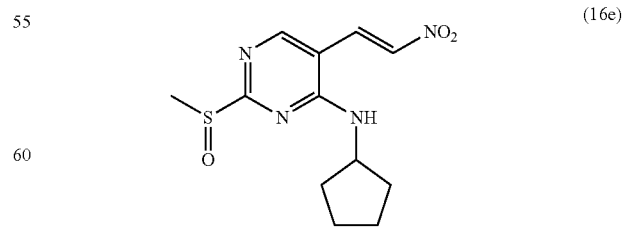

(16e)

The title compound is prepared starting from compound (16d) by a method analogous to that described in General Procedure F.

Example 62. N⁴-Cyclopentyl-N²-[4-(4-methylpiperazin-1-yl)phenyl]-5-(2-nitrovinyl)pyrimidine-2,4-diamine (16f)

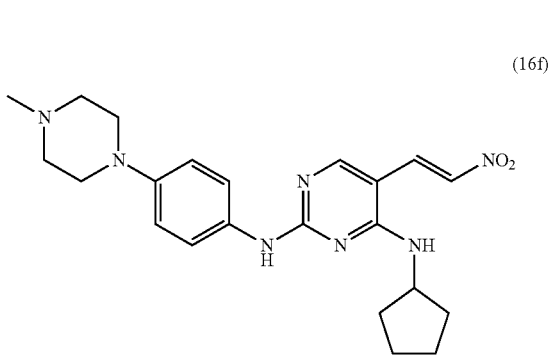 [SMILES: CN1CCN(c2ccc(Nc3ncc(/C=C/[N+](=O)[O-])c(NC4CCCC4)n3)cc2)CC1]

(16f)

The title compound is prepared starting from compound (16e) and 4-(4-methylpiperazin-1-yl)aniline by a method analogous to that described in General Procedure G.

Example 63. 3-(4-(Methylamino)-2-{[4-(4-methylpiperazin-1-yl)phenyl]amino}pyrimidin-5-yl)acrylic acid (17a)

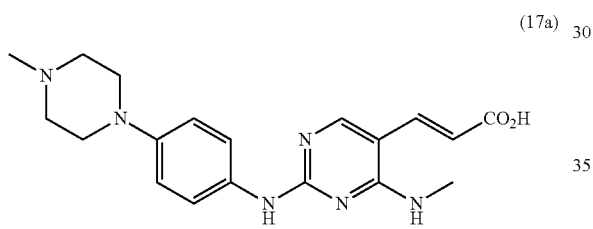

(17a)

Compound (8b) is heated in hydrochloric acid (1:1 conc. HCl/H₂O) under reflux. When the starting material is consumed (as determined by TLC), the solvent is removed under reduced pressure. The product is purified by reverse phase HPLC using a gradient of acetonitrile and trifluoroacetic acid.

Example 64. 3-(4-(Cyclopentylamino)-2-{[4-(4-methylpiperazin-1-yl)phenyl]amino}pyrimidin-5-yl)acrylic acid (17b)

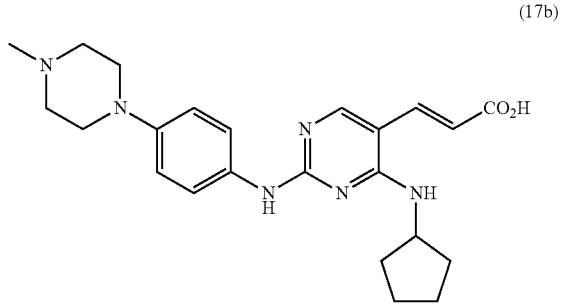 [SMILES: CN1CCN(c2ccc(Nc3ncc(/C=C/C(=O)O)c(NC4CCCC4)n3)cc2)CC1]

(17b)

The title compound is prepared starting from compound (8h) by a method analogous to that described for Example 63.

Example 65. 4-[4-(Methylamino)-2-(methylsulfanyl)pyrimidin-5-yl]but-3-en-2-one (18a)

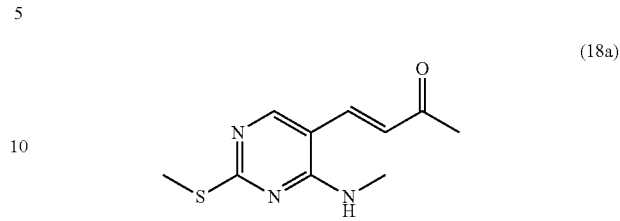

(18a)

The title compound is prepared starting from compound (4b) via reaction with diethyl(2-oxopropyl)phosphonate and sodium hydride in THF. When reaction is complete, butanol is added to quench any unreacted sodium hydride, followed by the addition of water. The solvent is evaporated under reduced pressure, the residue is partitioned between DCM and water, and the organic layer is washed with aq. NaHCO₃ and brine, then dried (MgSO₄), filtered and evaporated.

Example 66. 4-[4-(Methylamino)-2-(methylsulfinyl)pyrimidin-5-yl]but-3-en-2-one (18b)

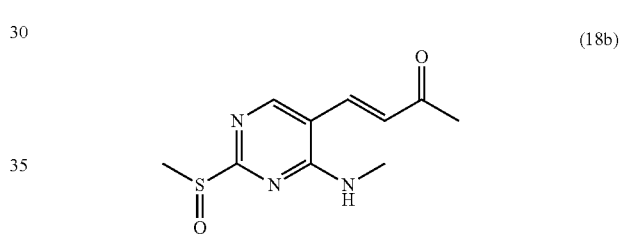

(18b)

The title compound is prepared starting from compound (18a) by a method analogous to that described in General Procedure F.

Example 67. 4-(4-(Methylamino)-2-{[4-(4-methylpiperazin-1-yl)phenyl]amino}pyrimidin-5-yl)but-3-en-2-one (18c)

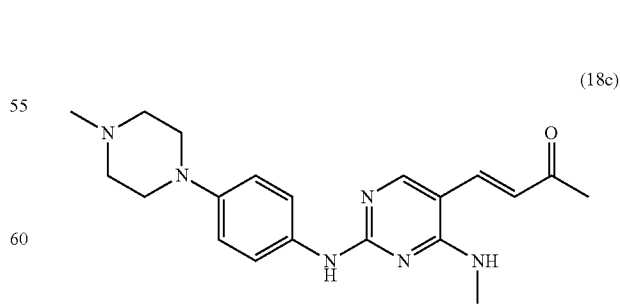

(18c)

The title compound is prepared starting from compound (18b) and 4-(4-methylpiperazin-1-yl)aniline by a method analogous to that described in General Procedure G.

Example 68. 4-[4-(Cyclopentylamino)-2-(methylsulfanyl)pyrimidin-5-yl]but-3-en-2-one (18d)

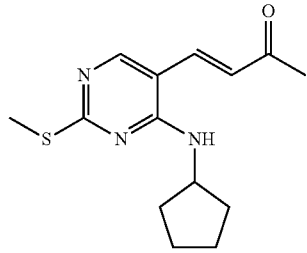
(18d)

The title compound is prepared starting from compound (4h) by a method analogous to that described for Example 65.

Example 69. 4-[4-(Cyclopentylamino)-2-(methylsulfinyl)pyrimidin-5-yl]but-3-en-2-one

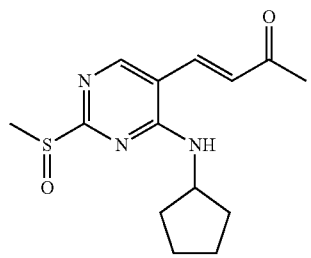
(18e)

The title compound is prepared starting from compound (18d) by a method analogous to that described in General Procedure F.

Example 70. 4-(4-(Cyclopentylamino)-2-{[4-(4-methylpiperazin-1-yl)phenyl]amino}pyrimidin-5-yl)but-3-en-2-one (18f)

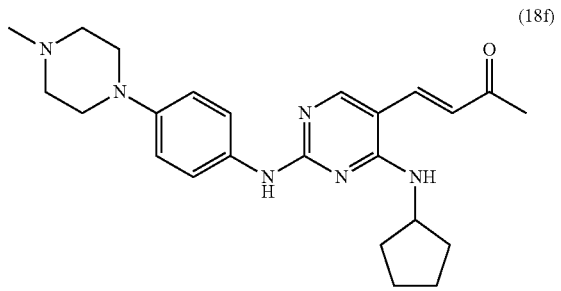 [SMILES: CC(=O)/C=C/c1cnc(Nc2ccc(N3CCN(C)CC3)cc2)nc1NC1CCCC1]
(18f)

The title compound is prepared starting from compound (18e) and 4-(4-methylpiperazin-1-yl)aniline by a method analogous to that described in General Procedure G.

Example 71. (E)-3-[4-(Cyclopentylamino)-2-morpholinopyrimidin-5-yl]acrylonitrile (8z)

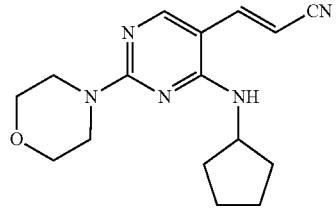
(8z)

The title compound was prepared starting from compound (7h) and morpholine by the method of General Procedure G.

Preparation 33. 4-[(1-Methyl-1H-pyrazol-3-yl)amino]-2-(methylsulfanyl)pyrimidine-5-carboxylic acid ethyl ester (2j)

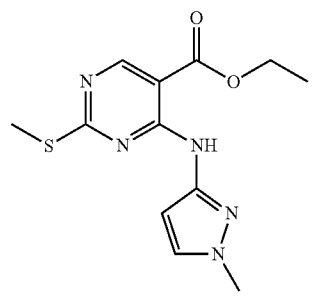
(2j)

The title compound was prepared starting from 4-chloro-2-(methylsulfanyl)pyrimidine-5-carboxylic acid ethyl ester (1) and 1-methyl-1H-pyrazol-3-amine by the method of General Procedure A.

Preparation 34. {4-[(1-Methyl-1H-pyrazol-3-yl)amino]-2-(methylthio)pyrimidin-5-yl}methanol (3j)

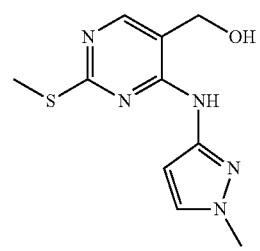
(3j)

The title compound was prepared starting from compound (2j) by the method of General Procedure B.

Preparation 35. 4-[(1-Methyl-1H-pyrazol-3-yl)amino]-2-(methylsulfanyl)pyrimidine-5-carboxaldehyde (4m)

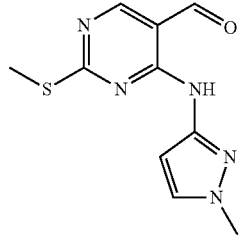
(4m)

The title compound was prepared starting from compound (3j) by the method of General Procedure C.

Example 72. (E)-3-{4-[(1-Methyl-1H-pyrazol-3-yl)amino]-2-(methylsulfanyl)pyrimidin-5-yl}acrylonitrile (6m)

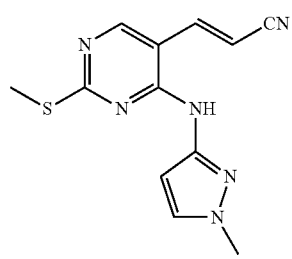
(6m)

The title compound was prepared starting from compound (4m) by the method of General Procedure D.

Example 73. (E)-3-{4-[(1-Methyl-1H-pyrazol-3-yl)amino]-2-(methylsulfinyl)pyrimidin-5-yl}acrylonitrile (7m)

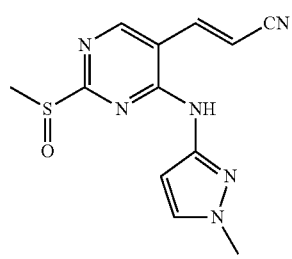
(7m)

The title compound was prepared starting from compound (4m) by the method of General Procedure E.

Example 74. (E)-3-(4-[(1-Methyl-1H-pyrazol-3-yl)amino]-2-{[4-(4-methylpiperazin-1-yl)phenyl]amino}pyrimidin-5-yl)acrylonitrile (8aa)

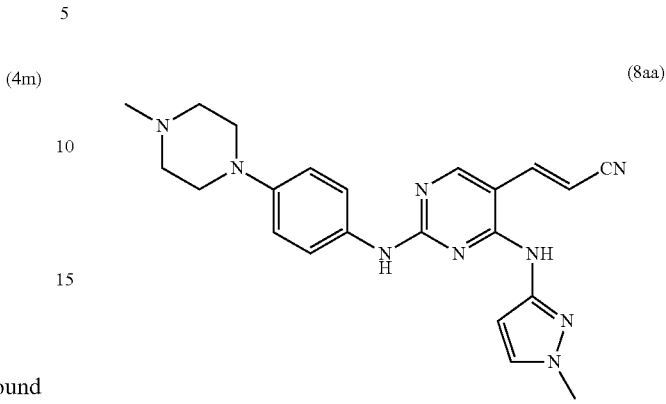
(8aa)

The title compound was prepared starting from compound (7m) and 4-(4-methylpiperazin-1-yl)aniline by the method of General Procedure G. $^1$H NMR (300 MHz, DMSO-$d_6$), δ 2.22 (s, NCH$_3$, 3H), 2.46-2.43 (m, CH$_2$, 4H), 3.08-3.05 (m, CH$_2$, 4H), 3.80 (s, NCH$_3$, 3H), 6.28 (bs, NH, 1H), 6.84 (bs, Ar—H, 2H), 7.49-7.46 (d, Ar—H, J=9.0 Hz, 2H), 7.65 (bs, Ar—H, 1H), 8.41 (s, Ar—H, 1H), 9.51 (bs, Ar—H, 1H), 9.75 (bs, NH, 1H).

Example 75. (E)-3-[4-(Cyclopentylamino)-2-{[2-methoxy-4-(4-methylpiperazin-1-yl)phenyl]amino}pyrimidin-5-yl]acrylonitrile (8bb)

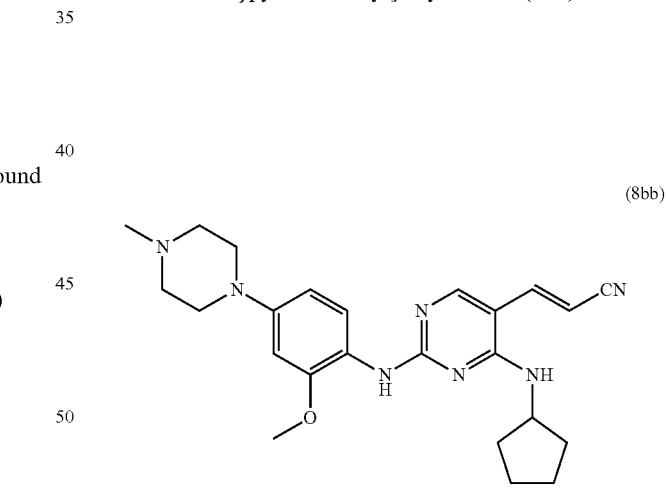
(8bb)

The title compound was prepared starting from compound (7h) and 2-methoxy-4-(4-methylpiperazin-1-yl)aniline by the method of General Procedure G. $^1$H NMR (300 MHz, DMSO-$d_6$), δ 1.82-1.70 (m, CH$_2$, 6H), 2.19-2.06 (m, CH$_2$, 2H), 2.39 (s, NCH$_3$, 3H), 2.69-2.66 (m, CH$_2$, 4H), 3.25-3.21 (m, CH$_2$, 4H), 3.89 (s, OCH$_3$, 3H), 4.51-4.45 (m, CH, 1H), 4.95 (bs, NH, 1H), 5.54 (d, =CH, J=16.2 Hz, 1H), 6.56-6.53 (m, Ar—H, & =CH, 2H), 7.24-7.19 (m, Ar—H, 1H), 7.55 (bs, Ar—H, 1H), 8.08 (s, Ar—H, 1H), 8.35 (bs, NH, 1H).

Example 76. (E)-5-{2-[(2,4-Difluorophenyl)sulfonyl]vinyl}-$N^4$-methyl-$N^2$-[4-(4-methylpiperazin-1-yl)phenyl]pyrimidine-2,4-diamine (15d)

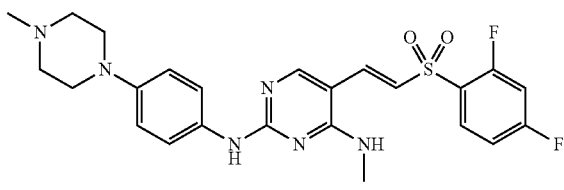

(15d)

The title compound was prepared starting from compound (14a) and 4-(4-methylpiperazin-1-yl)aniline by the method of General Procedure L. $^1$H NMR (300 MHz, DMSO-$d_6$), δ 2.21 (s, NCH$_3$, 3H), 2.45-2.42 (m, CH$_2$, 4H), 2.89 (d, NHCH3, J=4.5 Hz, 3H), 3.07-3.04 (m, CH$_2$, 4H), 6.88-6.85 (m, Ar—H, 2H), 7.15 (d, =CH, J=15.3 Hz, 1H), 7.39-7.32 (m, Ar—H, 1H), 7.64-7.54 (m, Ar—H & NH, 4H), 7.71 (d, =CH, J=15 Hz, 1H), 8.01-7.93 (m, Ar—H, 1H), 8.41 (s, Ar—H, 1H), 9.44 (bs, NH, 1H).

Example 77. (E)-5-{2-[(2,4-Difluorophenyl)sulfonyl]vinyl}-$N^4$-methyl-$N^2$-(4-morpholinophenyl)pyrimidine-2,4-diamine (15e)

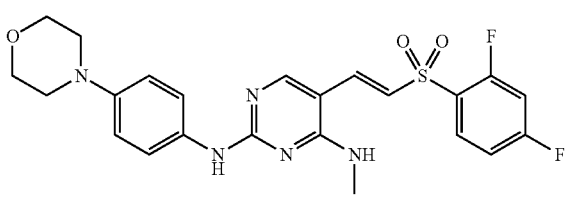

(15e)

The title compound was prepared starting from compound (14a) and 4-morpholinoaniline by the method of General Procedure L. $^1$H NMR (300 MHz, DMSO-$d_6$), δ 2.90 (bs, NHCH$_3$, 3H), 3.03 (bs, CH$_2$, 4H), 3.72 (bs, CH$_2$, 4H), 6.89-6.86 (m, Ar—H, 2H), 7.16 (d, =CH, J=15.0 Hz, 1H), 7.38-7.33 (m, Ar—H, 1H), 7.73-7.55 (m, Ar—H, =CH & NH, 5H), 8.01-7.93 (m, Ar—H, 1H), 8.41 (s, Ar—H, 1H), 9.46 (bs, NH, 1H).

Example 78. (E)-5-{2-[(2,4-Difluorophenyl)sulfonyl]vinyl}-$N^2$-(4-methoxyphenyl)-$N^4$-methylpyrimidine-2,4-diamine (15f)

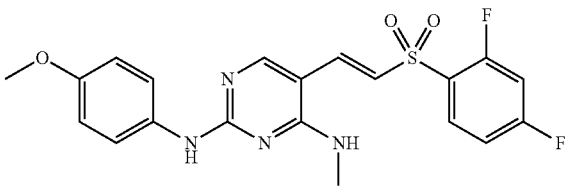

(15f)

The title compound was prepared starting from compound (14a) and 4-methoxyaniline by the method of General Procedure L. $^1$H NMR (300 MHz, DMSO-$d_6$), δ 2.89 (bs, NHCH$_3$, 3H), 3.71 (s, OCH$_3$, 3H), 6.90-6.88 (m, Ar—H, 2H), 7.16 (d, =CH, J=15.3 Hz, 1H), 7.39-7.33 (m, Ar—H, 1H), 7.61-7.58 (m, Ar—H 2H), 7.74-7.68 (m, Ar—H & =CH, 3H), 8.01-7.93 (m, Ar—H, 1H), 8.42 (s, Ar—H, 1H), 9.50 (bs, NH, 1H).

Example 79. (E)-5-{2-[(2,4-Difluorophenyl)sulfonyl]vinyl}-$N^4$-methyl-$N^2$-(3,4,5-trimethoxyphenyl)pyrimidine-2,4-diamine (15g)

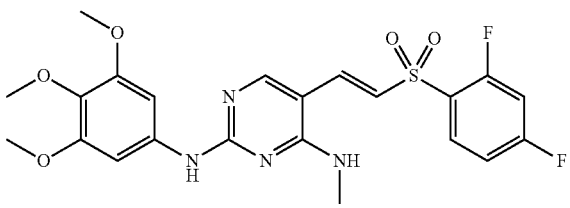

(15g)

The title compound was prepared starting from compound (14a) and 3,4,5-trimethoxyaniline by the method of General Procedure L. $^1$H NMR (300 MHz, DMSO-$d_6$), δ 2.88 (bs, NHCH$_3$, 3H), 3.82 (s, OCH$_3$, 3H), 3.86 (s, OCH$_3$, 6H), 6.72 (d, =CH, J=15.3 Hz, 1H), 6.95-6.91 (m, Ar—H, 1H), 6.98 (s, Ar—H, 2H), 7.08-7.01 (m, Ar—H 1H), 7.62 (d, =CH, J=15.0 Hz, 1H), 7.99-7.96 (m, Ar—H, 1H), 8.15 (s, Ar—H, 1H), 8.35 (bs, NH, 1H).

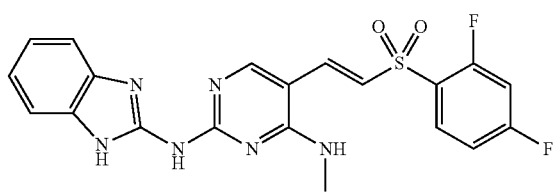

(15h)

Example 80. (E)-$N^2$-(1H-Benzo[d]imidazol-2-yl)-5-{2-[(2,4-difluorophenyl)sulfonyl]vinyl}-$N^4$-methyl-pyrimidine-2,4-diamine (15h)

The title compound was prepared starting from compound (14a) and 1H-benzo[d]imidazol-2-amine by the method of General Procedure L. $^1$H NMR (300 MHz, DMSO-$d_6$), δ 3.03 (d, NHCH$_3$, J=4.2 Hz, 3H), 7.02-6.95 (m, Ar—H, 1H), 7.12-7.09 (m, Ar—H, 1H), 7.19-7.17 (m, Ar—H, 1H), 7.43-7.37 (m, Ar—H 1H), 7.67-7.53 (m, Ar—H & =CH, 2H), 7.88-7.83 (m, =CH & NH, 3H), 8.07-7.98 (m, Ar—H, 1H), 8.34-8.30 (m, Ar—H & NH, 2H), 8.69 (s, Ar—H, 1H).

Example 81. (E)-5-{2-[(2,4-Difluorophenyl)sulfonyl]vinyl}-$N^2$-(1H-indazol-5-yl)-N-methylpyrimidine-2,4-diamine (15i)

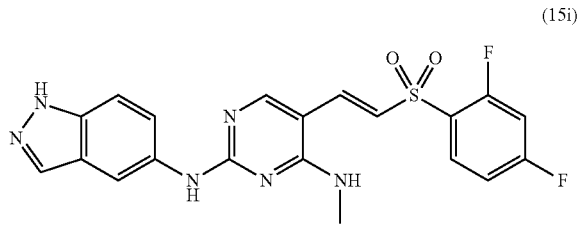 [SMILES: CNc1nc(Nc2ccc3[nH]ncc3c2)ncc1/C=C/S(=O)(=O)c1ccc(F)cc1F]

(15i)

The title compound was prepared starting from compound (14a) and 1H-indazol-5-amine by the method of General Procedure L. $^1$H NMR (300 MHz, DMSO-$d_6$), δ 2.94 (bs, NHCH$_3$, 3H), 7.17 (d, =CH, J=15.0 Hz, 1H), 7.46-7.37 (m, Ar—H, 2H), 7.64-7.55 (m, Ar—H 3H), 7.74 (d, =CH, J=15.0 HZ, 1H), 8.00-7.96 (m, Ar—H, 2H), 8.29 (bs, NH, 1H), 8.45 (s, Ar—H, 1H), 9.65 (bs, NH, 1H), 12.91 (s, NH, 1H).

Preparation 36. (4-Methoxysulfanylmethyl)-phosphonic acid diethyl ester (11b)

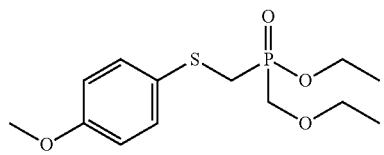

(11b)

The title compound was prepared starting from 4-methoxybenzenethiol (10b) and iodomethyldiethylphosphonate (10) by the method of General Procedure H.

Preparation 37. (4-Methoxysulfonylmethyl)-phosphonic acid diethyl ester (12b)

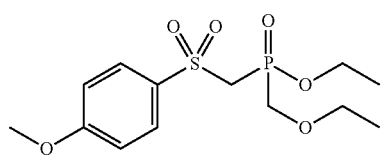

(12b)

The title compound was prepared starting from compound (11b) by the method of General Procedure I.

Example 82. (E)-N-Cyclopentyl-5-(2-((4-methoxyphenyl)sulfonyl)vinyl)-2-(methylsulfanyl)pyrimidin-4-amine (13c)

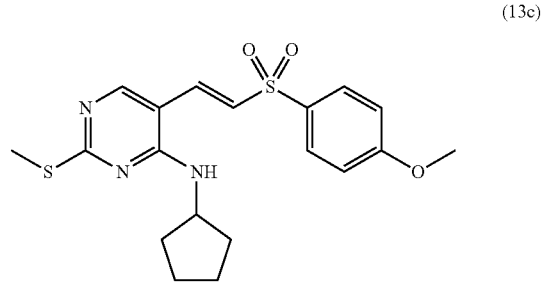

(13c)

The title compound was prepared starting from compound (12b) and aldehyde (4h) by the method of General Procedure J.

Example 83. (E)-N-Cyclopentyl-5-{2-[(4-methoxyphenyl)sulfonyl]vinyl}-2-(methylsulfinyl)pyrimidin-4-amine (14c)

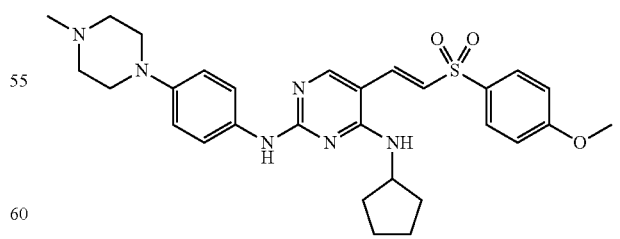

(14c)

The title compound was prepared starting from compound (13c) and 4-(4-methylpiperazin-1-yl)aniline by the method of General Procedure K.

Example 84. (E)-$N^4$-Cyclopentyl-5-{2-[(4-methoxyphenyl)sulfonyl]vinyl}-$N^2$-[4-(4-methylpiperazin-1-yl)phenyl]pyrimidine-2,4-diamine (15j)

(15j)

The title compound was prepared starting from compound (14c) and 4-(4-methylpiperazin-1-yl)aniline by the method of General Procedure L. $^1$H NMR (300 MHz, DMSO-$d_6$), δ 1.83-1.70 (m, CH$_2$, 6H), 2.37-2.07 (m, CH$_2$, 2H), 2.37 (s, NCH$_3$, 3H), 2.62-2.37 (m, CH$_2$, 4H), 3.21-3.17 (m, CH$_2$, 4H), (3.89 (s, OCH₃, 3H), 4.46-4.39 (m, C—H, 1H), 5.02 (bs, NH, 1H), 6.50 (d, =CH, J=15.3 Hz, 1H), 6.94-6.91 (m, Ar—H, 2H), 7.04-7.01 (m, Ar—H, 2H), 7.08 (bs, NH, 1H), 7.51-7.43 (m, Ar—H & =CH, 3H), 7.88-7.85 (m, Ar—H, 2H), 8.07 (s, Ar—H, 1H).

Example 85. (E)-N⁴-Cyclopentyl-N²-(1H-indol-5-yl)-5-{2-[(4-methoxyphenyl)sulfonyl]vinyl}pyrimidine-2,4-diamine (15k)

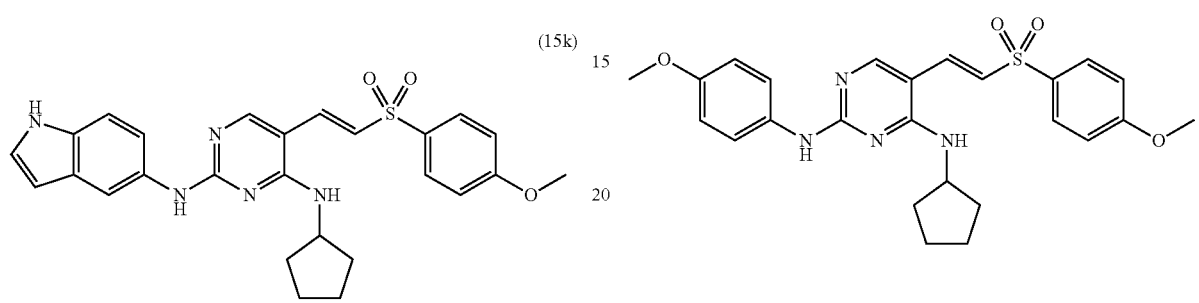

(15k)

The title compound was prepared starting from compound (14c) and 1H-indole-5-amine by the method of General Procedure L. ¹H NMR (300 MHz, DMSO-d₆), δ 1.77-1.69 (m, CH₂, 6H), 2.16-2.04 (m, CH₂, 2H), 3.85 (s, OCH₃, 3H), 4.45-4.39 (m, C—H, 1H), 5.29 (bs, Ar—H, 1H), 6.66-6.44 (m, Ar—H & =CH, 2H), 7.00-6.93 (m, Ar—H, 2H), 7.30-7.19 (m, Ar—H, 3H), 7.50 (d, =CH, J=15 Hz, 1H), 7.86-7.82 (m, Ar—H 2H), 8.08 (bs, Ar—H & NH, 2H), 8.76 (s, NH, 1H).

Example 86. (E)-5-{2-[(2,4-Difluorophenyl)sulfonyl]vinyl}-N⁴-methyl-N²-[5-(4-methylpiperazin-1-yl)pyridin-2-yl]pyrimidine-2,4-diamine (15l)

The title compound was prepared starting from compound (14a) and 5-(4-methylpiperazin-1-yl)pyridin-2-amine by the method of General Procedure L. ¹H NMR (300 MHz, DMSO-d₆), δ 2.20 (s, NCH₃, 3H), 2.45-2.39 (m, CH₂, 4H), 2.91 (d, NHCH₃, J=4.5 Hz, 3H), 3.12-3.09 (m, CH₂, 4H), 7.25 (d, =CH, J=15 Hz, 1H), 7.43-7.21 (m, Ar—H, 2H), 7.76-7.55 (m, Ar—H, NH & =CH, 3H), 8.02-7.96 (m, Ar—H 2H), 8.16 (d, Ar—H, J=9 Hz, 1H), 8.44 (s, Ar—H, 1H), 9.49 (s, NH, 1H).

Example 87. (E)-N⁴-Cyclopentyl-N²-(4-methoxyphenyl)-5-{2-[(4-methoxyphenyl)sulfonyl]vinyl}pyrimidine-2,4-diamine (15m)

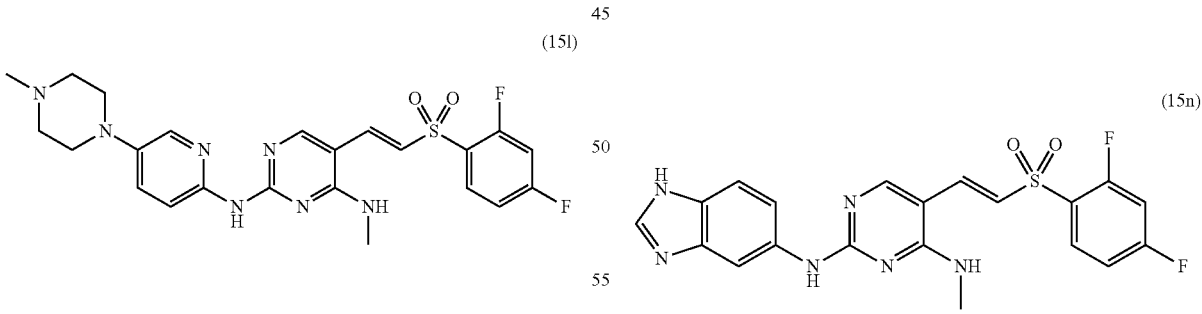

(15m)

The title compound was prepared starting from compound (14c) and 4-methoxyaniline by the method of General Procedure L. ¹H NMR (300 MHz, DMSO-d₆), δ 1.78-1.50 (m, CH₂, 6H), 2.14-2.11 (m, CH₂, 2H), 3.82 (s, OCH₃, 3H), 3.89 (s, OCH₃, 3H), 4.45-4.38 (m, C—H, 1H), 5.00 (bs, NH, 1H), 6.52 (d, =CH, J=15.3 Hz, 1H), 6.90-6.87 (m, Ar—H, 2H), 7.07-7.01 (m, Ar—H & NH, 3H), 7.52-7.49 (m, Ar—H & =CH, 3H), 7.88-7.85 (m, Ar—H, 2H), 8.07 (s, Ar—H, 1H), 9.49 (s, NH, 1H).

Example 88. (E)-N²-(1H-Benzo[d]imidazol-5-yl)-5-{2-[(2,4-difluorophenyl)sulfonyl]vinyl}-N⁴-methylpyrimidine-2,4-diamine (15n)

(15n)

The title compound was prepared starting from compound (14a) and 1H-benzo[d]imidazol-5-amine by the method of General Procedure L. ¹H NMR (300 MHz, DMSO-d₆), δ 3.03 (d, NHCH₃, J=4.2 Hz, 3H), 5.04 (bs, NH, 1H), 6.71-6.70 (m, Ar—H, 1H), 6.86 (bs, Ar—H, 1H), 7.43-7.33 (m, Ar—H, 1H), 7.67-7.53 (m, Ar—H & =CH, 2H), 7.84 (d, =CH, J=15.3 Hz, 1H), 8.06-7.98 (m, Ar—H, 1H), 8.32-8.14 (m, Ar—H & NH, 2H), 8.67 (s, Ar—H, 1H), 8.86 (s, Ar—H, 1H), 9.01 (bs, NH, 1H).

Example 89. (E)-N-Cyclopentyl-5-{2-[(4-methoxyphenyl)sulfonyl]vinyl}-2-morpholinopyrimidin-4-amine (15o)

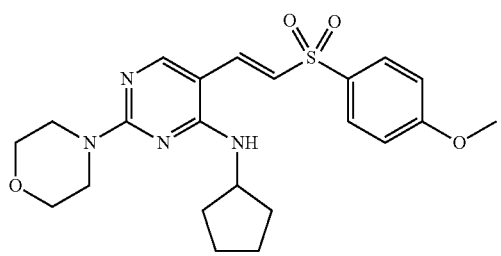

(15o)

The title compound was prepared starting from compound (14c) and morpholine by the method of General Procedure L. ¹H NMR (300 MHz, DMSO-$d_6$), δ 1.81-1.41 (m, $CH_2$, 6H), 2.15-2.04 (m, $CH_2$, 2H), 3.74-3.72 ($CH_2$, 4H), 3.86-3.81 (m, $CH_2$, 4H), 3.90 (s, $OCH_3$, 3H), 4.39-4.32 (m, C—H, 1H), 4.93 (bs, NH, 1H), 6.44 (d, =CH, J=15.0 Hz, 1H), 7.02-6.99 (m, Ar—H, 2H), 7.44 (d, =CH, J=15.3 Hz, 1H), 8.04 (s, Ar—H, 1H).

Example 90. (E)-N-Cyclopentyl-5-{2-[(4-fluoro-2-morpholinophenyl)sulfonyl]vinyl}-2-morpholinopyrimidin-4-amine (15p)

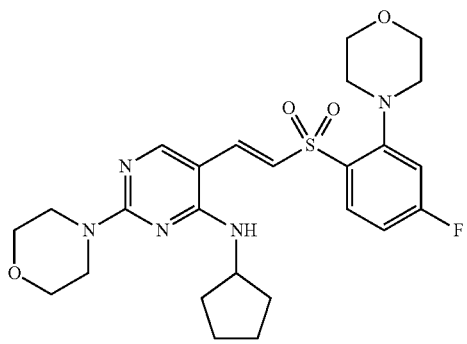

(15p)

The title compound was prepared starting from compound (14a) and morpholine by the method of General Procedure L. ¹H NMR (300 MHz, DMSO-$d_6$), δ 3.05-3.01 (m, $CH_2$ & $NHCH_3$, 7H), 3.77-3.74 (m, $CH_2$, 4H), 3.90-3.85 (m, $CH_2$, 4H), 5.05 (bs, NH, 1H), 7.07-7.02 (m, Ar—H & =CH, 3H), 7.48 (d, =CH, J=15.3 Hz, 1H), 8.05 (s, Ar—H, 1H), 8.15-8.10 (m, Ar—H, 1H).

Example 91. (E)-5-{2-[(4-Methoxyphenyl)sulfonyl]vinyl}-N-(1-methyl-1H-pyrazol-3-yl)-2-(methylsulfanyl)pyrimidin-4-amine (13d)

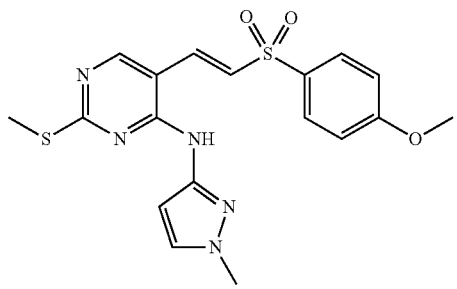

(13d)

The title compound was prepared starting from compound (12b) and aldehyde (4m) by the method of General Procedure J.

Example 92. (E)-5-{2-[(4-Methoxyphenyl)sulfonyl]vinyl}-N-(1-methyl-1H-pyrazol-3-yl)-2-(methylsulfinyl)pyrimidin-4-amine (14d)

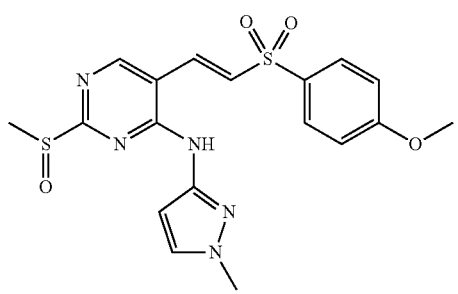

(14d)

The title compound was prepared starting from compound (13d) by the method of General Procedure K.

Example 93. (E)-5-{2-[(4-Methoxyphenyl)sulfonyl]vinyl}-$N^4$-(1-methyl-1H-pyrazol-3-yl)-$N^2$-[4-(4-methylpiperazin-1-yl)phenyl]pyrimidine-2,4-diamine (15q)

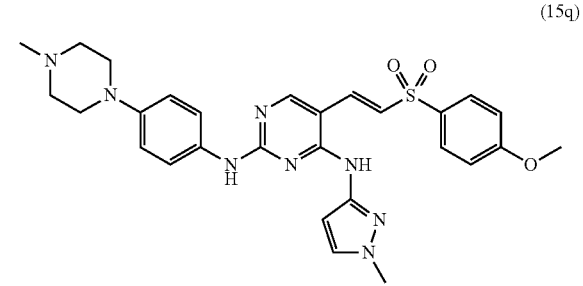

(15q)

The title compound was prepared starting from compound (14d) and 4-(4-methylpiperazin-1-yl)aniline by the method of General Procedure L. $^1$H NMR (300 MHz, DMSO-$d_6$), δ 2.22 (s, NCH$_3$, 3H), 2.47-2.46 (m, CH$_2$, 4H), 3.07-3.04 (m, CH$_2$, 4H), 3.80 (s, NHCH$_3$, 3H) 3.85 (s, OCH$_3$, 3H), 6.83-6.80 (m, Ar—H, 2H), 7.18-7.14 (m, Ar—H & =CH, 3H), 7.51-7.48 (m, Ar—H, 2H), 7.63 (bs, Ar—H, 1H), 7.96-7.87 (m, Ar—H & =CH, 3H), 8.49 (s, Ar—H, 1H), 9.38 (s, NH, 1H), 9.80 (s, NH, 1H).

Example 94. (E)-5-{2-[(2,4-Difluorophenyl)sulfonyl]vinyl}-N-(1-methyl-1H-pyrazol-3-yl)-2-(methylsulfanyl)pyrimidin-4-amine (13e)

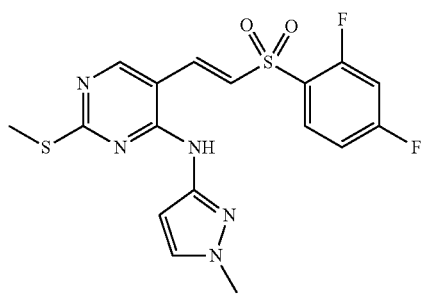

(13e)

The title compound was prepared starting from compound (12a) and aldehyde (4m) by the method of General Procedure J.

Example 95. (E)-5-{2-[(2,4-Difluorophenyl)sulfonyl]vinyl}-N-(1-methyl-1H-pyrazol-3-yl)-2-(methylsulfinyl)pyrimidin-4-amine (14e)

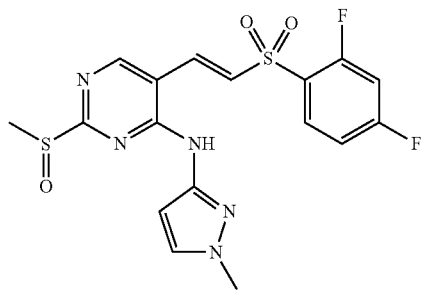

(14e)

The title compound was prepared starting from compound (13e) by the method of General Procedure K.

Example 96. (E)-5-{2-[(2,4-Difluorophenyl)sulfonyl]vinyl}-N$^4$-(1-methyl-1H-pyrazol-3-yl)-N$^2$-[4-(4-methylpiperazin-1-yl)phenyl]pyrimidine-2,4-diamine (15r)

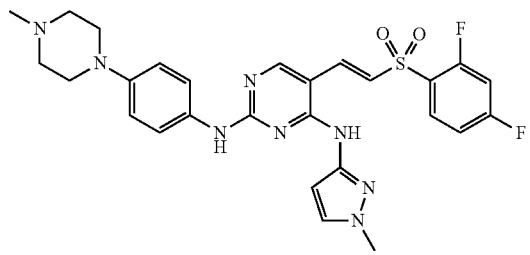

(15r)

The title compound was prepared starting from compound (14e) and 4-(4-methylpiperazin-1-yl)aniline by the method of General Procedure L. $^1$H NMR (300 MHz, DMSO-$d_6$), δ 2.52 (s, NCH$_3$, 3H), 2.81 (bs, CH$_2$, 4H), 3.33-3.31 (m, CH$_2$, 4H), 3.83 (s, NCH$_3$, 3H), 6.57 (bs, NH, 1H), 6.78 (d, =CH, J=15.0 Hz, 1H), 7.01-6.93 (m, Ar—H, 3H), 7.09-7.03 (m, Ar—H, 1H), 7.24-7.21 (m, Ar—H, 2H), 7.38 (bs, NH, 1H), 7.45-7.41 (m, Ar—H, 2H), 7.68 (d, =CH, J=15.0 Hz, 1H), 8.06-7.98 (m, Ar—H, 1H), 8.27 (s, Ar—H, 1H).

Example 97. (E)-5-{2-[(2,4-Difluorophenyl)sulfonyl]vinyl}-N$^2$-(1H-indol-5-yl)-N$^4$-(1-methyl-1H-pyrazol-3-yl)pyrimidine-2,4-diamine (15s)

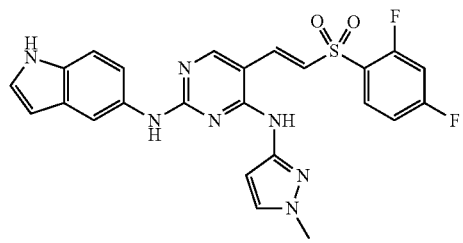

(15s)

The title compound was prepared starting from compound (14e) and 1H-indole-5-amine by the method of General Procedure L. $^1$H NMR (300 MHz, DMSO-$d_6$), δ 3.79 (s, NCH$_3$, 3H), 6.31 (bs, Ar—H, 1H), 6.51 (bs, NH, 1H), 7.40-7.22 (m, Ar—H & =CH, 4H), 7.61-7.59 (m, Ar—H, 2H), 8.09-7.93 (m, Ar—H & =CH, 3H), 8.60 (s, Ar—H, 1H), 9.53 (s, Ar—H, 1H), 9.83 (bs, NH, 1H), 10.95 (bs, NH, 1H).

Example 98. (E)-5-{2-[(2,4-Difluorophenyl)sulfonyl]vinyl}-N-(1-methyl-1H-pyrazol-3-yl)-N²-(4-morpholinophenyl)pyrimidine-2,4-diamine (15t)

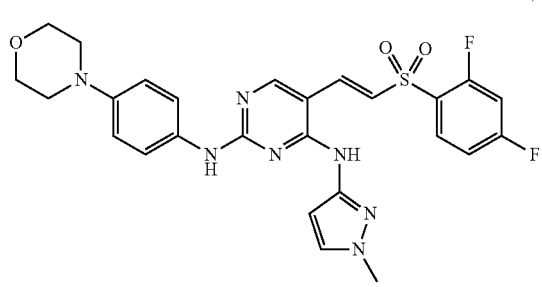

The title compound was prepared starting from compound (14e) and 4-morpholinoaniline by the method of General Procedure L. ¹H NMR (300 MHz, DMSO-d₆), δ 3.24-3.15 (m, CH₂, 4H), 3.83 (s, NCH₃, 3H), 3.92-3.89 (m, CH₂, 4H), 6.54 (bs, NH, 1H), 6.82 (d, =CH, J=15.3 Hz, 1H), 7.10-6.91 (m, Ar—H, 5H), 7.27-7.22 (m, Ar—H, 1H), 7.46-7.42 (m, Ar—H, 2H), 7.68 (d, =CH, J=15.0 Hz, 1H), 8.06-7.98 (m, Ar—H, 1H), 8.18 (s, Ar—H, 1H), 8.38 (bs, NH, 1H).

Example 99. (E)-5-{2-[(2,4-Difluorophenyl)sulfonyl]vinyl}-N⁴-(1-methyl-1H-pyrazol-3-yl)-N²-(quinolin-6-yl)pyrimidine-2,4-diamine (15u)

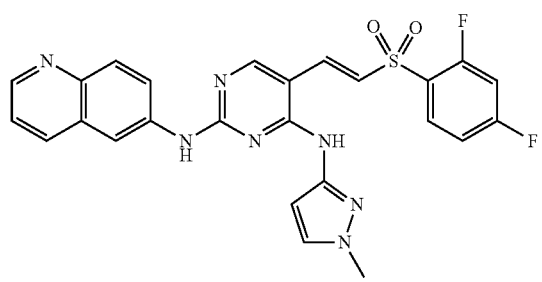

The title compound was prepared starting from compound (14e) and 6-aminoquinoline by the method of General Procedure L. ¹H NMR (300 MHz, DMSO-d₆), δ 3.81 (s, NCH₃, 3H), 6.64 (bs, NH, 1H), 7.04-6.83 (m, Ar—H & =CH, 3H), 7.32-7.30 (m, Ar—H, 1H), 7.42-7.37 (m, Ar—H, 1H), 7.81-7.51 (m, Ar—H, 2H), 8.08-7.79 (m, Ar—H & =CH, 4H), 8.29-8.28 (m, Ar—H, 1H), 8.34 (s, Ar—H, 1H), 8.82-8.81 (m, Ar—H, 1H).

Example 100. (E)-3-(4-(Cyclopentylamino)-2-(methylsulfanyl)pyrimidin-5-yl)acrylic acid ethyl ester (19)

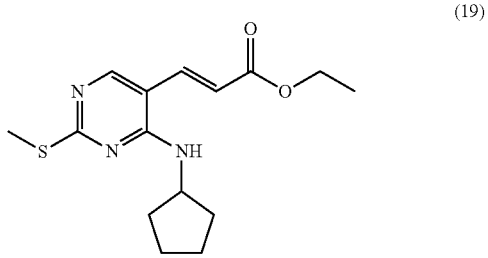 [SMILES: CCOC(=O)/C=C/c1cnc(SC)nc1NC1CCCC1]

Under nitrogen, an ice-cooled flask containing THF (50 mL) was charged with NaH (25 mmol, 60% dispersion in mineral oil) to which was added triethyl phosphonoacetate (25 mmol). The cooling bath was removed, and a solution of compound 4h (10 mmol) in THF (70 mL) was slowly added. The reaction was stirred for 6 h at room temperature. The reaction mixture was diluted with water and EtOAc. The layers were separated, and the aqueous layer was extracted with EtOAc. The combined organics were washed with brine and dried over Na₂SO₄ and the filtrate was concentrated under reduced pressure to provide compound 19.

Example 101. (E)-3-(4-(Cyclopentylamino)-2-(methylsulfinyl)pyrimidin-5-yl)acrylic acid ethyl ester (20)

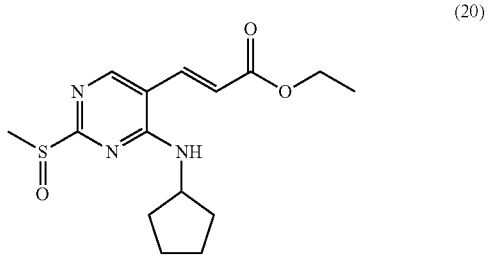 [SMILES: CCOC(=O)/C=C/c1cnc(S(C)=O)nc1NC1CCCC1]

A solution of compound 19 (1 equiv.), and mCPBA (1.25 equiv.) in DCM was stirred at room temperature for about 12 h. After completion of the reaction, the reaction mixture was washed with saturated NaHCO₃, and the organic layer was dried over Na₂SO₄ and evaporated under reduced pressure to obtain the product 20, which was used for next reaction without further purification.

Example 102. (E)-3-[4-(Cyclopentylamino)-2-{[4-(4-methylpiperazin-1-yl)phenyl]amino}pyrimidin-5-yl]acrylic acid ethyl ester (2l)

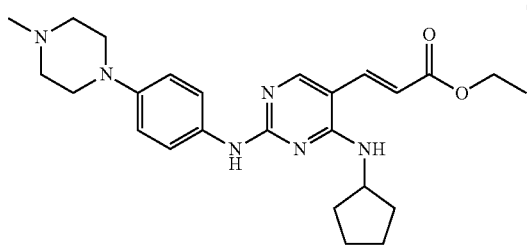

(2l)

A mixture of compound 20 (1 equiv.) and an 4-(4-methylpiperazin-1-yl)aniline (1.2 equiv.) in toluene was stirred at 100° C. overnight. The reaction mixture was cooled and solids were collected by filtration and the product 2l was purified flash column chromatography on silica gel using 2-4% methanol in chloroform as the eluant. $^1$H NMR (300 MHz, DMSO-$d_6$), δ 1.37-1.32 (t, CH$_3$, 3H), 1.78-1.64 (m, CH$_2$, 6H), 2.19-2.10 (m, CH$_2$, 2H), 2.39 (s, NCH$_3$, 3H), 3.89 (s, OCH$_3$, 3H), 2.63-2.59 (m, CH$_2$, 4H), 3.21-3.18 (m, CH$_2$, 4H), 4.30-4.23 (q, CH$_2$, 2H), 4.48-4.41 (m, C—H, 1H), 5.06 (bs, NH, 1H), 6.14 (d, =CH, J=15.6 Hz, 1H), 6.96-6.92 (m, Ar—H, 2H), 7.07 (bs, NH, 1H), 7.54-7.49 (m, Ar—H & =CH, 3H), 8.14 (s, Ar—H, 1H).

Example A. Cytotoxicity of Selected Compounds on K562 and DU145 Cancer Cell Lines The effect of the compounds described herein on tumor cells was determined by the assay described by Latham et al., Oncogene 12:827-837 (1996). Tumor cells K562 (chronic myelogenous leukemia; leukemia cell line +ve for Bcr-Abl) or DU145 (prostate cancer) were plated in 12-well dishes at a cell density of 2.5×10$^4$ cells per well. The plated cells were treated 24 h. later with a DMSO solution of a compound as described herein at multiple concentrations ranging from 0.01 μM to 100 μM. The plates were examined 96 h. later under an inverted microscope, Olympus CK-2 using a 10× objective, and compound activity was noted by physical observation. When necessary, the total number of viable cells was determined by trypsinizing the wells and counting the number of viable cells, as determined by trypan blue exclusion, using a hemacytometer. The IC$_{50}$ values for each compound are shown in Table 1.

TABLE 1

| Example | Compound No. | K562[†] | DU145[†] |
|---|---|---|---|
| 25 | 8a | +++ | +++ |
| 26 | 8b | ++++ | +++ |
| 27 | 8c | ++++ | ++++ |
| 28 | 8d | ++++ | ++++ |
| 29 | 8e | ++++ | ++++ |
| 30 | 8f | ++++ | ++++ |
| 31 | 8g | ++++ | ++++ |
| 32 | 8h | ++++ | ++++ |
| 33 | 8i | ++++ | +++ |
| 34 | 8j | +++ | +++ |
| 35 | 8k | ++++ | +++ |
| 36 | 8l | +++ | +++ |
| 37 | 8m | ++++ | ++++ |
| 38 | 8n | +++ | +++ |
| 39 | 8o | ++++ | ++++ |
| 40 | 8p | ++ | ++ |
| 41 | 8q | ++++ | ++++ |
| 42 | 8r | ++++ | ++++ |
| 43 | 8s | +++ | +++ |
| 44 | 8t | ++++ | ++++ |
| 45 | 8u | ++++ | ++++ |
| 46 | 8v | ++ | ++ |
| 47 | 8w | +++ | +++ |
| 48 | 8x | ++++ | ++++ |
| 49 | 8y | +++ | +++ |
| 54 | 15a | +++ | +++ |
| 55 | 15b | +++ | +++ |
| 56 | 15c | +++ | +++ |
| 71 | 8z | +++ | +++ |
| 74 | 8aa | +++ | +++ |
| 75 | 8bb | +++ | +++ |
| 76 | 15d | +++ | +++ |
| 77 | 15e | + | + |
| 78 | 15f | ++ | ++ |
| 79 | 15g | + | +++ |
| 80 | 15h | +++ | +++ |
| 81 | 15i | +++ | +++ |
| 84 | 15j | +++ | +++ |
| 85 | 15k | +++ | +++ |
| 86 | 15l | +++ | +++ |
| 87 | 15m | +++ | +++ |
| 88 | 15n | +++ | +++ |
| 89 | 15o | +++ | +++ |
| 90 | 15p | + | +++ |
| 93 | 15q | ++++ | +++ |
| 96 | 15r | +++ | +++ |
| 97 | 15s | +++ | +++ |
| 98 | 15t | +++ | +++ |
| 99 | 15u | +++ | +++ |
| 102 | 2l | ++++ | +++ |

[†]IC$_{50}$ values are indicated as follows: ++++: IC$_{50}$: <1 μM +++: IC$_{50}$: 1-25 μM ++: IC$_{50}$: >25-50 μM +: IC$_{50}$: >50-100 μM

Example B. Kinase Inhibition Assay

Kinase assays were performed at Reaction Biology Corporation. To a freshly prepared buffer solution was added the target kinase at a concentration of 20 μM. The contents were mixed gently, and then compound 8h dissolved in DMSO was added to the reaction mixture in the appropriate concentration. The mixture was incubated at room temperature for 30 min. prior to addition of ATP to initiate the reaction. Compound 8h was tested in a 5-dose IC$_{50}$ mode with 10-fold serial dilutions starting at 10 μM. For each of the kinases, a control compound in a 10-dose IC$_{50}$ mode with 3-fold serial dilutions starting at 20 μM. The control compounds were GW5074 (3-(3,5-dibromo-4-hydroxy-benzylidene)-5-iodo-1,3-dihydro-indol-2-one) for BRAF, CK2a and RAF1, D4476 (4-[4-(2,3-dihydro-1,4-benzodioxin-6-yl)-5-(2-pyridinyl)-1H-imidazol-2-yl]benzamide) for CK1d; Wee1 inhibitor (4-(2-chlorophenyl)-9-hydroxypyrrolo[3,4-c]carbazole-1,3-(2H,6H)-dione) for WEE1 and saturosporine for other kinases. Reaction was carried out at 10 μM ATP concentration.

Results are shown in Table 2.

TABLE 2

| Kinase | IC$_{50}$ (nM)[‡] |
|---|---|
| ABL1 | +++ |
| AKT1 | + |
| ALK | +++ |
| ARK5/NUAK1 | +++ |

TABLE 2-continued

| Kinase | IC$_{50}$ (nM)‡ |
|---|---|
| Aurora A | ++ |
| Aurora B | +++ |
| Aurora C | + |
| c-Kit | ++ |
| c-Src | +++ |
| CDK1/cyclin B | − |
| CDK2/cyclin A | + |
| CDK4/cyclin D1 | ++ |
| CDK5/p25 | >10000 |
| CDK5/p35 | >10000 |
| CDK6/cyclin D1 | ++ |
| CHK1 | ++ |
| CHK2 | ++ |
| CK2a2 | ++ |
| EGFR | ++ |
| FGFR1 | +++ |
| FLT3 | +++ |
| JAK1 | ++ |
| JAK2 | ++ |
| JAK3 | ++ |
| MEK1 | + |
| MEK2 | + |
| PDGFRb | +++ |
| PIM1 | + |
| PIM2 | + |
| PIM3 | + |
| PLK1 | ++ |
| PLK2 | + |
| RET | +++ |
| RSK4 | +++ |

‡IC$_{50}$ values are indicated as follows: +++: IC$_{50}$ <100 nM ++: 100 nM ≤ IC$_{50}$ < 1000 nM +: IC$_{50}$: >1000 nM Example C. Inhibition of ABL Mutants Kinase assays were performed at Reaction Biology Corporation. To a freshly prepared buffer solution was added the target kinase at a concentration of 20 µM. The contents were mixed gently, and then compound (8h) dissolved in DMSO was added to the reaction mixture in the appropriate concentration. The mixture was incubated at room temperature for 30 min. prior to addition of ATP to initiate the reaction. Compound (8h) was tested in a 5-dose IC$_{50}$ mode with 10-fold serial dilutions starting at 10 µM. Staurosporine was used as a control compound in a 10-dose IC$_{50}$ mode with 3-fold serial dilutions starting at 20 µM. Reaction was carried out at 10 µM ATP concentration.

Results are shown in Table 3.

TABLE 3

| Kinase | IC$_{50}$ (nm)‡ |
|---|---|
| ABL1 (E255K) | +++ |
| ABL1 (G250E) | +++ |
| ABL1 (H396P) | +++ |
| ABL1 (M351T) | +++ |
| ABL1 (Q252H) | +++ |
| ABL1 (T315I) | +++ |
| ABL1 (Y253F) | +++ |
| ABL2/ARG | +++ |

‡IC$_{50}$ values are indicated as follows: +++: IC$_{50}$ <100 nM ++: 100 nM ≤ IC$_{50}$ < 1000 nM +: IC$_{50}$: >1000 nM Example D. Cytotoxicity Assay The following tumor cell lines were tested using a dose response end point assay system with compound (8h). The cells were grown in either DMEM or RPMI supplemented with 10% fetal bovine serum and 1 unit/mL Penicillin-Streptomycin solution. The tumor cells were plated into 6-well dishes at a cell density of 1.0×10$^5$ cells/mL/well and the test compound was added 24 h. later at various concentrations. Cell counts were determined from duplicate wells after 96 h. of treatment. The total number of viable cells was determined by trypan blue exclusion.

TABLE 4

| Cell Line | Tumor Type | GI$_{50}$ Values (µM) |
|---|---|---|
| K562 | chronic myelogenous leukemia | 0.04 |
| DU145 | prostate carcinoma | <0.5 |
| 32D-T315I | chronic myelogenous leukemia | 0.5 |
| HEL | human erythroleukemia | <0.25 |
| Z138C | mantle cell lymphoma | 3 |
| RAJI | Burkitt's lymphoma | <0.02 |
| KG-1a | acute myelogenous leukemia | <0.02 |
| DAUDI | Burkitt's lymphoma | 0.1 |
| MOLT-4 | acute lymphoblastic leukemia | 0.1 |
| MES-SA | uterine sarcoma | 0.02 |
| MES-SA/DX5 | Uterine sarcoma | <0.02 |
| HELA | Cervical adenocarinoma | >5.0 |
| BT474 | Breast carcinoma | 2.5 |
| HT-29 | colonic adenocarinoma | 0.05 |
| HCT-116 | colon cancer | 0.5 |
| A431 | epidermoid carcinoma | 0.1 |
| HCT-15 | Dukes' type C colorectal adenocarcinoma | 0.03 |
| U266 | multiple myeloma | 1 |
| U937 | histiocytic lymphoma | 0.1 |
| CEM | T-cell leukemia | 1.5 |
| CEM/C2 | T-cell leukemia | 1.5 |
| HL-60 | promyelocytic leukaemia | 0.5 |
| HL-60/MX2 | promyelocytic leukaemia | 0.25 |
| HFL-1 | fetal lung fibroblast | 0.1 |
| Nalmalwa | Burkitt's lymphoma | 0.2 |
| BXPC-3 | pancreatic adenocarcinoma | 0.1 |
| SU.86.86 | pancreatic ductal carcinoma | 5 |
| PANC 10.05 | pancreatic adenocarcinoma | >5 |
| PANC 03.27 | Pancreatic adenocarcinoma | 3 |
| ASPC-1 | pancreatic adenocarcinoma | >5.0 |
| MIA-PaCa-2 | pancreatic carcinoma | >5.0 |
| CAPAN-1 | pancreatic ductal adenocarcinoma | 0.1 |
| HPAF-II | pancreatic adenocarcinoma | 5 |
| K562 | chronic myelogenous leukemia | 0.01† |
| DU145 | prostate carcinoma | 0.05† |
| LNCap | Prostate adenocarcinoma | 0.25† |

†Data obtained using HCl salt of compound (8h).

All patents, applications, published applications and other publications cited in the present disclosure are hereby incorporated by reference in their entirety.

A number of embodiments of the invention have been described. Nevertheless, it will be understood that various modifications may be made without departing from the spirit and scope of the invention. Accordingly, other embodiments are within the scope of the following claims.

What is claimed is:
1. A compound of formula (I):

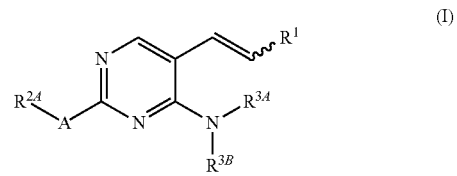

or a salt thereof, wherein:
R$^1$ is CN, S(O)$_j$Ar$^1$, or S(O)$_k$(C$_{1-6}$ alkylene)Ar$^1$;
j is 0, 1 or 2;
k is 0, 1 or 2;

each Ar¹ is independently $C_{6-10}$ aryl or 5-10 membered heteroaryl, each of which is unsubstituted or substituted by 1, 2, 3, 4 or 5 substituents independently selected from $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $Cy^1$ is independently $C_{6-10}$ aryl, $C_{3-10}$ cycloalkyl, 5-10 membered heteroaryl or 4-10 membered heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;

A is $NR^{2B}$;

$R^{2A}$ is $C_{1-6}$ alkyl, $C_{2-6}$ alkenyl, $C_{2-6}$ alkynyl, $Ar^2$ or ($C_{1-6}$ alkylene)$Ar^2$;

$R^{2B}$ is H, $C_{1-6}$ alkyl, $C(O)C_{1-6}$ alkyl, $Cy^{2A}$, $C(O)Cy^{2A}$, ($C_{1-6}$ alkylene)$Cy^{2A}$ and $C(O)(C_{1-6}$ alkylene)$Cy^{2A}$;

or $R^{2A}$ and $R^{2B}$, together with the N atom to which they are attached, form a 5-, 6-, or 7-membered heterocycloalkyl group, which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo;

$Ar^2$ is $C_{6-10}$ aryl or 5-10 membered heteroaryl, each of which is unsubstituted or substituted by 1, 2, 3, 4 or 5 substituents independently selected from $Cy^{2B}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}S(O)R^{b2}$, $S(O)NR^{c2}R^{d2}$, $S(O)_2R^{b2}$ and $S(O)_2NR^{c2}R^{d2}$;

$Cy^{2A}$ is $C_{6-10}$ aryl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $Cy^{2B}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})$ $NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo;

each $Cy^{2B}$ is independently $C_{6-10}$ aryl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo;

$R^{3A}$ is H, $Cy^{3A1}$ or $C_{1-6}$ alkyl, $C_{2-6}$ alkenyl, $C_{1-6}$ alkynyl, wherein said $C_{1-6}$ alkyl forming $R^{3A}$ is optionally substituted with 1, 2, or 3 substituents independently selected from $Cy^{3A2}$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{d3})NR^{c3}R^{d3}$, $NR^{c3}C(=NR^{d3})$ $NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

$R^{3B}$ is H, $Cy^{3B1}$ or $C_{1-6}$ alkyl, $C_{2-6}$ alkenyl, $C_{1-6}$ alkynyl, wherein said $C_{1-6}$ alkyl forming $R^{3B}$ is optionally substituted with 1, 2, or 3 substituents independently selected from $Cy^{3B2}$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{d3})NR^{c3}R^{d3}$, $NR^{c3}C(=NR^{d3})$ $NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

each $Cy^{3A1}$, $Cy^{3A2}$, $Cy^{3B1}$ and $Cy^{3B2}$ is, independently, $C_{6-10}$ aryl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})$ $NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

or $R^{3A}$ and $R^{3B}$, together with the N atom to which they are attached, form a 5-, 6-, or 7-membered heterocycloalkyl group, which is unsubstituted or substituted by 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo;

each $R^{Cy3}$ is independently selected from $C_{6-10}$ aryl, $C_{3-7}$ cycloalkyl, 5-10 membered heteroaryl, 5-10 heterocycloalkyl, $C_{1-6}$ alkyl, $C_{2-6}$ alkenyl, $C_{2-6}$ alkynyl, halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$ $NR^{c3}R^{d3}$ $NR^{c3}C(O)R^{b3}$ $NR^{c3}C(O)OR^{a3}$, $NR^{c3}C(O)$ $NR^{c3}R^{d3}$, $NR^{c3}S(O)R^{b3}$, $NR^{c3}S(O)_2R^{b3}$, $NR^{c3}S(O)_2$ $NR^{c3}R^{d3}$, $S(O)R^{b3}$, $S(O)NR^{c3}R^{d3}$, $S(O)_2R^{b3}$, $S(O)_2$ $NR^{c3}R^{d3}$ and oxo; wherein each of said $C_{6-10}$ aryl, $C_{3-7}$ cycloalkyl, 5-10 membered heteroaryl and 5-10 heterocycloalkyl forming $R^{Cy3}$ is independently unsubstituted or substituted by 1, 2, or 3 substituents independently selected from $C_{1-6}$ alkyl, $C_{2-6}$ alkenyl, $C_{2-6}$ alkynyl, halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)$ $NR^{c3}R^{d3}$, $C(=NR^{e3})NR^{c3}R^{d3}$, $NR^{c3}C(=NR^{e3})$ $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2$ $R^{b3}$, $S(O)_2NR^{c3}R^{d3}$ and oxo;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$ and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

or any $R^{c1}$ and $R^{d1}$ attached to the same N atom, any $R^{c2}$ and $R^{d2}$ attached to the same N atom, any $R^{c3}$ and $R^{d3}$ attached to the same N atom, or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl, $C_{3-7}$ cycloalkyl, 3-7 membered heterocycloalkyl, $C_{6-10}$ aryl, 5-6 membered heteroaryl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$ $NR^{c4}C(O)R^{b4}$ $NR^{c4}C(O)NR^{c4}R^{d4}$ $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c4}$ and $R^{d4}$ attached to the same N atom, together with the N atom to which they are attached, form a 3-, 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl and $C_{1-4}$ haloalkoxy; and each $R^{e1}$, $R^{e2}$, $R^{e3}$ and $R^{e4}$ is independently selected from H, $C_{1-4}$ alkyl and CN;

with the proviso that the compound is other than 3-(4-ethylamino-2-phenylamino-pyrimidin-5-yl)acrylonitrile and salts thereof.

2. A compound or salt thereof of claim 1, wherein:

$R^1$ is CN, $S(O)_2Ar^1$, or $S(O)_2(C_{1-6}$ alkylene)$Ar^1$;

each $Ar^1$ is independently phenyl, which is unsubstituted or substituted by 1, 2, 3, 4 or 5 substituents independently selected from $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $NR^{c1}R^{d1}$, and $NR^{c1}C(O)R^{b1}$;

each $Cy^1$ is independently $C_{6-10}$ aryl, $C_{3-10}$ cycloalkyl, 5-10 membered heteroaryl or 4-10 membered heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $NR^{c1}R^{d1}$, $NR^{c1}C(O)R^{b1}$ and oxo;

A is $NR^{2B}$;

$R^{2A}$ is $C_{1-6}$ alkyl, $C_{2-6}$ alkenyl, $C_{2-6}$ alkynyl, $Ar^2$ or ($C_{1-6}$ alkylene)$Ar^2$;

$R^{2B}$ is H, $C_{1-6}$ alkyl, $C(O)C_{1-6}$ alkyl, $Cy^{2A}$, $C(O)Cy^{2A}$, ($C_{1-6}$ alkylene)$Cy^{2A}$ and $C(O)(C_{1-6}$ alkylene)$Cy^{2A}$;

or $R^{2A}$ and $R^{2B}$, together with the N atom to which they are attached, form a 5-, 6-, or 7-membered heterocycloalkyl group, which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $NR^{c2}R^{d2}$ $NR^{c2}C(O)R^{b2}$, and oxo;

$Ar^2$ is phenyl or 5-10 membered heteroaryl, each of which is unsubstituted or substituted by 1, 2, 3, 4 or 5 substituents independently selected from $Cy^{2B}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $NR^{c2}R^{d2}$, and $NR^{c2}C(O)R^{b2}$;

$Cy^{2A}$ is $C_{6-10}$ aryl, $C_{3-7}$ cycloalkyl, 5-10 membered heteroaryl, or 5-10 heterocycloalkyl, each of which is unsubstituted or substituted by 1, 2, 3 or 5 substituents independently selected from $Cy^{2B}$, $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and oxo;

each $Cy^{2B}$ is independently phenyl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $NR^{c2}R^{d2}$, $NR^{c2}C(O)R^{b2}$ and oxo;

$R^{3A}$ is H, $Cy^{3A1}$ or $C_{1-6}$ alkyl, $C_{2-6}$ alkenyl, $C_{1-6}$ alkynyl, wherein said $C_{1-6}$ alkyl forming $R^{3A}$ is optionally substituted with 1, 2, or 3 substituents independently selected from $Cy^{3A2}$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $NR^{c3}R^{d3}$, $NR^{c3}C(O)R^{b3}$ and oxo;

$R^{3B}$ is H or $C_{1-6}$ alkyl;

each $Cy^{3A1}$ and $Cy^{3A2}$ is, independently, phenyl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $NR^{c3}R^{d3}$, $NR^{c3}C(O)R^{b3}$ and oxo;

or $R^{3A}$ and $R^{3B}$, together with the N atom to which they are attached, form a 5-, 6-, or 7-membered heterocycloalkyl group, which is unsubstituted or substituted by 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $NR^{c3}R^{d3}$ $NR^{c3}C(O)R^{b3}$ $NR^{c3}C(O)OR^{a3}$ and oxo;

each $R^{Cy3}$ is independently selected from phenyl, $C_{3-7}$ cycloalkyl, 5-10 membered heteroaryl, 5-10 heterocycloalkyl, $C_{1-6}$ alkyl, $C_{2-6}$ alkenyl, $C_{2-6}$ alkynyl, halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $NR^{c3}R^{d3}$ $NR^{c3}C(O)R^{b3}$, and oxo; wherein each of said phenyl, $C_{3-7}$ cycloalkyl, 5-10 membered heteroaryl and 5-10 heterocycloalkyl forming $R^{Cy3}$ is independently unsubstituted or substituted by 1, 2, or 3 substituents independently selected from $C_{1-6}$ alkyl, $C_{2-6}$ alkenyl, $C_{2-6}$ alkynyl, halo, $C_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, NR$^{c3}$R$^{d3}$, NR$^{c3}$C(O)R$^{b3}$, and oxo;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$ and $R^{d3}$ is independently selected from H and $C_{1-6}$ alkyl;

or any $R^{c1}$ and $R^{d1}$ attached to the same N atom, any $R^{c2}$ and $R^{d2}$ attached to the same N atom, any $R^{c3}$ and $R^{d3}$ attached to the same N atom, or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl;

each $R^{a4}$, $R^{b4}$, $R^{c4}$ and $R^{d4}$ is independently selected from H and $C_{1-4}$ alkyl; and or any $R^{c4}$ and $R^{d4}$ attached to the same N atom, together with the N atom to which they are attached, form a 3-, 4-, 5-, 6-, or 7-membered heterocycloalkyl group optionally substituted with 1, 2, or 3 substituents independently selected from $C_{1-6}$ alkyl.

3. A compound or salt thereof of claim 1, wherein:
$R^1$ is CN;
A is $NR^{2B}$;
$R^{2A}$ is $C_{1-6}$ alkyl, $C_{2-6}$ alkenyl, $C_{2-6}$ alkynyl, Ar$^2$ or ($C_{1-6}$ alkylene)Ar$^2$;
$R^{2B}$ is H or $C_{1-6}$ alkyl;
or $R^{2A}$ and $R^{2B}$, together with the N atom to which they are attached, form a 5-, 6-, or 7-membered heterocycloalkyl group, which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, NR$^{c2}$R$^{d2}$, NR$^{c2}$C(O)R$^{b2}$, and oxo;

Ar$^2$ is phenyl or 5-10 membered heteroaryl, each of which is unsubstituted or substituted by 1, 2, 3, 4 or 5 substituents independently selected from Cy$^{2B}$, $C_{1-6}$ alkyl, $C_2$-6 alkenyl, $C_{2-6}$ alkynyl, halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, NR$^{c2}$R$^{d2}$, and NR$^{c2}$C(O)R$^{b2}$;

Cy$^{2A}$ is phenyl, $C_{3-7}$ cycloalkyl, 5-10 membered heteroaryl, or 5-10 heterocycloalkyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, NO$_2$, OR$^{a2}$, SR$^{a2}$, C(O)R$^{b2}$, C(O)NR$^{c2}$R$^{d2}$, C(O)OR$^{a2}$, NR$^{c2}$R$^{d2}$, NR$^{c2}$C(O)R$^{b2}$, and oxo;

$R^{3A}$ is H, Cy$^{3A1}$ or $C_{1-6}$ alkyl, $C_{2-6}$ alkenyl, $C_{1-6}$ alkynyl, wherein said $C_{1-6}$ alkyl forming $R^{3A}$ is optionally substituted with Cy$^{3A2}$ and is optionally substituted with 1, 2, or 3 substituents independently selected from halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, NR$^{c3}$R$^{d3}$ NR$^{c3}$C(O)R$^{b3}$ and oxo;

$R^{3B}$ is H or $C_{1-6}$ alkyl;

each Cy$^{3A1}$ and Cy$^{3A2}$ is, independently, $C_{3-7}$ cycloalkyl or 5-10 membered heteroaryl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, NR$^{c3}$R$^{d3}$, NR$^{c3}$C(O)R$^{b3}$ and oxo;

or $R^{3A}$ and $R^{3B}$, together with the N atom to which they are attached, form a 5-, 6-, or 7-membered heterocycloalkyl group, which is unsubstituted or substituted by 3, 4 or 5 substituents independently selected from $C_{1-6}$ alkyl, $C_{2-6}$ alkenyl, $C_{2-6}$ alkynyl, halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, NR$^{c3}$R$^{d3}$ NR$^{c3}$C(O)R$^{b3}$ NR$^{c3}$C(O)OR$^{a3}$ and oxo;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$ and $R^{d3}$ is independently selected from H and $C_{1-6}$ alkyl;

or any $R^{c1}$ and $R^{d1}$ attached to the same N atom, any $R^{c2}$ and $R^{d2}$ attached to the same N atom, any $R^{c3}$ and $R^{d3}$ attached to the same N atom, or any $R^{c4}$ and $R^{d4}$ attached to the same N atom, together with the N atom to which they are attached, form a 4-, 5-, 6- or 7-membered heterocycloalkyl group optionally substituted with 1, 2 or 3 substituents independently selected from $C_{1-6}$ alkyl;

each $R^{a4}$, $R^{b4}$, $R^{c4}$ and $R^{d4}$ is independently selected from H and $C_{1-4}$ alkyl; and or any $R^{c4}$ and $R^{d4}$ attached to the same N atom, together with the N atom to which they are attached, form a 3-, 4-, 5-, 6-, or 7-membered heterocycloalkyl group optionally substituted with 1, 2, or 3 substituents independently selected from $C_{1-6}$ alkyl.

4. A compound or salt thereof according to claim 1, wherein the —CH═CH—R$^1$ group of the compound has (E)-stereochemistry.

5. A compound or salt thereof according to claim 1, wherein R$^1$ is CN.

6. A compound or salt thereof according to claim 1, wherein:
$R^1$ is S(O)$_j$Ar$^1$ or —S(O)$_k$(C$_{1-6}$ alkylene)Ar$^1$;
j is 2,
k is 2;
Ar$^1$ is unsubstituted or substituted phenyl, and
wherein Ar$^1$, when substituted, is substituted by 1, 2 or 3 substituents independently selected from Cy$^1$, $C_{1-6}$ alkyl, $C_{2-6}$ alkenyl, $C_{2-6}$ alkynyl, halo, $C_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(═NR$^{e1}$)NR$^{c1}$R$^{d1}$, NR$^{c1}$C(═NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$ and S(O)$_2$NR$^{c1}$R$^{d1}$.

7. A compound or salt thereof according to claim 1, wherein $R^{2A}$ is Ar$^2$ or CH$_2$Ar$^2$, and wherein Ar$^2$ is unsubstituted or substituted phenyl or unsubstituted or substituted heteroaryl.

8. A compound or salt thereof according to claim 7, wherein Ar$^2$ is phenyl substituted at the 4-position by substituted or unsubstituted 5-10 membered heterocycloalkyl.

9. A compound or salt thereof according to claim 8, wherein Ar$^2$ is phenyl substituted at the 4-position by substituted or unsubstituted 5-10 membered heterocycloalkyl wherein the heterocycloalkyl is selected from piperazin-1-yl, piperidin-4-yl.

10. A compound or salt thereof according to claim 7, wherein Ar$^2$ is indolyl or pyridyl.

11. A compound or salt thereof according to claim 1, wherein $R^{2B}$ is hydrogen.

12. A compound or salt thereof according to claim 1, wherein $R^{2A}$ and $R^{2B}$, together with the N atom to which they are attached, form a 5-, 6-, or 7-membered heterocycloalkyl group, which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(═NR$^{e2}$)NR$^{c2}$R$^{d2}$, NR$^{c2}$C(═NR$^{e2}$)NR$^{c2}$R$^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, $S(O)_2NR^{c2}R^{d2}$ and oxo.

13. A compound or salt thereof according to claim 1, wherein $R^{3A}$ is H, $C_{1-6}$ alkyl, $C_{2-6}$ alkenyl, $C_{1-6}$ alkynyl, $Cy^{3A1}$ or $(CH_2)Cy^{3A2}$.

14. A compound or salt thereof according to claim 13, wherein:
   $R^{3A}$ is $Cy^{3A1}$ or $(CH_2)Cy^{3A2}$;
   $Cy^{3A1}$ is $C_{3-7}$ cycloalkyl, which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo; and
   $Cy^{3A2}$ is $C_{3-7}$ cycloalkyl, which is unsubstituted or substituted by 1, 2, 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo.

15. A compound or salt thereof according to claim 14, wherein $R^{3A}$ is $C_{3-7}$ cycloalkyl or $(CH_2)C_{3-7}$ cycloalkyl.

16. A compound or salt thereof according to claim 15, wherein $R^{3A}$ is cyclopropyl, cyclobutyl, cyclopentyl, cyclohexyl, cycloheptyl, cyclopropylmethyl, cyclobutylmethyl, cyclopentylmethyl, cyclohexylmethyl or cycloheptylmethyl.

17. A compound or salt thereof according to claim 1, wherein $R^{3B}$ is H or $C_{1-6}$ alkyl.

18. A compound or salt thereof according to claim 1, wherein $R^{3A}$ and $R^{3B}$, together with the N atom to which they are attached, form a 5-, 6-, or 7-membered heterocycloalkyl group, which is unsubstituted or substituted by 3, 4 or 5 substituents independently selected from $R^{Cy3}$, $C_{1-6}$ alkyl, $C_{2-6}$ alkenyl, $C_{2-6}$ alkynyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and oxo.

19. A compound or salt thereof according to claim 18, wherein $R^{3A}$ and $R^{3B}$, together with the N atom to which they are attached, form a 5-, 6-, or 7-membered heterocycloalkyl group, which is unsubstituted.

20. A compound or salt thereof according to claim 19, wherein $R^{3A}$ and $R^{3B}$, together with the N atom to which they are attached, form a pyrrolidinyl, piperidinyl, azepanyl or morpholinyl group.

21. A compound selected from the following compounds, and salts thereof:
   3-[4-Amino-2-(methylsulfanyl)pyrimidin-5-yl]acrylonitrile;
   3-[4-Ethylamino-2-(methylsulfanyl)pyrimidin-5-yl]acrylonitrile;
   3-[4-Propylamino-2-(methylsulfanyl)pyrimidin-5-yl]acrylonitrile;
   3-[4-Isopropylamino-2-(methylsulfanyl)pyrimidin-5-yl]acrylonitrile;
   3-[4-(Cyclopropylmethyl)amino-2-(methylsulfanyl)pyrimidin-5-yl]-acrylonitrile;
   3-[4-Cyclopropylamino-2-(methylsulfanyl)pyrimidin-5-yl]acrylonitrile;
   3-[4-Cyclopentylamino-2-(methylsulfanyl)pyrimidin-5-yl]acrylonitrile;
   3-[4-Cyclohexylamino-2-(methylsulfanyl)pyrimidin-5-yl]acrylonitrile;
   3-[4-(N-Ethyl-N-methylamino)-2-(methylsulfanyl)pyrimidin-5-yl]acrylonitrile;
   3-[2-Methylsulfanyl-4-(pyrrolidin-1-yl)pyrimidin-5-yl]acrylonitrile;
   3-[4-(N-Cyclopentyl-N-ethylamino)-2-(methylsulfanyl)pyrimidin-5-yl]acrylonitrile;
   5-{2-[(2,4-Difluorophenyl)sulfonyl]vinyl}-N-methyl-2-(methylsulfanyl)pyrimidin-4-amine;
   N-Cyclopentyl-5-{2-[(2,4-difluorophenyl) sulfonyl]vinyl}-2-(methylsulfanyl)pyrimidin-4-amine;
   3-[4-Amino-2-(methylsulfinyl)pyrimidin-5-yl]acrylonitrile;
   3-[4-Methylamino-2-(methylsulfinyl)pyrimidin-5-yl]acrylonitrile;
   3-[4-Ethylamino-2-(methylsulfinyl)pyrimidin-5-yl]acrylonitrile;
   3-[4-Propylamino-2-(methylsulfinyl)pyrimidin-5-yl]acrylonitrile;
   3-[4-Isopropylamino-2-(methylsulfinyl)pyrimidin-5-yl]acrylonitrile;
   3-[4-(Cyclopropylmethyl)amino-2-(methylsulfinyl)pyrimidin-5-yl]-acrylonitrile;
   3-[4-Cyclopropylamino-2-(methylsulfinyl)pyrimidin-5-yl]acrylonitrile;
   3-[4-Cyclopentylamino-2-(methylsulfinyl)pyrimidin-5-yl]acrylonitrile;
   3-[4-Cyclohexylamino-2-(methylsulfinyl)pyrimidin-5-yl] acrylonitrile 3-[4-(N-Ethyl-N-methylamino)-2-(methylsulfinyl)pyrimidin-5-yl]acrylonitrile;
   3-[2-Methylsulfinyl-4-(pyrrolidin-1-yl)pyrimidin-5-yl]acrylonitrile;
   3-[4-(N-Cyclopentyl-N-ethylamino)-2-(methylsulfinyl)pyrimidin-5-yl]acrylonitrile;
   5-{2-[(2,4-Difluorophenyl)sulfonyl]vinyl}-N-methyl-2-(methylsulfinyl)pyrimidin-4-amine;
   N-Cyclopentyl-5-{2-[(2,4-difluorophenyl)sulfonyl]vinyl}-2-(methylsulfinyl)pyrimidin-4-amine;
   3-{4-Amino-2-[4-(4-methylpiperazin-1-yl)phenylamino]pyrimidin-5-yl}acrylonitrile;
   3-{4-Methylamino-2-[4-(4-methylpiperazin-1-yl)-phenylamino]pyrimidin-5-yl}acrylonitrile;
   3-{4-Ethylamino-2-[4-(4-methylpiperazin-1-yl)phenylamino]pyrimidin-5-yl}acrylonitrile;
   3-{4-Propylamino-2-[4-(4-methylpiperazin-1-yl)phenylamino]pyrimidin-5-yl}acrylonitrile;
   3-{4-Isopropylamino-2-[4-(4-methylpiperazin-1-yl)phenylamino]pyrimidin-5-yl}acrylonitrile;
   3-{4-(Cyclopropylmethyl)amino-2-[4-(4-methylpiperazin-1-yl)phenylamino]pyrimidin-5-yl}acrylonitrile;
   3-{4-Cyclopropylamino-2-[4-(4-methylpiperazin-1-yl)phenylamino]pyrimidin-5-yl}acrylonitrile;
   3-{4-Cyclopentylamino-2-[4-(4-methylpiperazin-1-yl)phenylamino]pyrimidin-5-yl}acrylonitrile;
   3-{4-Cyclohexylamino-2-[4-(4-methylpiperazin-1-yl)phenylamino]pyrimidin-5-yl}acrylonitrile;
   3-{4-Cyclopentylamino-2-[(4-morpholin-4-yl)phenylamino]pyrimidin-5-yl}acrylonitrile;

3-[4-Cyclopentylamino-2-(1H-indol-5-ylamino)pyrimidin-5-yl]acrylonitrile;
3-{4-Cyclopentylamino-2-[4-(1-methylpiperidin-4-yl)phenylamino]pyrimidin-5-yl}acrylonitrile;
3-[2-(1H-Indol-5-ylamino)-4-(methylamino)pyrimidin-5-yl]acrylonitrile;
3-{4-(Cyclopentylamino)-2-[(4-methoxyphenyl)amino]pyrimidin-5-yl)acrylonitrile;
3-{4-Cyclopentylamino-2-[4-(1-ethylpiperazin-4-yl)-phenylamino]-pyrimidin-5-yl}acrylonitrile;
3-[2-(Benzylamino)-4-(cyclopentylamino)pyrimidin-5-yl]acrylonitrile;
3-(4-(Cyclopentylamino)-2-((5-(4-methylpiperazin-1-yl)pyridin-2-yl)amino)pyrimidin-5-yl)acrylonitrile;
3-{4-(Cyclopentylamino)-2-[(4-methoxyphenyl)amino]pyrimidin-5-yl)acrylonitrile;
3-{4-[(Cyclopropylmethyl)amino]-2-[4-(4-ethylpiperazin-1-yl)phenylamino]pyrimidin-5-yl}acrylonitrile;
3-{4-[(Cyclopropylmethyl)amino]-2-[(1H-indol-5-yl)amino]pyrimidin-5-yl)acrylonitrile;
3-{4-(N-Ethyl-N-methylamino)-2-[4-(4-methylpiperazin-1-yl)phenylamino]pyrimidin-5-yl}acrylonitrile;
3-{2-[4-(4-methylpiperazin-1-yl)phenylamino]-4-(pyrrolidin-1-yl)pyrimidin-5-yl}acrylonitrile;
3-{4-(N-Cyclopentyl-N-ethylamino)-2-[4-(4-methylpiperazin-1-yl)phenylamino]pyrimidin-5-yl}acrylonitrile;
3-{4-[N-(Cyclopropylmethyl)-N-ethylamino]-2-[4-(morpholin-4-yl)phenylamino]pyrimidin-5-yl}acrylonitrile;
N-[5-(2-Cyanovinyl)-4-(cyclopentylamino)pyrimidin-2-yl]-N-[4-(4-methylpiperazin-1-yl)phenyl]-5-((3aS,4S,6aR)-2-oxohexahydro-1H-thieno[3,4-d]imidazol-4-yl)pentanamide;
5-{2-[2,4-(Difluorophenyl)sulfonyl]vinyl}-$N^2$-(1H-indol-5-yl)-$N^4$-methylpyrimidine-2,4-diamine;
$N^4$-Cyclopentyl-5-{2-[(2, 4-difluorophenyl)sulfonyl]vinyl}-$N^2$-[4-(4-methylpiperazin-1-yl)phenyl]pyrimidine-2,4-diamine; and
5-{2-[2,4-(Difluorophenyl)sulfonyl]vinyl}-$N^2$-(1H-indol-6-yl)-$N^4$-methylpyrimidine-2,4-diamine;
N-methyl-2-(methylsulfanyl)-5-(2-nitrovinyl)pyrimidin-4-amine;
N-methyl-2-(methylsulfinyl)-5-(2-nitrovinyl)pyrimidin-4-amine;
$N^4$-methyl-$N^2$-[4-(4-methylpiperazin-1-yl)phenyl]-5-(2-nitrovinyl)pyrimidine-2,4-diamine;
N-Cyclopentyl-2-(methylsulfanyl)-5-(2-nitrovinyl)pyrimidin-4-amine;
N-Cyclopentyl-2-(methylsulfinyl)-5-(2-nitrovinyl)pyrimidin-4-amine;
$N^4$-Cyclopentyl-$N^2$-[4-(4-methylpiperazin-1-yl)phenyl]-5-(2-nitrovinyl)pyrimidine-2,4-diamine;
3-(4-(Methylamino)-2-{[4-(4-methylpiperazin-1-yl)phenyl]amino}pyrimidin-5-yl)acrylic acid;
3-(4-(Cyclopentylamino)-2-{[4-(4-methylpiperazin-1-yl)phenyl]amino}pyrimidin-5-yl)acrylic acid;
4-[4-(Methylamino)-2-(methylsulfanyl)pyrimidin-5-yl]but-3-en-2-one;
4-[4-(Methylamino)-2-(methylsulfinyl)pyrimidin-5-yl]but-3-en-2-one;
4-(4-(methylamino)-2-{[4-(4-methylpiperazin-1-yl)phenyl]amino}pyrimidin-5-yl)but-3-en-2-one;
4-[4-(Cyclopentylamino)-2-(methylsulfanyl)pyrimidin-5-yl]but-3-en-2-one;
4-[4-(Cyclopentylamino)-2-(methylsulfinyl)pyrimidin-5-yl]but-3-en-2-one; and
4-(4-(Cyclopentylamino)-2-{[4-(4-methylpiperazin-1-yl)phenyl]amino}pyrimidin-5-yl)but-3-en-2-one.

22. A compound according to claim 1, wherein the compound of formula (I) is 3-{4-Cyclopentylamino-2-[4-(4-methylpiperazin-1-yl)phenylamino]pyrimidin-5-yl}acrylonitrile, or a salt thereof.

23. A pharmaceutical composition comprising a compound according to claim 1, or a pharmaceutically acceptable salt thereof, and a pharmaceutically acceptable carrier.

* * * * *